United States Patent
Collias et al.

(10) Patent No.: US 10,487,035 B2
(45) Date of Patent: Nov. 26, 2019

(54) METHOD OF MAKING ACRYLIC ACID FROM HYDROXYPROPIONIC ACID

(71) Applicant: The Procter & Gamble Company, Cincinnati, OH (US)

(72) Inventors: Dimitris Ioannis Collias, Mason, OH (US); Jane Ellen Godlewski, Loveland, OH (US); Juan Esteban Velasquez, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/861,704

(22) Filed: Jan. 4, 2018

(65) Prior Publication Data

US 2018/0126187 A1    May 10, 2018

Related U.S. Application Data

(62) Division of application No. 15/342,428, filed on Nov. 3, 2016, now Pat. No. 9,890,102.

(51) Int. Cl.
| | |
|---|---|
| *C07C 51/377* | (2006.01) |
| *C07C 45/66* | (2006.01) |
| *B01J 27/18* | (2006.01) |
| *B01J 10/00* | (2006.01) |
| *C07C 51/04* | (2006.01) |
| *C07C 59/08* | (2006.01) |
| *C07C 67/31* | (2006.01) |
| *C07C 45/72* | (2006.01) |
| *A61B 90/00* | (2016.01) |
| *A61B 18/18* | (2006.01) |
| *A61N 5/06* | (2006.01) |

(52) U.S. Cl.
CPC ............ *C07C 51/377* (2013.01); *B01J 10/00* (2013.01); *B01J 27/1802* (2013.01); *C07C 45/66* (2013.01); *C07C 45/72* (2013.01); *C07C 51/04* (2013.01); *C07C 59/08* (2013.01); *C07C 67/31* (2013.01); *A61B 18/18* (2013.01); *A61B 2090/0814* (2016.02); *A61N 2005/0644* (2013.01); *B01J 2219/02* (2013.01); *B01J 2219/0204* (2013.01); *B01J 2219/0245* (2013.01)

(58) Field of Classification Search
CPC ... B01J 10/00; B01J 27/1802; B01L 2219/02; B01L 2219/0204; B01L 2219/0245; C07C 51/377; C07C 45/66; C07C 59/08
See application file for complete search history.

(56) References Cited

U.S. PATENT DOCUMENTS

| | | | |
|---|---|---|---|
| 2013/0274517 A1* | 10/2013 | Godlewski | C07C 51/377 562/599 |
| 2015/0305091 A1* | 10/2015 | Hattendorf | H05B 3/12 219/426 |
| 2016/0032447 A1* | 2/2016 | Chiang | C23C 14/352 204/192.15 |

OTHER PUBLICATIONS

Gunter et al., "Formation of 2,3-Pentanedione from Lactic Acid over Supported Phosphate Catalysts", Journal of Catalysis, 148, 252-260, 1994.

* cited by examiner

*Primary Examiner* — Yate' K Cutliff
(74) *Attorney, Agent, or Firm* — James E Oehlenschlager

(57) ABSTRACT

Methods for making acrylic acid, acrylic acid derivatives, or mixtures thereof by contacting a stream containing hydroxypropionic acid, hydroxypropionic acid derivatives, or mixtures thereof with either an active catalyst containing an amorphous and partially-dehydrated phosphate salt or a precursor catalyst containing a crystalline phosphate salt in a reactor with a low corrosion rate are provided.

3 Claims, 2 Drawing Sheets

METHOD OF MAKING ACRYLIC ACID FROM HYDROXYPROPIONIC ACID

FIELD OF THE INVENTION

The present invention generally relates to methods of making acrylic acid, acrylic acid derivatives, or mixtures thereof by contacting a gas feed stream of water vapor and hydroxypropionic acid, hydroxypropionic acid derivatives, or mixtures thereof with a catalyst in a reactor. Specifically, the present invention relates to the use of a catalyst containing an amorphous and partially-dehydrated phosphate salt, and the reactor is a single-layer reactor that contains aluminum, silicon, or mixtures thereof and has a low corrosion rate. Alternatively, the reactor is a bi-layer reactor that has an inner layer and an outer layer, whereas the inner layer contains aluminum, and has a low corrosion rate.

BACKGROUND OF THE INVENTION

Acrylic acid, acrylic acid derivatives, or mixtures thereof are used today in a variety of industrial materials, such as adhesives, binders, coatings, paints, polishes, detergents, flocculants, dispersants, thixotropic agents, sequestrants, and superabsorbent polymers (SAP), which are used in disposable absorbent articles, including diapers and hygienic products. In terms of production process, acrylic acid is typically made today from the two-step catalytic oxidation of propylene, which in turn is produced from fossil resources, such as petroleum or natural gas. More on the oxidation of propylene to make acrylic acid and other production methods can be found in the Kirk-Othmer Encyclopedia of Chemical Technology, Vol. 1, pgs. 342-369 (5$^{th}$ Ed., John Wiley & Sons, Inc., 2004).

Fossil-derived acrylic acid contributes to greenhouse emissions due to its high content of fossil-derived carbon. Furthermore, the fossil resources are non-renewable, as it takes hundreds of thousands of years to form naturally and only a short time to consume. On the other hand, renewable resources refer to materials that are produced via a natural process at a rate comparable to their rate of consumption (e.g., within a 100-year time frame) and can be replenished naturally or via agricultural techniques. Examples of renewable resources include plants, such as sugar cane, sugar beets, corn, potatoes, citrus fruit, woody plants, lignocellulose, carbohydrate, hemicellulose, cellulosic waste, animals, fish, bacteria, fungi, and forestry products. As fossil resources become increasingly scarce, more expensive, and potentially subject to regulations for $CO_2$ emissions, there exists a growing need for non-fossil-derived acrylic acid, acrylic acid derivatives, or mixtures thereof that can serve as an alternative to fossil-derived acrylic acid, acrylic acid derivatives, or mixtures thereof.

Many attempts have been made over the last 80 years to make non-fossil-derived acrylic acid, acrylic acid derivatives, or mixtures thereof from renewable resources, such as lactic acid (also known as 2-hydroxypropionic acid), lactic acid derivatives (e.g. alkyl 2-acetoxy-propionate and 2-acetoxy propionic acid), 3-hydroxypropionic acid, glycerin, carbon monoxide and ethylene oxide, carbon dioxide and ethylene, and crotonic acid. From these resources, only lactic acid is produced today in high yield and purity from sugar ($\geq$90% of theoretical yield, or equivalently, $\geq$0.9 g of lactic acid per g of sugar), and with economics which could support producing acrylic acid cost competitively to fossil-derived acrylic acid. As such, lactic acid or lactate presents a real opportunity of serving as a feedstock for bio-based acrylic acid, acrylic acid derivatives, or mixtures thereof. Also, 3-hydroxypropionic acid is expected to be produced at commercial scale in a few years, and as such, 3-hydropropionic acid will present another real opportunity of serving as feedstock for bio-based acrylic acid, acrylic acid derivatives, or mixtures thereof. Sulfate salts; phosphate salts; mixtures of sulfate and phosphate salts; bases; zeolites or modified zeolites; metal oxides or modified metal oxides; and supercritical water are the main catalysts which have been used to dehydrate lactic acid or lactate to acrylic acid, acrylic acid derivatives, or mixtures thereof in the past with varying success.

For example, U.S. Pat. No. 4,786,756 (issued in 1988), describes the vapor phase dehydration of lactic acid or ammonium lactate to acrylic acid using aluminum phosphate ($AlPO_4$) treated with an aqueous inorganic base as a catalyst in a Pyrex reactor. The '756 patent discloses a maximum yield of acrylic acid of 43.3% when lactic acid was fed into the reactor at approximately atmospheric pressure, and a respective yield of 61.1% when ammonium lactate was fed into the reactor. In both examples, acetaldehyde was produced at yields of 34.7% and 11.9%, respectively, and other side products were also present in large quantities, such as propionic acid, CO, and $CO_2$. Omission of the base treatment caused increased amounts of the side products. Another example is Hong et al., Appl. Catal. A: General 396:194-200 (2011), who developed and tested composite catalysts made with $Ca_3(PO_4)_2$ and $Ca_2(P_2O_7)$ salts with a slurry-mixing method. The catalyst with the highest yield of acrylic acid from methyl lactate was the 50%-50% (by weight) catalyst. It yielded 68% acrylic acid, about 5% methyl acrylate, and about 14% acetaldehyde at 390° C. in a Pyrex reactor. When the feed changed from methyl lactate to lactic acid, the same catalyst achieved 54% yield of acrylic acid, 14% yield of acetaldehyde, and 14% yield of propionic acid. Prof. D. Miller's group at Michigan State University (MSU) published many papers on the dehydration of lactic acid or lactic acid esters to acrylic acid and 2,3-pentanedione, such as Gunter et al., J. Catalysis 148: 252-260 (1994); and Tam et al., Ind. Eng. Chem. Res. 38:3873-3877 (1999). The best acrylic acid yields reported by the group were about 33% when lactic acid was dehydrated at 350° C. over low surface area and pore volume silica impregnated with NaOH in a Pyrex reactor. In the same experiment, the acetaldehyde yield was 14.7% and the propionic acid yield was 4.1%. Examples of other catalysts tested by the group were $Na_2SO_4$, NaCl, $Na_3PO_4$, $NaNO_3$, $Na_2SiO_3$, $Na_4P_2O_7$, $NaH_2PO_4$, $Na_2HPO_4$, $Na_2HAsO_4$, $NaC_3H_5O_3$, NaOH, CsCl, $Cs_2SO_4$, KOH, CsOH, and LiOH. In all cases, the above referenced catalysts were tested as individual components, not in mixtures. Finally, the group suggested that the yield to acrylic acid is improved and the yield to the side products is suppressed when the surface area of the silica support is low, reaction temperature is high, reaction pressure is low, and residence time of the reactants in the catalyst bed is short. Finally, the Chinese patent application 200910054519.7 discloses the use of ZSM-5 molecular sieves modified with aqueous alkali (such as $NH_3$, NaOH, and $Na_2CO_3$) or a phosphoric acid salt (such as $NaH_2PO_4$, $Na_2HPO_4$, $LiH_2PO_4$, $LaPO_4$, etc.). The best yield of acrylic acid achieved in the dehydration of lactic acid was 83.9%, however that yield was achieved at very long residence times.

Therefore, the manufacture of acrylic acid, acrylic acid derivatives, or mixtures thereof from lactic acid or lactate by processes, such as those described in the literature noted above, has demonstrated: 1) yields of acrylic acid, acrylic acid derivatives, or mixtures thereof not exceeding 70% at short residence times; 2) low selectivities of acrylic acid, acrylic acid derivatives, or mixtures thereof, i.e., significant amounts of undesired side products, such as acetaldehyde, 2,3-pentanedione, propionic acid, CO, and $CO_2$; 3) long residence times in the catalyst beds; 4) catalyst deactivation in short time on stream (TOS); and 5) operations in Pyrex reactors. The side products can deposit onto the catalyst resulting in fouling, and premature and rapid deactivation of the catalyst. Further, once deposited, these side products can catalyze other undesired reactions, such as polymerization reactions. Aside from depositing on the catalysts, these side products, even when present in only small amounts, impose additional costs in processing acrylic acid (when present in the reaction product effluent) in the manufacture of SAP, for example. These deficiencies of the prior art processes and catalysts render them commercially non-viable.

Accordingly, there is a need for methods of making acrylic acid, acrylic acid derivatives or mixtures thereof from hydroxypropionic acid, hydroxypropionic acid derivatives, or mixtures thereof with high yield, selectivity, and efficiency (i.e., short residence time); high longevity catalysts; and in industrially-relevant reactors with low corrosion rates.

SUMMARY OF THE INVENTION

In one embodiment of the present invention, a method of making acrylic acid, acrylic acid derivatives, or mixtures thereof is provided. The method comprises contacting a gas feed stream comprising water vapor and hydroxypropionic acid, hydroxypropionic acid derivatives, or mixtures thereof with a catalyst in a single-layer reactor at a temperature, a water partial pressure, a Gas Hourly Space Velocity (GHSV), and a Weight Hourly Space Velocity (WHSV) to dehydrate said hydroxypropionic acid, hydroxypropionic acid derivatives, or mixtures thereof, resulting in the production of acrylic acid, acrylic acid derivatives, or mixtures thereof; wherein said catalyst comprises a phosphate salt comprising a cation and an anion represented by the empirical formula $[H_{2(1-x)}PO_{(4-x)}]^-$; wherein x is any real number greater than or equal to 0 and less than or equal to 1; wherein said water partial pressure is equal to or greater than about 0.4 bar; wherein said single-layer reactor comprises a wall, an outer surface, and an inner surface; wherein said wall is made from a wall material, has a wall thickness, and extends from said outer surface to said inner surface; wherein said wall material comprises aluminum in an amount between about 1 wt % and about 50 wt %; wherein said inner surface is in contact with said catalyst; and wherein said single-layer reactor has a corrosion rate lower than about 1.3 millimeters per year (mm/y) during said dehydration.

In another embodiment of the present invention, a method of making acrylic acid, acrylic acid derivatives, or mixtures thereof is provided. The method comprises contacting a gas feed stream comprising water vapor and hydroxypropionic acid, hydroxypropionic acid derivatives, or mixtures thereof with a catalyst in a single-layer reactor at a temperature, a water partial pressure, a GHSV, and a WHSV to dehydrate said hydroxypropionic acid, hydroxypropionic acid derivatives, or mixtures thereof, resulting in the production of acrylic acid, acrylic acid derivatives, or mixtures thereof; wherein said catalyst comprises a phosphate salt comprising a cation and an anion represented by the empirical formula $[H_{2(1-x)}PO_{(4-x)}]^-$; wherein x is any real number greater than or equal to 0 and less than or equal to 1; wherein said water partial pressure is equal to or greater than about 0.4 bar; wherein said single-layer reactor comprises a wall, an outer surface, and an inner surface; wherein said wall is made from a wall material, has a wall thickness, and extends from said outer surface to said inner surface; wherein said wall material comprises silicon in an amount between about 1 wt % and about 50 wt %; and wherein said inner surface is in contact with said catalyst; wherein said single-layer reactor has a corrosion rate lower than about 1.3 mm/y during said dehydration.

In yet another embodiment of the present invention, a method of making acrylic acid, acrylic acid derivatives, or mixtures thereof is provided. The method comprises contacting a gas feed stream comprising water vapor and hydroxypropionic acid, hydroxypropionic acid derivatives, or mixtures thereof with a catalyst in a bi-layer reactor at a temperature, a water partial pressure, a GHSV, and a WHSV to dehydrate said hydroxypropionic acid, hydroxypropionic acid derivatives, or mixtures thereof, resulting in the production of acrylic acid, acrylic acid derivatives, or mixtures thereof; wherein said catalyst comprises a phosphate salt comprising a cation and an anion represented by the empirical formula $[H_{2(1-x)}PO_{(4-x)}]^-$; wherein x is any real number greater than or equal to 0 and less than or equal to 1; wherein said water partial pressure is equal to or greater than about 0.4 bar; wherein said bi-layer reactor comprises an outer layer, an inner layer, an outer surface, an inner surface, and an interface between said outer layer and said inner layer; wherein said outer layer is made from an outer layer material, has an outer layer thickness, and extends from said interface to said outer surface; wherein said inner layer is made from an inner layer material, has an inner layer thickness, and extends from said inner surface to said interface; wherein said inner layer material is selected from the group consisting of aluminum, silicon, copper, silver, gold, titanium, tantalum, tungsten, molybdenum, platinum, palladium, zirconium, and mixtures thereof; wherein said inner surface is in contact with said catalyst; and wherein said bi-layer reactor has a corrosion rate lower than about 1.3 mm/y during said dehydration.

BRIEF DESCRIPTION OF THE DRAWING

While the specification concludes with claims particularly pointing out and distinctly claiming the invention, it is believed that the present invention will be better understood from the following description taken in conjunction with the accompanying drawings in which:

DETAILED DESCRIPTION OF THE INVENTION

I Definitions

Figure 1:
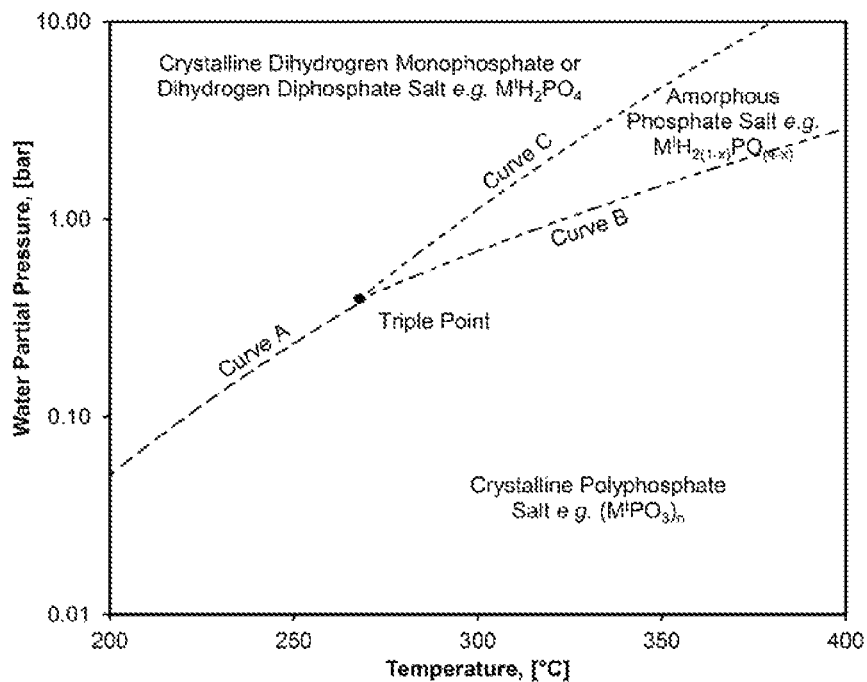
FIG. 1 is a typical water partial pressure versus temperature phase equilibrium diagram of an active dehydration catalyst (amorphous and partially-dehydrated phosphate salt) and a precursor dehydration catalyst (crystalline phosphate salt either fully-hydrated or fully-dehydrated). The triple point is located at the intersection of the three phase equilibrium curves. $M^1$ is a monovalent cation. Note that the reported values of the water partial pressure and temperature are for illustration purposes only.

As used herein, the term "fossil-derived" material refers to a material that is produced from fossil resources, such as crude oil (petroleum), natural gas, coal, peat, etc.

As used herein, the term "non-fossil-derived" material refers to a material that is produced from non-fossil resources. For clarity and for the purposes of the present invention, the terms "renewable" material, "bio-based" material, "non-petroleum" material, and "non-fossil-derived" material are used interchangeably.

As used herein, the term "renewable" material refers to a material that is produced from a renewable resource, which is a resource produced via a natural process at a rate comparable to its rate of consumption (e.g., within a 100 year time frame). The renewable resource can be replenished naturally or via agricultural techniques. Non-limiting examples of renewable resources include plants (such as sugar cane, beets, corn, potatoes, citrus fruit, woody plants, lignocellulose, hemicellulose, and cellulosic waste), animals, fish, bacteria, fungi, and forestry products. These resources can be naturally occurring, hybrids, or genetically engineered organisms. Fossil resources take longer than 100 years to form and thus they are not considered renewable resources.

As used herein, the term "renewable content" refers to the amount of carbon from a renewable resource in a material as a percent of the weight (mass) of the total organic carbon in the material, as determined by ASTM D6866-10 Method B.

As used herein, the term "catalyst" refers to either an active catalyst or precursor catalyst.

As used herein, the term "active catalyst" refers to the in-situ dehydration catalyst, which is the form of the catalyst present in the reactor during and responsible for the dehydration. The active catalyst of the present invention comprises an amorphous and partially-dehydrated phosphate salt with a cation and an anion represented by the empirical formula $[H_{2(1-x)}PO_{(4-x)}]^-$; wherein x is a real number greater than 0 and less than 1.

As used herein, the term "precursor catalyst" refers to the pre-reaction dehydration catalyst, which is the form of the catalyst loaded into the reactor and present in the reactor before the dehydration reaction starts or before a gas feed stream comprising water vapor at a water partial pressure and temperature above those of the triple point of the catalyst contacts the pre-reaction dehydration catalyst. The precursor catalyst converts to the active catalyst during the dehydration reaction or in the process conditions that can change its physical and chemical properties and become an active catalyst. The precursor catalyst of the present invention comprises a crystalline phosphate salt with a cation and an anion represented by the empirical formula $[H_{2(1-x)}PO_{(4-x)}]^-$; wherein x is 0 (phosphate salt is fully-hydrated and the anion is represented by the molecular formula $[H_2PO_4]^-$) or 1 (phosphate salt is fully-dehydrated and the anion is represented by the empirical formula $[PO_3]^-$).

As used herein, the term "condensed" refers to a crystalline and fully-dehydrated material.

As used herein, the term "triple point" refers to a point in the water partial pressure versus temperature phase equilibrium diagram of a catalyst, which is the intersection of the three phase boundary curves (also called, equilibrium lines) and where the 3 phases of the catalyst coexist in thermodynamic equilibrium: the $1^{st}$ phase equilibrium line separates the crystalline and fully-dehydrated phase from the crystalline and fully-hydrated phase of the catalyst; the $2^{nd}$ phase equilibrium line separates the crystalline and fully-dehydrated phase from the amorphous and partially-dehydrated phase of the catalyst; and the $3^{rd}$ phase equilibrium line separates the amorphous and partially-dehydrated phase from the crystalline and fully-hydrated phase of the catalyst (see FIG. 1).

As used herein, the term "triple point water partial pressure" refers to the water partial pressure at the triple point of the catalyst.

As used herein, the term "triple point temperature" refers to the temperature at the triple point of the catalyst.

As used herein, the term "phosphate salt" refers to a phosphate salt that is neutrally-charged.

As used herein, the term "monophosphate" or "orthophosphate" refers to any phosphate salt whose anion, $[PO_4]^{3-}$, is composed of four oxygen atoms arranged in an almost regular tetrahedral array about a central phosphorus atom.

As used herein, the term "condensed phosphate" refers to any phosphate salts containing one or several P—O—P bonds generated by corner sharing of $PO_4$ tetrahedra.

As used herein, the term "polyphosphate" refers to any condensed phosphate with a linear structure; i.e., containing linear P—O—P linkages by corner sharing of $PO_4$ tetrahedra leading to the formation of finite chains.

As used herein, the term "cyclophosphate" refers to any condensed phosphate with a cyclic structure.

As used herein, the term "hydrate" refers to a salt (i.e., salt.$nH_2O$) which has a number of water molecules (i.e., $nH_2O$) associated with the ions within its crystalline structure.

As used herein, the term "monovalent cation" refers to any cation with a positive charge of +1.

As used herein, the term "polyvalent cation" refers to any cation with a positive charge equal to or greater than +2.

As used herein, the term "heteropolyanion" refers to any anion with covalently bonded $XO_p$ and $YO_r$ polyhedra, and thus comprises X—O—Y and possibly X—O—X and Y—O—Y bonds; wherein X and Y represent any atoms, and wherein p and r are any positive integers.

As used herein, the term "heteropolyphosphate" refers to any heteropolyanion; wherein X represents phosphorus (P) and Y represents any other atom.

As used herein, the term "phosphate adduct" refers to any compound with one or more phosphate anions and one or more non-phosphate anions that are not covalently linked.

As used herein, the term "amorphous" refers to the state of a material that lacks the long-range order characteristic of a crystalline material. An amorphous material can be either an amorphous solid or a liquid. In the context of the present invention, materials with equal or more than 50 wt % of amorphous content are considered amorphous materials. The amorphous content of a material is determined by any method known to those skilled in the art, such as, by way of example and not limitation, x-ray diffraction (XRD), infrared spectroscopy (IR), Raman spectroscopy, differential scanning calorimetry (DSC), or solid-state nuclear magnetic resonance (NMR) spectroscopy. As an illustration, in a method based on an XRD technique, the separate crystalline ($I_C$) and amorphous ($I_A$) contributions to the X-ray scattering pattern are determined using a profile-fitting technique that deconvolutes the scattering pattern into the separate contributions using Gaussian, Lorentzian, Voigt, or related functions known to those skilled in the art. Then, the amorphous content, $X_A$, in wt % is determined by calculating the ratio between the area of scattered intensity for the amorphous contribution ($I_A$) and the area of the total scattered intensity (crystalline plus amorphous contributions, $I_T = I_C + I_A$) for a defined Bragg angle range (e.g. 2θ=5° to 50°, Cu-radiation λ=1.54059 Å, in the context of the current invention), $$\text{i.e., } X_A = \frac{I_A}{I_C + I_A} \times 100.$$

As used herein, the term "crystalline" refers to the state of a material whose constituents are arranged in a highly ordered microscopic structure forming a crystal lattice with long-range order. In the context of the present invention, materials with less than 50 wt % of amorphous content are considered crystalline materials.

As used herein, the term "chemically inert" material refers to a material which remains in the same chemical form, under equilibrium conditions, when contacted with another material or materials. In the context of the present invention, more than about 90 wt % of the material should remain in the same chemical form to be considered a "significantly chemically inert" material and more than about 98 wt % of the material should remain in the same chemical form to be considered an "essentially chemically inert" material.

As used herein, the term "antioxidant" refers to a molecule capable of terminating radical chain processes by either donating a hydrogen atom or the reaction of an olefinic bond to form a stabilized organic radical and thus terminate radical chain processes. Non-limiting examples of antioxidants comprise thiols, polyphenols, butylated hydroxy toluene (BHT), and butylated hydroxy anisole (BHA).

As used herein, the terms "LA" refers to lactic acid, "AA" refers to acrylic acid, "AcH" refers to acetaldehyde, and "PA" refers to propionic acid.

As used herein, the term "conversion" in mol % is defined as [hydroxypropionic acid, hydroxypropionic acid derivatives, or mixtures thereof flow rate in (mol/min)-hydroxypropionic acid, hydroxypropionic acid derivatives, or mixtures thereof flow rate out (mol/min)]/[hydroxypropionic acid, hydroxypropionic acid derivatives, or mixtures thereof flow rate in (mol/min)]×100.

As used herein, the term "yield" in mol % is defined as [product flow rate out (mol/min)/hydroxypropionic acid, hydroxypropionic acid derivatives, or mixtures thereof flow rate in (mol/min)]×100.

As used herein, the term "selectivity" in mol % is defined as [Yield/Conversion]×100.

As used herein, the term "total carbon balance" is defined as: [((mol carbon monoxide out+mol carbon dioxide out+mol methane out)+(2×(mol acetic acid out+mol acetaldehyde out+mol ethane out+mol ethylene out))+(3×(mol acrylic acid out+mol propionic acid out+mol hydroxypropionic acid out+mol hydroxyacetone out)+(5×mol 2,3 pentanedione out)+(6×mol acrylic acid dimer out))/(3×mol hydroxypropionic acid in)]×100. If hydroxypropionic acid derivative is used instead of hydroxypropionic acid, the above formula needs to be adjusted according to the number of carbon atoms in the hydroxypropionic acid derivative.

As used herein, the term "Gas Hourly Space Velocity" or "GHSV" in $h^{-1}$ is defined as 60×[Total gas flow rate (mL/min)/precursor catalyst empty bed volume (mL)]. The total gas flow rate is calculated under Standard Temperature and Pressure conditions (STP; 0° C. and 1 bar).

As used herein, the term "Weight Hourly Space Velocity" or "WHSV" in $h^{-1}$ is defined as 60×[Total LA flow rate (g/min)/precursor catalyst weight (g)]. For the purpose of this definition, the precursor catalyst weight includes only the weight of the crystalline phosphate salt and does not include the weight of any inert support.

As used herein, the term "Liquid Hourly Space Velocity" or "LHSV" in $h^{-1}$ is defined as 60×[Total liquid flow rate (mL/min)/precursor catalyst empty bed volume (mL)]. For the purpose of this definition, the precursor catalyst weight includes only the weight of the crystalline phosphate salt and does not include the weight of any inert support.

II Active Catalysts for the Dehydration of Hydroxypropionic Acid or its Derivatives to Acrylic Acid or its Derivatives Unexpectedly, it has been found that active catalysts comprising an amorphous and partially-dehydrated phosphate salt can dehydrate hydroxypropionic acid, hydroxypropionic acid derivatives, or mixtures thereof to acrylic acid, acrylic acid derivatives, or mixtures thereof with: 1) high yield and selectivity (i.e., low amount and few side products), and efficiency (i.e., short residence time); 2) high longevity catalysts; and 3) in industrially-relevant reactors with low corrosion rates. As a non-limiting example, the amorphous and partially-dehydrated phosphate salt can be formed reversibly when a crystalline phosphate salt (e.g. precursor catalyst with molar ratio of phosphorus to cations of about 1) is contacted with water vapor at water partial pressure and temperature above the triple point of the catalyst. The applicants also found unexpectedly, that in order to dehydrate hydroxypropionic acid, hydroxypropionic acid derivatives, or mixtures thereof to acrylic acid, acrylic acid derivatives, or mixtures thereof, the active catalyst of the present invention needs to be in the presence of sufficient water vapor, contrary to the common belief in the art that dehydration reactions have to be performed under dry conditions. Although not wishing to be bound by any theory, applicants hypothesize that the water vapor is required to avoid full dehydration of the dihydrogen monophosphate salt (which is fully-hydrated) to condensed phosphate (which is fully-dehydrated) under operating conditions, thus maintaining the Brønsted acid sites that are required for either the selective acid-catalyzed dehydration or phosphorylation and dephosphorylation of the hydroxypropionic acid and its derivatives to acrylic acid and its derivatives. The ability of some phosphate salts to undergo partial dehydration at some operating conditions is shown in FIG. 1, where a crystalline and fully-dehydrated polyphosphate salt $(M^I PO_3)_n$ becomes an amorphous and partially-dehydrated salt $M^I H_{2(1-x)} PO_{(4-x)}$ in a specific range of water partial pressure and temperature and then becomes crystalline again in the form of dihydrogen monophosphate $M^I H_2 PO_4$ as the water partial pressure increases further or the temperature decreases.

In one embodiment of the present invention, the active catalyst comprises a phosphate salt comprising a cation and an anion represented by the empirical formula $[H_{2(1-x)} PO_{(4-x)}]^-$; wherein x is any real number greater than 0 and less than 1. In another embodiment of the present invention, said phosphate salt is amorphous and partially-dehydrated.

In one embodiment of the present invention, the active catalyst comprises an amorphous and partially-dehydrated phosphate salt comprising a cation and an anion represented by the empirical formula $[H_{2(1-x)} PO_{(4-x)}]^-$; wherein x is any real number greater than 0 and less than 1. Non-limiting examples of cations in the phosphate salt are metallic cations, organo-metallic cations, ammonium, substituted ammonium, oxycations, and other cations known by those skilled in the art. Non-limiting examples of substituted ammonium and other cations are isopropylammonium, ethylenediammonium, sarcosinium, L-histidinium, glycinium, and 4-aminopyridinium. Non-limiting examples of oxycations are pervanadyl and vanadyl ions. In another embodiment of the present invention, said cation is a monovalent cation. Non-limiting examples of monovalent cations are cations of alkali metals, organo-metallic cations, ammonium, substituted ammonium, oxycations (e.g. pervanadyl), and other cations known by those skilled in the art. In yet another embodiment of the present invention, said monovalent cation is selected from the group consisting of $Li^+$, $Na^+$, $K^+$, $Rb^+$, $Cs^+$, $Ag^+$, $Tl^+$, and mixtures thereof. In even yet another embodiment of the present invention, said monovalent cation is selected from the group consisting of $K^+$, $Rb^+$, $Cs^+$, and mixtures thereof. In one embodiment of the present invention, said monovalent cation is selected from the group consisting of $K^+$, $Cs^+$, and mixtures thereof. In another embodiment of the present invention, said phosphate salt is amorphous and partially-dehydrated; wherein said x is any real number greater than 0 and less than 1; and wherein said cation is a monovalent cation selected from the group consisting of $K^+$, $Cs^+$, and mixtures thereof. In yet another embodiment of the present invention, said amorphous and partially-dehydrated phosphate salt is selected from the group consisting of $LiH_{2(1-x)}PO_{(4-x)}$, $NaH_{2(1-x)}PO_{(4-x)}$, $KH_{2(1-x)}PO_{(4-x)}$, $RbH_{2(1-x)}PO_{(4-x)}$, $CsH_{2(1-x)}PO_{(4-x)}$, any of their hydrate forms, and mixtures thereof; wherein x is any real number greater than 0 and less than 1. In even yet another embodiment of the present invention, said amorphous and partially-dehydrated phosphate salt is $KH_{2(1-x)}PO_{(4-x)}$; wherein x is any real number greater than 0 and less than 1. In one embodiment of the present invention, said amorphous and partially-dehydrated phosphate salt is $CsH_{2(1-x)}PO_{(4-x)}$; wherein x is any real number greater than 0 and less than 1.

In one embodiment of the present invention, the active catalyst comprises an amorphous and partially-dehydrated phosphate salt consisting of one or more cations, and one or more phosphate anions; wherein at least one phosphate anion is represented by the empirical formula $[H_{2(1-x)}PO_{(4-x)}]^-$, and wherein x is any real number greater than 0 and less than 1. For the purposes of the present invention, "one or more cations" refers to different types of cations. In another embodiment of the present invention, said cations are monovalent cations. In yet another embodiment of the present invention, said monovalent cations are selected from the group consisting of $Li^+$, $Na^+$, $K^+$, $Rb^+$, $Cs^+$, $Ag^+$, $Tl^+$, and mixtures thereof. In even yet another embodiment of the present invention, said monovalent cations are selected from the group consisting of $K^+$, $Rb^+$, $Cs^+$, and mixtures thereof. In one embodiment of the present invention, said monovalent cations are selected from the group consisting of $K^+$, $Cs^+$, and mixtures thereof.

In one embodiment of the present invention, the active catalyst comprises an amorphous and partially-dehydrated phosphate salt represented by the empirical formula $M^I{}_wN^I{}_{(1-w)}H_{2(1-x)}PO_{(4-x)}$; wherein $M^I$ and $N^I$ are two different monovalent cations; wherein x is any real number greater than 0 and less than 1; and wherein w is any real number greater than 0 and less than 1. In another embodiment of the present invention, the amorphous and partially-dehydrated phosphate salt is selected from the group consisting of $Li_wNa_{(1-w)}H_{2(1-x)}PO_{(4-x)}$, $Li_wK_{(1-w)}H_{2(1-x)}PO_{(4-x)}$, $Li_wRb_{(1-w)}H_{2(1-x)}PO_{(4-x)}$, $Li_wCs_{(1-w)}H_{2(1-x)}PO_{(4-x)}$, $Na_wK_{(1-w)}H_{2(1-x)}PO_{(4-x)}$, $Na_wRb_{(1-w)}H_{2(1-x)}PO_{(4-x)}$, $Na_wCs_{(1-w)}H_{2(1-x)}PO_{(4-x)}$, $K_wRb_{(1-w)}H_{2(1-x)}PO_{(4-x)}$, $K_wCs_{(1-w)}H_{2(1-x)}PO_{(4-x)}$, $Rb_wCs_{(1-w)}H_{2(1-x)}PO_{(4-x)}$, any of their hydrate forms, and mixtures thereof; wherein x is any real number greater than 0 and less than 1; and wherein w is any real number greater than 0 and less than 1.

In one embodiment of the present invention, the active catalyst comprising said amorphous and partially-dehydrated phosphate salt further comprises a non-phosphate compound; wherein said non-phosphate compound is significantly chemically inert to said amorphous and partially-dehydrated phosphate salt. In another embodiment of the present invention, the weight ratio of said amorphous and partially-dehydrated phosphate salt and said non-phosphate compound is between about 1:10 and about 4:1.

In one embodiment of the present invention, said non-phosphate compound comprises silicon oxide (also called silica; $SiO_2$). In another embodiment of the present invention, said non-phosphate compound consists essentially of silica. In yet another embodiment of the present invention, said silica is selected from the group consisting of amorphous silica (also called herein fused silica or fused quartz), quartz, tridymite, cristobalite, moganite, coesite, and mixtures thereof. In even yet another embodiment of the present invention, said silica is amorphous silica. In one embodiment of the present invention, said silica has a specific surface area of less than about 10 $m^2/g$.

In another embodiment of the present invention, said non-phosphate compound comprises a cation and an anion. Non-limiting examples of anions in the non-phosphate compounds are arsenates, condensed arsenates, nitrates, sulfates, condensed sulfates, borates, carbonates, chromates, condensed chromates, vanadates, niobates, tantalates, selenates, condensed silicates, condensed aluminates, germanates, condensed germanates, molybdates, condensed molybdates, other monomeric oxyanions, polyoxyanions, heteropolyphosphates, such as arsenatophosphates, phosphoaluminates, phosphoborates, phosphochromates, phosphomolybdates, phosphosilicates, phosphosulfates, phosphotungstates, and phosphate adducts, such as phosphate anions with telluric acid, halides, borates, carbonates, nitrates, sulfates, chromates, silicates, oxalates, mixtures thereof, or others that may be apparent to those having ordinary skill in the art.

In one embodiment of the present invention, said amorphous and partially-dehydrated phosphate salt is selected from the group consisting of $LiH_{2(1-x)}PO_{(4-x)}$, $NaH_{2(1-x)}PO_{(4-x)}$, $KH_{2(1-x)}PO_{(4-x)}$, $RbH_{2(1-x)}PO_{(4-x)}$, $CsH_{2(1-x)}PO_{(4-x)}$, any of their hydrate forms, and mixtures thereof; wherein x is any real number greater than 0 and less than 1, and wherein said non-phosphate compound is selected from the group consisting of amorphous silica, quartz, and mixtures thereof. In another embodiment of the present invention, said amorphous and partially-dehydrated phosphate salt is $KH_{2(1-x)}PO_{(4-x)}$; wherein x is any real number greater than 0 and less than 1, and wherein said non-phosphate compound is amorphous silica. In yet another embodiment of the present invention, said amorphous and partially-dehydrated phosphate salt is $CsH_{2(1-x)}PO_{(4-x)}$; wherein x is any real number greater than 0 and less than 1, and wherein said non-phosphate compound is amorphous silica.

In one embodiment of the present invention, said amorphous and partially-dehydrated phosphate salt is selected from the group consisting of $Li_wNa_{(1-w)}H_{2(1-x)}PO_{(4-x)}$, $Li_wK_{(1-w)}H_{2(1-x)}PO_{(4-x)}$, $Li_wRb_{(1-w)}H_{2(1-x)}PO_{(4-x)}$, $Li_wCs_{(1-w)}H_{2(1-x)}PO_{(4-x)}$, $Na_wK_{(1-w)}H_{2(1-x)}PO_{(4-x)}$, $Na_wRb_{(1-w)}H_{2(1-x)}PO_{(4-x)}$, $Na_wCs_{(1-w)}H_{2(1-x)}PO_{(4-x)}$, $K_wRb_{(1-w)}H_{2(1-x)}PO_{(4-x)}$, $K_wCs_{(1-w)}H_{2(1-x)}PO_{(4-x)}$, $Rb_wCs_{(1-w)}H_{2(1-x)}PO_{(4-x)}$, any of their hydrate forms, and mixtures thereof; wherein x is any real number greater than 0 and less than 1; wherein w is any real number greater than 0 and less than 1, and wherein said non-phosphate compound is selected from the group consisting of amorphous silica, quartz, and mixtures thereof.

In one embodiment of the present invention, said non-phosphate compound comprises a neutrally-charged oxysalt comprising a cation, and an oxyanion selected from the group represented by molecular formulae $[H_{(a-2b)}S_cO_{(4c-b)}]^{(2c-a)-}$ and $[Ta_{2d}O_{(5d+e)}]^{2e-}$; wherein a and b are positive integers or zero; wherein c, d, and e are positive integers; wherein (a-2b) is equal to or greater than zero; and wherein (2c-a) is greater than zero. In another embodiment of the present invention, said non-phosphate compound further comprises silica.

In one embodiment of the present invention, said cation of said oxysalt is selected from the group consisting of monovalent cation, polyvalent cation, and mixtures thereof. Non-limiting examples of said polyvalent cation of said oxysalt are cations of alkaline earth metals, transition metals, post-transition or poor metals, and metalloids; organometallic cations, substituted ammonium cations, oxycations (e.g. vanadyl), and other cations known by those skilled in the art. In another embodiment of the present invention, said polyvalent cation of said oxysalt is selected from the group consisting of the cations of the metals Be, Mg, Ca, Sr, Ba, Sc, Y, Ti, Zr, Hf, V, Nb, Ta, Cr, Mo, W, Mn, Re, Al, Ga, In, Tl, Si, Ge, Sn, Pb, Sb, Bi, La, Ce, Pr, Nd, Sm, Eu, Gd, Tb, Dy, Ho, Er, Tm, Yb, Lu, and mixtures thereof. In yet another embodiment of the present invention, said polyvalent cation of said oxysalt is selected from the group consisting of the cations of the metals Mg, Ca, Sr, Ba, Y, Mn, Al, Er, and mixtures thereof. In even yet another embodiment of the present invention, said polyvalent cation of said oxysalt is selected from the group consisting of divalent cations, trivalent cations, tetravalent cations, pentavalent cations, and mixtures thereof. In one embodiment of the present invention, said polyvalent cation of said oxysalt is selected from the group consisting of $Be^{2+}$, $Mg^{2+}$, $Ca^{2+}$, $Sr^{2+}$, $Ba^{2+}$, $Sc^{3+}$, $Y^{3+}$, $Ti^{3+}$, $Ti^{4+}$, $Zr^{2+}$, $Zr^{4+}$, $Hf^{4+}$, $V^{3+}$, $V^{4+}$, $Nb^{3+}$, $Cr^{2+}$, $Cr^{3+}$, $Mo^{3+}$, $Mo^{4+}$, $Mn^{2+}$, $Mn^{3+}$, $Re^{4+}$, $Al^{3+}$, $Ga^{3+}$, $In^{3+}$, $Si^{4+}$, $Ge^{4+}$, $Sn^{4+}$, $Pb^{4+}$, $Sb^{3+}$, $Sb^{5+}$, $Bi^{3+}$, $La^{3+}$, $Ce^{3+}$, $Ce^{4+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and mixtures thereof. In another embodiment of the present invention, said polyvalent cation of said oxysalt is selected from the group consisting of $Mg^{2+}$, $Ca^{2+}$, $Sr^{2+}$, $Ba^{2+}$, $Y^{3+}$, $Mn^{2+}$, $Mn^{3+}$, $Al^{3+}$, $Er^{3+}$, and mixtures thereof. In yet another embodiment of the present invention, said polyvalent cation of said oxysalt is $Ba^{2+}$.

Non-limiting examples of said monovalent cation of said oxysalt are cations of alkali metals. In one embodiment of the present invention, said monovalent cation of said oxysalt is selected from the group consisting of the cations of the metals Li, Na, K, Rb, Cs, Ag, Tl, and mixtures thereof. In another embodiment of the present invention, said monovalent cation of said oxysalt is selected from the group consisting of the cations of the metals K, Rb, Cs, and mixtures thereof.

In one embodiment of the present invention, said oxyanion of said oxysalt is selected from the group represented by molecular formulae $[SO_4]^{2-}$, $[S_2O_7]^{2-}$, $[HSO_4]^{1-}$, $[SO_4]^{2-}$, $[HSO_4]^-$, $[Ta_2O_6]^{2-}$, $[Ta_2O_7]^{4-}$, $[Ta_2O_9]^{8-}$, $[Ta_2O_{10}]^{10-}$, $[Ta_2O_{11}]^{12-}$, $[Ta_4O_{11}]^{2-}$, $[Ta_4O_{15}]^{10-}$, and mixtures thereof. In another embodiment of the present invention, said oxyanion of said oxysalt is selected from the group represented by molecular formulae $[SO_4]^{2-}$, $[Ta_2O_6]^{2-}$, and mixtures thereof.

Non-limiting examples of said oxysalt are sulfates of alkaline-earth metals, tantalates of alkaline-earth metals, sulfates of mixed alkali and alkaline earth metals, and tantalates of mixed alkali and alkaline earth metals. In one embodiment of the present invention, said oxysalt is selected from the group consisting of $CaSO_4$, $SrSO_4$, $BaSO_4$, $SrK_2(SO_4)_2$, $SrRb_2(SO_4)_2$, $Ca_2K_2(SO_4)_3$, $Ca_2Rb_2(SO_4)_3$, $Ca_2Cs_2(SO_4)_3$, $CaTa_4O_{11}$, $SrTa_4O_{11}$, $BaTa_4O_{11}$, $MgTa_2O_6$, $CaTa_2O_6$, $SrTa_2O_6$, $BaTa_2O_6$, $Mg_2Ta_2O_7$, $Ca_2Ta_2O_7$, $Sr_2Ta_2O_7$, $SrK_2Ta_2O_7$, $Ba_2Ta_2O_7$, $Ba_3Ta_2O_8$, $Mg_4Ta_2O_9$, $Ca_4Ta_2O_9$, $Sr_4Ta_2O_9$, $Ba_4Ta_2O_9$, $Ca_5Ta_2O_{10}$, $Ca_2KTa_3O_{10}$, $Ca_2RbTa_3O_{10}$, $Ca_2CsTa_3O_{10}$, $Sr_2KTa_3O_{10}$, $Sr_2RbTa_3O_{10}$, $Sr_2CsTa_3O_{10}$, $Mg_5Ta_4O_{15}$, $Sr_5Ta_4O_{15}$, $Ba_5Ta_4O_{15}$, $Sr_2KTa_5O_{15}$, $Ba_2KTa_5O_{15}$, $Sr_6Ta_2O_{11}$, $Ba_6Ta_2O_{11}$, any of their hydrate forms, and mixtures thereof. In another embodiment of the present invention, said oxysalt is selected from the group consisting of $CaSO_4$, $CaTa_2O_6$, $SrSO_4$, $SrTa_2O_6$, $BaSO_4$, $BaTa_2O_6$, any of their hydrate forms, and mixtures thereof. In yet another embodiment of the present invention, said oxysalt is selected from the group consisting of $BaSO_4$, $BaTa_2O_6$, any of their hydrate forms, and mixtures thereof.

In one embodiment of the present invention, said amorphous and partially-dehydrated phosphate salt is selected from the group consisting of $KH_{2(1-x)}PO_{(4-x)}$, $RbH_{2(1-x)}PO_{(4-x)}$, $CsH_{2(1-x)}PO_{(4-x)}$, any of their hydrate forms, and mixtures thereof; wherein x is any real number greater than 0 and less than 1; and wherein said non-phosphate compound is selected from the group consisting of $CaSO_4$, $CaTa_2O_6$, $SrSO_4$, $SrTa_2O_6$, $BaSO_4$, $BaTa_2O_6$, any of their hydrate forms, and mixtures thereof. In another embodiment of the present invention, said amorphous and partially-dehydrated phosphate salt is $KH_{2(1-x)}PO_{(4-x)}$; wherein x is any real number greater than 0 and less than 1; and wherein said non-phosphate compound is $BaSO_4$. In yet another embodiment of the present invention, said amorphous and partially-dehydrated phosphate salt is $CsH_{2(1-x)}PO_{(4-x)}$; wherein x is any real number greater than 0 and less than 1; and wherein said non-phosphate compound is $BaSO_4$.

In even yet another embodiment of the present invention, said amorphous and partially-dehydrated phosphate salt is selected from the group consisting of $K_wRb_{(1-w)}H_{2(1-x)}PO_{(4-x)}$, $K_wCs_{(1-w)}H_{2(1-x)}PO_{(4-x)}$, $Rb_wCs_{(1-w)}H_{2(1-x)}PO_{(4-x)}$, any of their hydrate forms, and mixtures thereof; wherein x is any real number greater than 0 and less than 1; wherein w is any real number greater than 0 and less than 1; and wherein said non-phosphate compound is selected from the group consisting of $CaSO_4$, $CaTa_2O_6$, $SrSO_4$, $SrTa_2O_6$, $BaSO_4$, $BaTa_2O_6$, any of their hydrate forms, and mixtures thereof.

In one embodiment of the present invention, said x is equal to about 0.8. In another embodiment of the present invention, said x is less than about 0.8. In yet another embodiment of the present invention, said x is less than about 0.6. In even yet another embodiment of the present invention, said x is less than about 0.5. In one embodiment of the present invention, said x is between about 0.1 and about 0.5. In another embodiment of the present invention, said x is between about 0.25 and about 0.45. In yet another embodiment of the present invention, said x is equal to about 0.4. In even yet another embodiment of the present invention, said x is equal to about 0.4 and said monovalent cation of said amorphous and partially-dehydrated phosphate salt is $Cs^+$.

In one embodiment of the present invention, said w is greater than about 0.9. In another embodiment of the present invention, said w is greater than about 0.8. In yet another embodiment of the present invention, said w is less than about 0.2. In even yet another embodiment of the present invention, said w is less than about 0.1.

In one embodiment of the present invention, said amorphous and partially-dehydrated phosphate salt is a hydrate salt. In another embodiment of the present invention, said oxysalt is a hydrate salt. In yet another embodiment of the present invention, said non-phosphate compound is a hydrate compound. A hydrate salt or compound contains a specific number of water molecules per formula unit of the salt or compound. Non-limiting examples of hydrate salts or compounds are hemihydrate, monohydrate, sesquihydrate, dihydrate, trihydrate, tetrahydrate, pentahydrate, hexahydrate, heptahydrate, octahydrate, nonahydrate, nonahydrate, and decahydrate salts or compounds.

In one embodiment of the present invention, said active catalyst further comprises an inert support. Non-limiting examples of inert supports are silica, silicate, alumina, aluminate, aluminosilicate, titania, titanate, zirconia, zirconate, carbon (such as activated carbon, diamond, graphite, or fullerenes), sulfate, phosphate, tantalate, ceria, other metal oxides, and mixtures thereof. In another embodiment of the present invention, said inert support consists essentially of silica. In yet another embodiment of the present invention, said silica is selected from the group consisting of amorphous silica, quartz, tridymite, cristobalite, moganite, coesite, and mixtures thereof. In even yet another embodiment of the present invention, said silica is amorphous silica. In one embodiment of the present invention, said silica has a specific surface area of less than about 10 m$^2$/g. In another embodiment of the present invention, the inert support represents an amount between about 20 wt % and about 90 wt %, based on the total weight of the active catalyst.

In one embodiment of the present invention, the weight of the amorphous and partially-dehydrated phosphate salt based on the total weight of the active catalyst is between about 5 wt % and about 90 wt %. In another embodiment of the present invention, the weight of the amorphous and partially-dehydrated phosphate salt based on the total weight of the active catalyst is between about 8 wt % and about 60 wt %. In yet another embodiment of the present invention, the weight of the amorphous and partially-dehydrated phosphate salt based on the total weight of the active catalyst is between about 12 wt % and about 40 wt %. In even yet another embodiment of the present invention, the weight of the amorphous and partially-dehydrated phosphate salt based on the total weight of the active catalyst is between about 12 wt % and about 17 wt %. In one embodiment of the present invention, the weight of the amorphous and partially-dehydrated phosphate salt based on the total weight of the active catalyst is between about 26 wt % and about 32 wt %.

In one embodiment of the present invention, the active catalyst consists of $CsH_{2(1-x)}PO_{(4-x)}$ and fused silica; wherein the weight of said $CsH_{2(1-x)}PO_{(4-x)}$ based on the total weight of the active catalyst is about 14 wt %, and wherein x is any real number greater than 0 and less than 1. In another embodiment of the present invention, the active catalyst consists of $CsH_{2(1-x)}PO_{(4-x)}$ and fused silica; wherein the weight of said $CsH_{2(1-x)}PO_{(4-x)}$ based on the total weight of the active catalyst is about 28 wt %, and wherein x is any real number greater than 0 and less than 1. In yet another embodiment of the present invention, the active catalyst consists of $KH_{2(1-x)}PO_{(4-x)}$ and fused silica; wherein the weight of said $KH_{2(1-x)}PO_{(4-x)}$ based on the total weight of the active catalyst is about 15 wt %, and wherein x is any real number greater than 0 and less than 1. In even yet another embodiment of the present invention, the active catalyst consists of $KH_{2(1-x)}PO_{(4-x)}$ and fused silica; wherein the weight of said $KH_{2(1-x)}PO_{(4-x)}$ based on the total weight of the active catalyst is about 30 wt %, and wherein x is any real number greater than 0 and less than 1. In one embodiment of the present invention, the active catalyst consists of $RbH_{2(1-x)}PO_{(4-x)}$ and fused silica; wherein the weight of said $RbH_{2(1-x)}PO_{(4-x)}$ based on the total weight of the active catalyst is about 14 wt %, and wherein x is any real number greater than 0 and less than 1. In another embodiment of the present invention, the active catalyst consists of $RbH_{2(1-x)}PO_{(4-x)}$ and fused silica; wherein the weight of said $RbH_{2(1-x)}PO_{(4-x)}$ based on the total weight of the active catalyst is about 29 wt %, and wherein x is any real number greater than 0 and less than 1.

The active catalyst of the present invention can be utilized to catalyze several chemical reactions. Non-limiting examples of reactions are: dehydration of lactic acid, lactic acid derivatives, or mixtures thereof to acrylic acid; dehydration of 3-hydroxypropionic acid, 3-hydroxypropionic acid derivatives, or mixtures thereof to acrylic acid; dehydration of glycerin to acrolein; isomerization of lactic acid to 3-hydroxypropionic acid in the presence of water; reduction of hydroxypropionic acid to propionic acid or 1-propanol in the presence of hydrogen gas; dehydration of aliphatic alcohols to alkenes or olefins; dehydrogenation of aliphatic alcohols to ethers; other dehydrogenations, hydrolyses, alkylations, dealkylations, oxidations, disproportionations, esterifications, cyclizations, isomerizations, condensations, aromatizations, polymerizations; and other reactions that may be apparent to those having ordinary skill in the art.

III Precursor Catalysts for the Dehydration of Hydroxypropionic Acid or its Derivatives to Acrylic Acid or its Derivatives In one embodiment of the present invention, the precursor catalyst comprises a phosphate salt consisting of one or more cations; wherein the ratio of the total moles of all cations and the total moles of phosphorus is about 1. In another embodiment of the present invention, said phosphate salt is selected from the group consisting of crystalline and fully-dehydrated phosphate salt, crystalline and fully-hydrated phosphate salt, and mixtures thereof.

In one embodiment of the present invention, the precursor catalyst comprises a phosphate salt comprising a cation and an anion represented by the empirical formula $[H_{2(1-x)}PO_{(4-x)}]^-$; wherein x is 0 or 1. In another embodiment of the present invention, said phosphate salt is crystalline.

In one embodiment of the present invention, the precursor catalyst comprises a crystalline phosphate salt comprising a cation and an anion represented by the empirical formula $[H_{2(1-x)}PO_{(4-x)}]^-$; wherein x is 0 or 1. Non-limiting examples of cations are metallic cations, organo-metallic cations, ammonium, substituted ammonium, oxycations, and other cations known by those skilled in the art. Non-limiting examples of substituted ammonium and other cations are isopropylammonium, ethylenediammonium, sarcosinium, L-histidinium, glycinium, and 4-aminopyridinium. Non-limiting examples of oxycations are pervanadyl and vanadyl ions. In another embodiment of the present invention, said cation is a monovalent cation. Non-limiting examples of monovalent cations are cations of alkali metals, organo-metallic cations, ammonium, substituted ammonium, oxycations (e.g. pervanadyl), and other cations known by those skilled in the art. In yet another embodiment of the present invention, said monovalent cation is selected from the group consisting of $Li^+$, $Na^+$, $K^+$, $Rb^+$, $Cs^+$, $Ag^+$, $Tl^+$, and mixtures thereof. In even yet another embodiment of the present invention, said monovalent cation is selected from the group consisting of $K^+$, $Rb^+$, $Cs^+$, and mixtures thereof. In one embodiment of the present invention, said monovalent cation is selected from the group consisting of $K^+$, $Cs^+$, and mixtures thereof. In another embodiment of the present invention, said phosphate salt is crystalline; wherein said x is 0 or 1; and wherein said cation is a monovalent cation selected from the group consisting of K+, Cs+, and mixtures thereof. In yet another embodiment of the present invention, said crystalline phosphate salt is selected from the group consisting of $LiH_{2(1-x)}PO_{(4-x)}$, $NaH_{2(1-x)}PO_{(4-x)}$, $KH_{2(1-x)}PO_{(4-x)}$, $RbH_{2(1-x)}PO_{(4-x)}$, $CsH_{2(1-x)}PO_{(4-x)}$, any of their hydrate forms, and mixtures thereof; wherein x is 0 or 1. In even yet another embodiment of the present invention, said crystalline phosphate salt is $KH_{2(1-x)}PO_{(4-x)}$; wherein x is 0 or 1. In one embodiment of the present invention, said crystalline phosphate salt is $CsH_{2(1-x)}PO_{(4-x)}$; wherein x is 0 or 1.

In one embodiment of the present invention, the precursor catalyst comprises a crystalline phosphate salt consisting of one or more cations, and one or more phosphate anions; wherein at least one phosphate anion is represented by the empirical formula $[H_{2(1-x)}PO_{(4-x)}]^-$; wherein x is 0 or 1. For the purposes of the present invention, "one or more cations" refers to different types of cations. In another embodiment of the present invention, said cations are monovalent cations. In yet another embodiment of the present invention, said monovalent cations are selected from the group consisting of $Li^+$, $Na^+$, $K^+$, $Rb^+$, $Cs^+$, $Ag^+$, $Tl^+$, and mixtures thereof. In even yet another embodiment of the present invention, said monovalent cations are selected from the group consisting of $K^+$, $Rb^+$, $Cs^+$, and mixtures thereof. In one embodiment of the present invention, said monovalent cations are selected from the group consisting of $K^+$, $Cs^+$, and mixtures thereof.

In one embodiment of the present invention, the precursor catalyst comprises a crystalline phosphate salt represented by the empirical formula $M_w^I N_{(1-w)}^I H_{2(1-x)} PO_{(4-x)}$; wherein $M^I$ and $N^I$ are two different monovalent cations; wherein x is 0 or 1; and wherein w is any real number greater than 0 and less than 1. In another embodiment of the present invention, the crystalline phosphate salt is selected from the group consisting of $Li_w Na_{(1-w)} H_{2(1-x)} PO_{(4-x)}$, $Li_w K_{(1-w)} H_{2(1-x)} PO_{(4-x)}$, $Li_w Rb_{(1-w)} H_{2(1-x)} PO_{(4-x)}$, $Li_w Cs_{(1-w)} H_{2(1-x)} PO_{(4-x)}$, $Na_w K_{(1-w)} H_{2(1-x)} PO_{(4-x)}$, $Na_w Rb_{(1-w)} H_{2(1-x)} PO_{(4-x)}$, $Na_w Cs_{(1-w)} H_{2(1-x)} PO_{(4-x)}$, $K_w Rb_{(1-w)} H_{2(1-x)} PO_{(4-x)}$, $K_w Cs_{(1-w)} H_{2(1-x)} PO_{(4-x)}$, $Rb_w Cs_{(1-w)} H_{2(1-x)} PO_{(4-x)}$, any of their hydrate forms, and mixtures thereof; wherein x is 0 or 1; and wherein w is any real number greater than 0 and less than 1.

In one embodiment of the present invention, the precursor catalyst comprising said crystalline phosphate salt further comprises a non-phosphate compound; wherein said non-phosphate compound is significantly chemically inert to said crystalline phosphate salt. In another embodiment of the present invention, the weight ratio of said crystalline phosphate salt and said non-phosphate compound is between about 1:10 and about 4:1.

In one embodiment of the present invention, said non-phosphate compound comprises silicon oxide (also, called silica; $SiO_2$). In another embodiment of the present invention, said non-phosphate compound consists essentially of silica. In yet another embodiment of the present invention, said silica is selected from the group consisting of amorphous silica (also called herein fused silica or fused quartz), quartz, tridymite, cristobalite, moganite, coesite, and mixtures thereof. In even yet another embodiment of the present invention, said silica is amorphous silica. In one embodiment of the present invention, said silica has a specific surface area of less than about 10 $m^2/g$.

In another embodiment of the present invention, said non-phosphate compound comprises an anion and a cation. Non-limiting examples of anions in the non-phosphate compounds are arsenates, condensed arsenates, nitrates, sulfates, condensed sulfates, borates, carbonates, chromates, condensed chromates, vanadates, niobates, tantalates, selenates, condensed silicates, condensed aluminates, germanates, condensed germanates, molybdates, condensed molybdates, other monomeric oxyanions, polyoxyanions, heteropolyphosphates, such as arsenatophosphates, phosphoaluminates, phosphoborates, phosphochromates, phosphomolybdates, phosphosilicates, phosphosulfates, phosphotungstates, and phosphate adducts, such as phosphate anions with telluric acid, halides, borates, carbonates, nitrates, sulfates, chromates, silicates, oxalates, mixtures thereof, or others that may be apparent to those having ordinary skill in the art.

In one embodiment of the present invention, said crystalline phosphate salt is selected from the group consisting of $LiH_{2(1-x)}PO_{(4-x)}$, $NaH_{2(1-x)}PO_{(4-x)}$, $KH_{2(1-x)}PO_{(4-x)}$, $RbH_{2(1-x)}PO_{(4-x)}$, $CsH_{2(1-x)}PO_{(4-x)}$, any of their hydrate forms, and mixtures thereof; wherein x is 0 or 1; and wherein said non-phosphate compound is selected from the group consisting of amorphous silica, quartz, and mixtures thereof. In another embodiment of the present invention, said crystalline phosphate salt is $KH_{2(1-x)}PO_{(4-x)}$; wherein x is 0 or 1; and wherein said non-phosphate compound is amorphous silica. In yet another embodiment of the present invention, said crystalline phosphate salt is $CsH_{2(1-x)}PO_{(4-x)}$; wherein x is 0 or 1; and wherein said non-phosphate compound is amorphous silica.

In one embodiment of the present invention, said crystalline phosphate salt is selected from the group consisting of $Li_w Na_{(1-w)} H_{2(1-x)} PO_{(4-x)}$, $Li_w K_{(1-w)} H_{2(1-x)} PO_{(4-x)}$, $Li_w Rb_{(1-w)} H_{2(1-x)} PO_{(4-x)}$, $Li_w Cs_{(1-w)} H_{2(1-x)} PO_{(4-x)}$, $Na_w K_{(1-w)} H_{2(1-x)} PO_{(4-x)}$, $Na_w Rb_{(1-w)} H_{2(1-x)} PO_{(4-x)}$, $Na_w Cs_{(1-w)} H_{2(1-x)} PO_{(4-x)}$, $K_w Rb_{(1-w)} H_{2(1-x)} PO_{(4-x)}$, $K_w Cs_{(1-w)} H_{2(1-x)} PO_{(4-x)}$, $Rb_w Cs_{(1-w)} H_{2(1-x)} PO_{(4-x)}$, any of their hydrate forms, and mixtures thereof; wherein x is 0 or 1; wherein w is any real number greater than 0 and less than 1; and wherein said non-phosphate compound is selected from the group consisting of amorphous silica, quartz, and mixtures thereof.

In one embodiment of the present invention, said non-phosphate compound comprises a neutrally-charged oxysalt comprising a cation, and an oxyanion selected from the group represented by molecular formulae $[H_{(a-2b)}S_c O_{(4c-b)}]^{(2c-a)-}$ and $[Ta_{2d}O_{(5d+e)}]^{2e-}$; wherein a and b are positive integers or zero; wherein c, d, and e are positive integers; wherein (a-2b) is equal to or greater than zero; and wherein (2c-a) is greater than zero. In another embodiment of the present invention, said non-phosphate compound further comprises silica.

In one embodiment of the present invention, said cation of said oxysalt is selected from the group consisting of monovalent cation, polyvalent cation, and mixtures thereof. Non-limiting examples of said polyvalent cation of said oxysalt are cations of alkaline earth metals, transition metals, post-transition or poor metals, and metalloids; organometallic cations, substituted ammonium cations, oxycations (e.g. vanadyl), and other cations known by those skilled in the art. In another embodiment of the present invention, said polyvalent cation of said oxysalt is selected from the group consisting of the cations of the metals Be, Mg, Ca, Sr, Ba, Sc, Y, Ti, Zr, Hf, V, Nb, Ta, Cr, Mo, W, Mn, Re, Al, Ga, In, Tl, Si, Ge, Sn, Pb, Sb, Bi, La, Ce, Pr, Nd, Sm, Eu, Gd, Tb, Dy, Ho, Er, Tm, Yb, Lu, and mixtures thereof. In yet another embodiment of the present invention, said polyvalent cation of said oxysalt is selected from the group consisting of the cations of the metals Mg, Ca, Sr, Ba, Y, Mn, Al, Er, and mixtures thereof. In even yet another embodiment of the present invention, said polyvalent cation of said oxysalt is selected from the group consisting of divalent cations, trivalent cations, tetravalent cations, pentavalent cations, and mixtures thereof. In one embodiment of the present invention, said polyvalent cation of said oxysalt is selected from the group consisting of $Be^{2+}$, $Mg^{2+}$, $Ca^{2+}$, $Sr^{2+}$, $Ba^{2+}$, $Sc^{3+}$, $Y^{3+}$, $Ti^{3+}$, $Ti^{4+}$, $Zr^{2+}$, $Zr^{4+}$, $Hf^{4+}$, $V^{3+}$, $V^{4+}$, $Nb^{3+}$, $Cr^{2+}$, $Cr^{3+}$, $Mo^{3+}$, $Mo^{4+}$, $Mn^{2+}$, $Mn^{3+}$, $Re^{4+}$, $Al^{3+}$, $Ga^{3+}$, $In^{3+}$, $Si^{4+}$, $Ge^{4+}$, $Sn^{4+}$, $Pb^{4+}$, $Sb^{3+}$, $Sb^{5+}$, $Bi^{3+}$, $La^{3+}$, $Ce^{3+}$, $Ce^{4+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and mixtures thereof. In another embodiment of the present invention, said polyvalent cation of said oxysalt is selected from the group consisting of $Mg^{2+}$, $Ca^{2+}$, $Sr^{2+}$, $Ba^{2+}$, $Y^{3+}$, $Mn^{2+}$, $Mn^{3+}$, $Al^{3+}$, $Er^{3+}$, and mixtures thereof. In yet another embodiment of the present invention, said polyvalent cation of said oxysalt is $Ba^{2+}$.

Non-limiting examples of said monovalent cation of said oxysalt are cations of alkali metals. In one embodiment of the present invention, said monovalent cation of said oxysalt is selected from the group consisting of the cations of the metals Li, Na, K, Rb, Cs, Ag, Tl, and mixtures thereof. In another embodiment of the present invention, said monovalent cation of said oxysalt is selected from the group consisting of the cations of the metals K, Rb, Cs, and mixtures thereof.

In one embodiment of the present invention, said oxyanion of said oxysalt is selected from the group represented by molecular formulae $[SO_4]^{2-}$, $[S_2O_7]^{2-}$, $[HSO_4]^{1-}$, $[SO_4]^{2-}$, $[HSO_4]^-$, $[Ta_2O_6]^{2-}$, $[Ta_2O_7]^{4-}$, $[Ta_2O_9]^{8-}$, $[Ta_2O_{10}]^{10-}$, $[Ta_2O_{11}]^{12-}$, $[Ta_4O_{11}]^{2-}$, $[Ta_4O_{15}]^{10-}$, and mixtures thereof. In another embodiment of the present invention, said oxyanion of said oxysalt is selected from the group represented by molecular formulae $[SO_4]^{2-}$, $[Ta_2O_6]^{2-}$, and mixtures thereof.

Non-limiting examples of said oxysalt are sulfates of alkaline-earth metals, tantalates of alkaline-earth metals, sulfates of mixed alkali and alkaline earth metals, and tantalates of mixed alkali and alkaline earth metals. In one embodiment of the present invention, said oxysalt is selected from the group consisting of $CaSO_4$, $SrSO_4$, $BaSO_4$, $SrK_2(SO_4)_2$, $SrRb_2(SO_4)_2$, $Ca_2K_2(SO_4)_3$, $Ca_2Rb_2(SO_4)_3$, $Ca_2Cs_2(SO_4)_3$, $CaTa_4O_{11}$, $SrTa_4O_{11}$, $BaTa_4O_{11}$, $MgTa_2O_6$, $CaTa_2O_6$, $SrTa_2O_6$, $BaTa_2O_6$, $Mg_2Ta_2O_7$, $Ca_2Ta_2O_7$, $Sr_2Ta_2O_7$, $SrK_2Ta_2O_7$, $Ba_2Ta_2O_7$, $Ba_3Ta_2O_8$, $Mg_4Ta_2O_9$, $Ca_4Ta_2O_9$, $Sr_4Ta_2O_9$, $Ba_4Ta_2O_9$, $Ca_5Ta_2O_{10}$, $Ca_2KTa_3O_{10}$, $Ca_2RbTa_3O_{10}$, $Ca_2CsTa_3O_{10}$, $Sr_2KTa_3O_{10}$, $Sr_2RbTa_3O_{10}$, $Sr_2CsTa_3O_{10}$, $Mg_5Ta_4O_{15}$, $Sr_5Ta_4O_{15}$, $Ba_5Ta_4O_{15}$, $Sr_2KTa_5O_{15}$, $Ba_2KTa_5O_{15}$, $Sr_6Ta_2O_{11}$, $Ba_6Ta_2O_{11}$, any of their hydrate forms, and mixtures thereof. In another embodiment of the present invention, said oxysalt is selected from the group consisting of $CaSO_4$, $CaTa_2O_6$, $SrSO_4$, $SrTa_2O_6$, $BaSO_4$, $BaTa_2O_6$, any of their hydrate forms, and mixtures thereof. In yet another embodiment of the present invention, said oxysalt is selected from the group consisting of $BaSO_4$, $BaTa_2O_6$, any of their hydrate forms, and mixtures thereof.

In one embodiment of the present invention, said crystalline phosphate salt is selected from the group consisting of $KH_{2(1-x)}PO_{(4-x)}$, $RbH_{2(1-x)}PO_{(4-x)}$, $CsH_{2(1-x)}PO_{(4-x)}$, any of their hydrate forms, and mixtures thereof; wherein x is 0 or 1; and wherein said non-phosphate compound is selected from the group consisting of $CaSO_4$, $CaTa_2O_6$, $SrSO_4$, $SrTa_2O_6$, $BaSO_4$, $BaTa_2O_6$, any of their hydrate forms, and mixtures thereof. In another embodiment of the present invention, said crystalline phosphate salt is $KH_{2(1-x)}PO_{(4-x)}$; wherein x is 0 or 1; and wherein said non-phosphate compound is $BaSO_4$. In yet another embodiment of the present invention, said crystalline phosphate salt is $CsH_{2(1-x)}PO_{(4-x)}$; wherein x is 0 or 1; and wherein said non-phosphate compound is $BaSO_4$.

In even yet another embodiment of the present invention, said crystalline phosphate salt is selected from the group consisting of $K_wRb_{(1-w)}H_{2(1-x)}PO_{(4-x)}$, $K_wCs_{(1-w)}H_{2(1-x)}PO_{(4-x)}$, $Rb_wCs_{(1-w)}H_{2(1-x)}PO_{(4-x)}$, any of their hydrate forms, and mixtures thereof; wherein x is 0 or 1; wherein w is any real number greater than 0 and less than 1; and wherein said non-phosphate compound is selected from the group consisting of $CaSO_4$, $CaTa_2O_6$, $SrSO_4$, $SrTa_2O_6$, $BaSO_4$, $BaTa_2O_6$, any of their hydrate forms, and mixtures thereof.

In one embodiment of the present invention, said w is greater than about 0.9. In another embodiment of the present invention, said w is greater than about 0.8. In yet another embodiment of the present invention, said w is less than about 0.2. In even yet another embodiment of the present invention, said w is less than about 0.1.

In one embodiment of the present invention, said crystalline phosphate salt is a hydrate salt. In another embodiment of the present invention, said oxysalt is a hydrate salt. In another embodiment of the present invention, said non-phosphate compound is a hydrate compound. A hydrate salt or compound contains a specific number of water molecules per formula unit of the salt or compound. Non-limiting examples of hydrate salts or compounds are hemihydrate, monohydrate, sesquihydrate, dihydrate, trihydrate, tetrahydrate, pentahydrate, hexahydrate, heptahydrate, octahydrate, nonahydrate, nonahydrate, and decahydrate salts or compounds.

In one embodiment of the present invention, said precursor catalyst further comprises an inert support. Non-limiting examples of inert supports are silica, silicate, alumina, aluminate, aluminosilicate, titania, titanate, zirconia, zirconate, carbon (such as activated carbon, diamond, graphite, or fullerenes), sulfate, phosphate, tantalate, ceria, other metal oxides, and mixtures thereof. In another embodiment of the present invention, said inert support consists essentially of silica. In yet another embodiment of the present invention, said silica is selected from the group consisting of amorphous silica, quartz, tridymite, cristobalite, moganite, coesite, and mixtures thereof. In even another embodiment of the present invention, said silica is amorphous silica. In one embodiment of the present invention, said silica has a specific surface area of less than about 10 $m^2/g$. In another embodiment of the present invention, the inert support represents an amount between about 20 wt % and about 90 wt %, based on the total weight of the precursor catalyst.

In one embodiment of the present invention, the weight of the crystalline phosphate salt based on the total weight of the precursor catalyst is between about 5 wt % and about 90 wt %. In another embodiment of the present invention, the weight of the crystalline phosphate salt based on the total weight of the precursor catalyst is between about 8 wt % and about 60 wt %. In yet another embodiment of the present invention, the weight of the crystalline phosphate salt based on the total weight of the precursor catalyst is between about 12 wt % and about 40 wt %. In even yet another embodiment of the present invention, the weight of the crystalline phosphate salt based on the total weight of the precursor catalyst is between about 12 wt % and about 17 wt %. In one embodiment of the present invention, the weight of the crystalline phosphate salt based on the total weight of the precursor catalyst is between about 26 wt % and about 32 wt %.

In one embodiment of the present invention, the precursor catalyst consists of $CsPO_3$ and fused silica; wherein the weight of said $CsPO_3$ based on the total weight of the precursor catalyst is about 13 wt %. In another embodiment of the present invention, the precursor catalyst consists of $CsPO_3$ and fused silica; wherein the weight of said $CsPO_3$ based on the total weight of the precursor catalyst is about 26 wt %. In yet another embodiment of the present invention, the precursor catalyst consists of $KPO_3$ and fused silica; wherein the weight of said $KPO_3$ based on the total weight of the precursor catalyst is about 13 wt %. In even yet another embodiment of the present invention, the precursor catalyst consists of $KPO_3$ and fused silica; wherein the weight of said $KPO_3$ based on the total weight of the precursor catalyst is about 26 wt %. In one embodiment of the present invention, the precursor catalyst consists of $RbPO_3$ and fused silica; wherein the weight of said $RbPO_3$ based on the total weight of the precursor catalyst is about 13 wt %. In another embodiment of the present invention, the precursor catalyst consists of $RbPO_3$ and fused silica; wherein the weight of said $RbPO_3$ based on the total weight of the precursor catalyst is about 26 wt %.

In one embodiment of the present invention, the precursor catalyst consists of $CsH_2PO_4$ and fused silica; wherein the weight of said $CsH_2PO_4$ based on the total weight of the precursor catalyst is about 14 wt %. In another embodiment of the present invention, the precursor catalyst consists of $CsH_2PO_4$ and fused silica; wherein the weight of said $CsH_2PO_4$ based on the total weight of the precursor catalyst is about 28 wt %. In yet another embodiment of the present invention, the precursor catalyst consists of $KH_2PO_4$ and fused silica; wherein the weight of said $KH_2PO_4$ based on the total weight of the precursor catalyst is about 15 wt %. In even yet another embodiment of the present invention, the precursor catalyst consists of $KH_2PO_4$ and fused silica; wherein the weight of said $KH_2PO_4$ based on the total weight of the precursor catalyst is about 30 wt %. In one embodiment of the present invention, the precursor catalyst consists of $RbH_2PO_4$ and fused silica; wherein the weight of said $RbH_2PO_4$ based on the total weight of the precursor catalyst is about 14 wt %. In another embodiment of the present invention, the precursor catalyst consists of $RbH_2PO_4$ and fused silica; wherein the weight of said $RbH_2PO_4$ based on the total weight of the precursor catalyst is about 29 wt %.

In one embodiment of the present invention, the precursor catalyst comprises two or more different phosphate compounds selected from the group consisting of $M_j^I(H_{(2+i-j)}P_iO_{(3i+1)})$, $(NH_4)_1(H_{(2+k-1)}P_kO_{(3k+1)})$, $M_p^I(H_{(m-p)}(PO_3)_m)$, $(NH_4)_r(H_{(q-r)}(PO_3)_q)$, $M_u^I(H_{(t-u)}P_{(2s+t)}O_{(5s+3t)})$, $(NH_4)_\alpha(H_{(w-\alpha)}P_{(2v+w)}O_{(5v+3w)})$, $M_2^IO$, $M^IOH$, $M^INO_3$, $M_2^ICO_3$, and $(H(CH_2)_R COO)M^I$; wherein $M^I$ is a monovalent cation selected from the group consisting of $Li^+$, $Na^+$, $K^+$, $Rb^+$, $Cs^+$, $Ag^+$, $Tl^+$, and mixtures thereof; wherein i, k, m, q, s, and v are integers greater than 0; wherein j, l, p, r, u, and a are real numbers equal to or greater than 0; wherein t, w, and R are integers equal to or greater than 0; wherein (2+i−j), (2+k−1), (m−p), (q−r), (t−u), and (w−a) are equal to or greater than 0; and wherein the ratio of the total moles of said one or more monovalent cations and the total moles of phosphorus in said precursor catalyst is about 1.

In another embodiment of the present invention, the precursor catalyst comprises one or more phosphate salts consisting essentially of one or more monovalent cations, and one or more phosphate anions selected from the group represented by molecular formulae $[H_2P_yO_{(3y+1)}]^{y-}$ and $[PO_3]_z^{z-}$; wherein y is any integer equal to or greater than 1 and z is any integer equal to or greater than 3. In the context of the present invention, the anion represented by molecular formula $[PO_3]_z^{z-}$ can refer either to the anion of cyclophosphate salts or to the anion of long-chain linear polyphosphate salts as described in "Phosphoric Acids and Phosphates, Kirk-Othmer Encyclopedia of Chemical Technology" by David R. Gard (published online: 15 Jul. 2005) and "Phosphorus: Chemistry, Biochemistry and Technology" by D. E. C. Corbridge (2013). When the molecular formula $[PO_3]_z^{z-}$ refers to the anion of long chain polyphosphate salts, the molecular formula is not precise in that it does not include the minor perturbation of excess negative charge owing to the two end-group oxygens.

The precursor catalyst of the present invention can be utilized to catalyze several chemical reactions. Non-limiting examples of reactions are: dehydration of lactic acid, lactic acid derivatives, or mixtures thereof to acrylic acid; dehydration of 3-hydroxypropionic acid, 3-hydroxypropionic acid derivatives, or mixtures thereof to acrylic acid; dehydration of glycerin to acrolein; isomerization of lactic acid to 3-hydroxypropionic acid in the presence of water; reduction of hydroxypropionic acid to propionic acid or 1-propanol in the presence of hydrogen gas; dehydration of aliphatic alcohols to alkenes or olefins; dehydrogenation of aliphatic alcohols to ethers; other dehydrogenations, hydrolyses, alkylations, dealkylations, oxidations, disproportionations, esterifications, cyclizations, isomerizations, condensations, aromatizations, polymerizations; and other reactions that may be apparent to those having ordinary skill in the art.

IV Methods of Preparing the Catalyst

In the context of the present invention, the triple point of a phosphate salt is the temperature and water partial pressure at which three phases of the phosphate salt (i.e., crystalline and fully-hydrated, crystalline and fully-dehydrated, and amorphous and partially-dehydrated) coexist in thermodynamic equilibrium. By way of example, and not limitation, the triple point can be located by determining the interception of two (out of three) phase boundary curves in the water partial pressure versus temperature phase equilibrium diagram (see FIG. 1): Curve A: phase boundary between crystalline and fully-hydrated phosphate salt, and crystalline and fully-dehydrated phosphate salt, at low temperature and water partial pressure (e.g. below about 248° C. and 0.85 bar for potassium phosphate salts, and below about 267° C. and 0.35 bar for cesium phosphate salts); Curve B: phase boundary between crystalline and fully-dehydrated phosphate salt, and amorphous and partially-dehydrated phosphate salt at high temperature and medium water partial pressure (e.g. above about 248° C. and 0.85 bar for potassium phosphate salts, and above about 267° C. and 0.35 bar for cesium phosphate salts); and Curve C: phase boundary between crystalline and fully-hydrated phosphate salt, and amorphous and partially-dehydrated phosphate salt at high temperature and high water partial pressure.

The phase boundary curves can be determined by any method known to those skilled in the art, such as, by way of example and not limitation, in-situ x-ray diffraction (XRD), thermal analysis (e.g. thermogravimetric analysis, differential thermal analysis, and differential scanning calorimetry), Raman spectroscopy, infrared spectroscopy (IR), nuclear magnetic resonance (NMR) spectroscopy, or the methods described in Taninouchi, Y.-k., et al., *J. Electrochem. Soc.* 156:B572-B579 (2009); or Ikeda, A. and Haile, S. M., *Solid State Ionics* 2012, 213:63-71 (2012) (all incorporated herein by reference). As an illustration, in a method based on the in-situ XRD technique, a precursor catalyst comprising a crystalline phosphate salt is contacted, at high temperature (e.g. 450° C.), with a gas feed stream consisting of an inert gas (e.g. nitrogen, helium, or air) and water vapor at a specific water partial pressure until equilibrium is achieved.

Then, the temperature is gradually decreased while monitoring changes on x-ray diffraction patterns, until a phase transition is observed. The same procedure is repeated at different water partial pressures and the transition temperatures are recorded. The water partial pressures (in logarithmic scale) are plotted against the transition temperatures (in linear scale) and fitted to the Arrhenius equation ($\log_{10}(P_{H_2O})=A+B/T$). Finally, the triple point is calculated by determining the interception point between the two phase boundary curves (i.e., curve A and curve B in FIG. 1).

The active catalysts of the present invention are the amorphous and partially-dehydrated phosphate salts that lie between Curves B and C (bifurcated area above the triple point) in the water partial pressure versus temperature phase equilibrium diagram of the catalyst (e.g. FIG. 1). These active catalysts can be produced by subjecting precursor catalysts containing a crystalline phosphate salt that lies either above Curves A and C or below Curves A and B in FIG. 1) to sufficient temperature or water partial pressure or combination of both for the crystalline phosphate salt to become an amorphous and partially-dehydrated phosphate salt lying between Curves B and C in the phase equilibrium diagram.

In one embodiment of the present invention, a method of converting a precursor catalyst comprising a crystalline phosphate salt to an active catalyst comprising an amorphous and partially-dehydrated phosphate salt comprises contacting said precursor catalyst with a gas feed stream comprising water vapor; wherein said contacting is performed at a temperature and water partial pressure sufficient to convert said crystalline phosphate salt to said amorphous and partially-dehydrated phosphate salt. In another embodiment of the present invention, a method of converting a precursor catalyst comprising a crystalline phosphate salt to an active catalyst comprising an amorphous and partially-dehydrated phosphate salt comprises contacting said precursor catalyst with a gas feed stream comprising water vapor, hydroxypropionic acid, hydroxypropionic acid derivatives, or mixtures thereof; wherein said contacting is performed at a temperature and water partial pressure sufficient to convert said crystalline phosphate salt to said amorphous and partially-dehydrated phosphate salt; and wherein said contacting produces acrylic acid, acrylic acid derivatives, or mixtures thereof from said hydroxypropionic acid, hydroxypropionic acid derivatives, or mixtures thereof.

In one embodiment of the present invention, the temperature at which said gas feed stream contacts said precursor catalyst comprising a crystalline phosphate salt is between about 120° C. and about 700° C. In another embodiment of the present invention, the temperature at which said gas feed stream contacts said precursor catalyst comprising a crystalline phosphate salt is between about 150° C. and about 500° C. In yet another embodiment of the present invention, the temperature at which said gas feed stream contacts said precursor catalyst comprising a crystalline phosphate salt is between about 300° C. and about 450° C. In even yet another embodiment of the present invention, the temperature at which said gas feed stream contacts said precursor catalyst comprising a crystalline phosphate salt is between about 325° C. and about 400° C.

In one embodiment of the present invention, the water partial pressure in said gas feed stream is equal to or greater than about 0.4 bar. In another embodiment of the present invention, the water partial pressure in said gas feed stream is equal to or greater than about 0.8 bar. In yet another embodiment of the present invention, the water partial pressure in said gas feed stream is between about 0.4 bar and about 20 bar. In even yet another embodiment of the present invention, the water partial pressure in said gas feed stream is between about 0.8 bar and about 16 bar. In one embodiment of the present invention, the water partial pressure in said gas feed stream is about 13 bar.

In one embodiment of the present invention, the total pressure of said gas feed stream is equal to or greater than about 1 bar. In another embodiment of the present invention, the total pressure of said gas feed stream is equal to or greater than about 4 bar. In yet another embodiment of the present invention, the total pressure of said gas feed stream is between about 4 bar and about 35 bar. In even yet another embodiment of the present invention, the total pressure of said gas feed stream is between about 8 bar and about 30 bar. In one embodiment of the present invention, the total pressure of said gas feed stream is about 26 bar.

In one embodiment of the present invention, a method of converting a precursor catalyst comprising $CsPO_3$ or $CsH_2PO_4$ to an active catalyst comprising an amorphous and partially-dehydrated phosphate salt $CsH_{2(1-x)}PO_{(4-x)}$ comprises contacting said precursor catalyst with a gas feed stream comprising water vapor; wherein said contacting is performed at a temperature and a water partial pressure; wherein said temperature is about 400° C.; and wherein said water partial pressure is between about 3 bar and about 20 bar. In another embodiment of the present invention, a method of converting a precursor catalyst comprising $CsPO_3$ or $CsH_2PO_4$ to an active catalyst comprising an amorphous and partially-dehydrated phosphate salt $CsH_{2(1-x)}PO_{(4-x)}$ comprises contacting said precursor catalyst with a gas feed stream comprising water vapor; wherein said contacting is performed at a temperature and a water partial pressure; wherein said temperature is about 375° C.; and wherein said water partial pressure is between about 2 bar and about 10 bar. In yet another embodiment of the present invention, a method of converting a precursor catalyst comprising $CsPO_3$ or $CsH_2PO_4$ to an active catalyst comprising an amorphous and partially-dehydrated phosphate salt $CsH_{2(1-x)}PO_{(4-x)}$ comprises contacting said precursor catalyst with a gas feed stream comprising water vapor; wherein said contacting is performed at a temperature and a water partial pressure; wherein said temperature is about 350° C.; and wherein said water partial pressure is between about 1.5 bar and about 5 bar. In even yet another embodiment of the present invention, a method of converting a precursor catalyst comprising $CsPO_3$ or $CsH_2PO_4$ to an active catalyst comprising an amorphous and partially-dehydrated phosphate salt $CsH_{2(1-x)}PO_{(4-x)}$ comprises contacting said precursor catalyst with a gas feed stream comprising water vapor; wherein said contacting is performed at a temperature and a water partial pressure; wherein said temperature is about 325° C.; and wherein said water partial pressure is between about 1 bar and about 2 bar. In one embodiment of the present invention, a method of converting a precursor catalyst comprising $CsPO_3$ or $CsH_2PO_4$ to an active catalyst comprising an amorphous and partially-dehydrated phosphate salt $CsH_{2(1-x)}PO_{(4-x)}$ comprises contacting said precursor catalyst with a gas feed stream comprising water vapor; wherein said contacting is performed at a temperature and a water partial pressure; wherein said temperature is about 300° C.; and wherein said water partial pressure is between about 0.7 bar and about 1.2 bar.

In one embodiment of the present invention, a method of converting a precursor catalyst comprising $CsPO_3$ or $CsH_2PO_4$ to an active catalyst comprising an amorphous and partially-dehydrated phosphate salt $CsH_{2(1-x)}PO_{(4-x)}$ comprises contacting said precursor catalyst with a gas feed stream comprising water vapor; wherein said contacting is performed at a temperature and a water partial pressure; wherein said water partial pressure is about 1 bar; and wherein said temperature is between about 300° C. and about 325° C. In another embodiment of the present invention, a method of converting a precursor catalyst comprising $CsPO_3$ or $CsH_2PO_4$ to an active catalyst comprising an amorphous and partially-dehydrated phosphate salt $CsH_{2(1-x)}PO_{(4-x)}$ comprises contacting said precursor catalyst with a gas feed stream comprising water vapor; wherein said contacting is performed at a temperature and a water partial pressure; wherein said water partial pressure is about 2 bar; and wherein said temperature is between about 325° C. and about 375° C. In yet another embodiment of the present invention, a method of converting a precursor catalyst comprising $CsPO_3$ or $CsH_2PO_4$ to an active catalyst comprising an amorphous and partially-dehydrated phosphate salt $CsH_{2(1-x)}PO_{(4-x)}$ comprises contacting said precursor catalyst with a gas feed stream comprising water vapor; wherein said contacting is performed at a temperature and a water partial pressure; wherein said water partial pressure is about 3 bar; and wherein said temperature is between about 325° C. and about 400° C. In even yet another embodiment of the present invention, a method of converting a precursor catalyst comprising $CsPO_3$ or $CsH_2PO_4$ to an active catalyst comprising an amorphous and partially-dehydrated phosphate salt $CsH_{2(1-x)}PO_{(4-x)}$ comprises contacting said precursor catalyst with a gas feed stream comprising water vapor; wherein said contacting is performed at a temperature and a water partial pressure; wherein said water partial pressure is about 10 bar; and wherein said temperature is between about 375° C. and about 500° C.

In one embodiment of the present invention, the weight of said $CsPO_3$ based on the total weight of said precursor catalyst is about 13 wt %. In another embodiment of the present invention, the weight of said $CsPO_3$ based on the total weight of said precursor catalyst is about 26 wt %.

In one embodiment of the present invention, a method of converting a precursor catalyst comprising $KPO_3$ or $KH_2PO_4$ to an active catalyst comprising an amorphous and partially-dehydrated phosphate salt $KH_{2(1-x)}PO_{(4-x)}$ comprises contacting said precursor catalyst with a gas feed stream comprising water vapor; wherein said contacting is performed at a temperature and a water partial pressure; wherein said temperature is about 400° C.; and wherein said water partial pressure is between about 5 bar and about 400 bar. In another embodiment of the present invention, a method of converting a precursor catalyst comprising $KPO_3$ or $KH_2PO_4$ to an active catalyst comprising an amorphous and partially-dehydrated phosphate salt $KH_{2(1-x)}PO_{(4-x)}$ comprises contacting said precursor catalyst with a gas feed stream comprising water vapor; wherein said contacting is performed at a temperature and a water partial pressure; wherein said temperature is about 375° C.; and wherein said water partial pressure is between about 4 bar and about 100 bar. In yet another embodiment of the present invention, a method of converting a precursor catalyst comprising $KPO_3$ or $KH_2PO_4$ to an active catalyst comprising an amorphous and partially-dehydrated phosphate salt $KH_{2(1-x)}PO_{(4-x)}$ comprises contacting said precursor catalyst with a gas feed stream comprising water vapor; wherein said contacting is performed at a temperature and a water partial pressure; wherein said temperature is about 350° C.; and wherein said water partial pressure is between about 3 bar and about 50 bar. In even yet another embodiment of the present invention, a method of converting a precursor catalyst comprising $KPO_3$ or $KH_2PO_4$ to an active catalyst comprising an amorphous and partially-dehydrated phosphate salt $KH_{2(1-x)}PO_{(4-x)}$ comprises contacting said precursor catalyst with a gas feed stream comprising water vapor; wherein said contacting is performed at a temperature and a water partial pressure; wherein said temperature is about 325° C.; and wherein said water partial pressure is between about 2 bar and about 20 bar. In one embodiment of the present invention, a method of converting a precursor catalyst comprising $KPO_3$ or $KH_2PO_4$ to an active catalyst comprising an amorphous and partially-dehydrated phosphate salt $KH_{2(1-x)}PO_{(4-x)}$ comprises contacting said precursor catalyst with a gas feed stream comprising water vapor; wherein said contacting is performed at a temperature and a water partial pressure; wherein said temperature is about 300° C.; and wherein said water partial pressure is between about 1.5 bar and about 7 bar.

In one embodiment of the present invention, a method of converting a precursor catalyst comprising $KPO_3$ or $KH_2PO_4$ to an active catalyst comprising an amorphous and partially-dehydrated phosphate salt $KH_{2(1-x)}PO_{(4-x)}$ comprises contacting said precursor catalyst with a gas feed stream comprising water vapor; wherein said contacting is performed at a temperature and a water partial pressure; wherein said water partial pressure is about 2 bar; and wherein said temperature is between about 275° C. and about 325° C. In another embodiment of the present invention, a method of converting a precursor catalyst comprising $KPO_3$ or $KH_2PO_4$ to an active catalyst comprising an amorphous and partially-dehydrated phosphate salt $KH_{2(1-x)}PO_{(4-x)}$ comprises contacting said precursor catalyst with a gas feed stream comprising water vapor; wherein said contacting is performed at a temperature and a water partial pressure; wherein said water partial pressure is about 4 bar; and wherein said temperature is between about 285° C. and about 375° C. In yet another embodiment of the present invention, a method of converting a precursor catalyst comprising $KPO_3$ or $KH_2PO_4$ to an active catalyst comprising an amorphous and partially-dehydrated phosphate salt $KH_{2(1-x)}PO_{(4-x)}$ comprises contacting said precursor catalyst with a gas feed stream comprising water vapor; wherein said contacting is performed at a temperature and a water partial pressure; wherein said water partial pressure is about 8 bar; and wherein said temperature is between about 300° C. and about 450° C.

In one embodiment of the present invention, the weight of said $KPO_3$ based on the total weight of said precursor catalyst is about 13 wt %. In another embodiment of the present invention, the weight of said $KPO_3$ based on the total weight of said precursor catalyst is about 26 wt %.

In one embodiment of the present invention, a method of converting a precursor catalyst comprising $RbPO_3$ or $RbH_2PO_4$ to an active catalyst comprising an amorphous and partially-dehydrated phosphate salt $RbH_{2(1-x)}PO_{(4-x)}$ comprises contacting said precursor catalyst with a gas feed stream comprising water vapor; wherein said contacting is performed at a temperature and a water partial pressure; wherein said temperature is about 400° C.; and wherein said water partial pressure is between about 4 bar and about 200 bar. In another embodiment of the present invention, a method of converting a precursor catalyst comprising $RbPO_3$ or $RbH_2PO_4$ to an active catalyst comprising an amorphous and partially-dehydrated phosphate salt $RbH_{2(1-x)}PO_{(4-x)}$ comprises contacting said precursor catalyst with a gas feed stream comprising water vapor; wherein said contacting is performed at a temperature and a water partial pressure; wherein said temperature is about 375° C.; and wherein said water partial pressure is between about 3 bar and about 50 bar. In yet another embodiment of the present invention, a method of converting a precursor catalyst comprising $RbPO_3$ or $RbH_2PO_4$ to an active catalyst comprising an amorphous and partially-dehydrated phosphate salt $RbH_{2(1-x)}PO_{(4-x)}$ comprises contacting said precursor catalyst with a gas feed stream comprising water vapor; wherein said contacting is performed at a temperature and a water partial pressure; wherein said temperature is about 350° C.; and wherein said water partial pressure is between about 2.5 bar and about 25 bar. In even yet another embodiment of the present invention, a method of converting a precursor catalyst comprising $RbPO_3$ or $RbH_2PO_4$ to an active catalyst comprising an amorphous and partially-dehydrated phosphate salt $RbH_{2(1-x)}PO_{(4-x)}$ comprises contacting said precursor catalyst with a gas feed stream comprising water vapor; wherein said contacting is performed at a temperature and a water partial pressure; wherein said temperature is about 325° C.; and wherein said water partial pressure is between about 1.5 bar and about 10 bar. In one embodiment of the present invention, a method of converting a precursor catalyst comprising $RbPO_3$ or $RbH_2PO_4$ to an active catalyst comprising an amorphous and partially-dehydrated phosphate salt $RbH_{2(1-x)}PO_{(4-x)}$ comprises contacting said precursor catalyst with a gas feed stream comprising water vapor; wherein said contacting is performed at a temperature and a water partial pressure; wherein said temperature is about 300° C.; and wherein said water partial pressure is between about 1 bar and about 4 bar.

In one embodiment of the present invention, a method of converting a precursor catalyst comprising $RbPO_3$ or $RbH_2PO_4$ to an active catalyst comprising an amorphous and partially-dehydrated phosphate salt $RbH_{2(1-x)}PO_{(4-x)}$ comprises contacting said precursor catalyst with a gas feed stream comprising water vapor; wherein said contacting is performed at a temperature and a water partial pressure; wherein said water partial pressure is about 1.5 bar; and wherein said temperature is between about 290° C. and about 325° C. In another embodiment of the present invention, a method of converting a precursor catalyst comprising $RbPO_3$ or $RbH_2PO_4$ to an active catalyst comprising an amorphous and partially-dehydrated phosphate salt $RbH_{2(1-x)}PO_{(4-x)}$ comprises contacting said precursor catalyst with a gas feed stream comprising water vapor; wherein said contacting is performed at a temperature and a water partial pressure; wherein said water partial pressure is about 3 bar; and wherein said temperature is between about 300° C. and about 375° C. In yet another embodiment of the present invention, a method of converting a precursor catalyst comprising $RbPO_3$ or $RbH_2PO_4$ to an active catalyst comprising an amorphous and partially-dehydrated phosphate salt $RbH_{2(1-x)}PO_{(4-x)}$ comprises contacting said precursor catalyst with a gas feed stream comprising water vapor; wherein said contacting is performed at a temperature and a water partial pressure; wherein said water partial pressure is about 3 bar; and wherein said temperature is between about 325° C. and about 400° C.

In even yet another embodiment of the present invention, a method of converting a precursor catalyst comprising $RbPO_3$ or $RbH_2PO_4$ to an active catalyst comprising an amorphous and partially-dehydrated phosphate salt $RbH_{2(1-x)}PO_{(4-x)}$ comprises contacting said precursor catalyst with a gas feed stream comprising water vapor; wherein said contacting is performed at a temperature and a water partial pressure; wherein said water partial pressure is about 10 bar; and wherein said temperature is between about 375° C. and about 500° C.

In one embodiment of the present invention, the weight of said $RbPO_3$ based on the total weight of said precursor catalyst is about 13 wt %. In another embodiment of the present invention, the weight of said $RbPO_3$ based on the total weight of said precursor catalyst is about 26 wt %.

In one embodiment of the present invention, the method of preparing the catalyst further comprises molding the particles of said precursor catalyst before said contacting with said gas feed stream. Non-limiting examples of molding operations are granulation, agglomeration, compaction, pelleting, and extrusion. In another embodiment of the present invention, the method of preparing the catalyst further comprises size reduction or grinding of the particles of said precursor catalyst before said contacting with said gas feed stream. In one embodiment of the present invention, the method of preparing the catalyst further comprises sieving the particles of said precursor catalyst to select a material of specific size distribution before said contacting with said gas feed stream. In another embodiment of the present invention, the method of preparing the catalyst further comprises sieving the particles of said precursor catalyst to a median particle size between about 50 µm and about 500 µm. In yet another embodiment of the present invention, the method of preparing the catalyst further comprises sieving the particles of said precursor catalyst to a median particle size between about 100 m and about 200 µm. In even yet another embodiment of the present invention, the method of preparing the catalyst further comprises sieving the particles of said precursor catalyst to a particle size between about 106 m and about 212 µm.

In one embodiment of the present invention, the active catalyst is prepared via: (a) mixing $KH_2PO_4$ and amorphous silica in a weight ratio between about 2:1 and about 1:8, to produce a precursor catalyst, (b) heating said precursor catalyst between about 200° C. and about 650° C. for about 1 hour to about 12 hours to produce a calcined precursor catalyst, (c) optionally grinding and sieving said calcined precursor catalyst to produce a ground calcined precursor catalyst, and (d) contacting said calcined precursor catalyst or said ground calcined precursor catalyst with a gas feed stream comprising nitrogen and water vapor; wherein the water partial pressure in said gas feed stream is between about 5 bar and about 15 bar; and wherein said contacting is performed at a temperature between about 325° C. and about 425° C. to produce said active catalyst.

In another embodiment of the present invention, the active catalyst is prepared via: (a) mixing $KH_2PO_4$ and $BaSO_4$ in a weight ratio between about 2:1 and about 1:8, to produce a precursor catalyst, (b) heating said precursor catalyst between about 200° C. and about 650° C. for about 1 hour to about 12 hours to produce a calcined precursor catalyst, (c) optionally grinding and sieving said calcined precursor catalyst to produce a ground calcined precursor catalyst, and (d) contacting said calcined precursor catalyst or said ground calcined precursor catalyst with a gas feed stream comprising nitrogen and water vapor; wherein the water partial pressure in said gas feed stream is between about 5 bar and about 15 bar; and wherein said contacting is performed at a temperature between about 325° C. and about 425° C. to produce said active catalyst.

In another embodiment of the present invention, the active catalyst is prepared via (a) mixing $K_2HPO_4$, $(NH_4)_2HPO_4$, and amorphous silica in a weight ratio between about 1.3:1.0:16.1 and about 1.3:1.0:1.2 to produce a precursor catalyst, (b) heating said precursor catalyst between about 200° C. and about 650° C. for about 1 hour to about 12 hours to produce a calcined precursor catalyst, (c) optionally grinding and sieving said calcined precursor catalyst to produce a ground precursor catalyst, and (d) contacting said calcined precursor catalyst or said ground calcined precursor catalyst with a gas feed stream comprising nitrogen and water vapor; wherein the water partial pressure in said gas feed stream is between about 5 bar and about 15 bar and wherein said contacting is performed at a temperature between about 325° C. and about 425° C. to produce said active catalyst.

The method of preparing the precursor catalyst can comprise mixing of two or more different components. This mixing step can be performed by any method known to those skilled in the art, such as, by way of example and not limitation: solid mixing, impregnation, or co-precipitation. In the solid mixing method, the various components are physically mixed together with optional grinding using any method known to those skilled in the art, such as, by way of example and not limitation, shear, extensional, kneading, extrusion, ball milling, and others, and alternatively followed by any additional treatment or activation step. In the impregnation method, a suspension of an insoluble component (e.g. inert support) is treated with a solution of precursor catalyst soluble ingredients, and the resulting material is then treated or activated under conditions that will convert the mixture to a more active or preferred state. In the co-precipitation method, a homogeneous solution of the precursor catalyst ingredients is precipitated by the addition of additional ingredients, followed by optional filtration and heating to remove solvents and volatile materials (e.g., water, nitric acid, carbon dioxide, ammonia, or acetic acid).

Mixing of precursor catalyst components with surfactants followed by heating can increase the precursor catalyst surface area. In one embodiment of the present invention, the method of preparing the catalyst further comprises mixing one or more surfactants with said precursor catalyst before said contacting with said gas feed stream. In another embodiment of the present invention, said one or more surfactants are cationic or zwitterionic. Non-limiting examples of surfactants are myristyltrimethylammonium bromide, hexadecyltrimethylammonium bromide, dodecyltrimethylammonium bromide, decyltrimethylammonium bromide, and octadecyltrimethyl ammonium bromide.

Heating can promote chemical reactions, thermal decompositions, phase transitions, and/or removal of volatile materials. In one embodiment of the present invention, the method of preparing the active catalyst further comprises heating said precursor catalyst at a temperature equal to or greater than 180° C. before said contacting with said gas feed stream. In another embodiment of the present invention, the method of preparing the active catalyst further comprises heating said precursor catalyst at a temperature equal to or greater than 300° C. before said contacting with said gas feed stream. In yet another embodiment of the present invention, the method of preparing the active catalyst further comprises heating said precursor catalyst at a temperature between about 350° C. and about 650° C. before said contacting with said gas feed stream. In even yet another embodiment of the present invention, the method of preparing the active catalyst further comprises heating said precursor catalyst at a temperature between about 400° C. and about 450° C. before said contacting with said gas feed stream. Said heating is typically done using any method known to those skilled in the art, such as, by way of example and not limitation, convection, conduction, radiation, microwave heating, and others. The heating is performed with equipment such as, by way of example and not limitation, furnaces, atomizers, or reactors of various designs, comprising shaft furnaces, rotary kilns, hearth furnaces, fluidized bed reactors, spay dryers. The duration of said heating is, in one embodiment of the present invention, between about 1 hour and about 72 hours. In another embodiment, the duration of said heating is between about 2 hours and about 12 hours. In yet another embodiment, the duration of said heating is about 4 hours. In one embodiment, the temperature ramp in said heating is between about 0.5° C./min and about 20° C./min. In another embodiment, the temperature ramp in said heating is about 10° C./min.

V Methods of Making Acrylic Acid, Acrylic Acid Derivatives, or Mixtures Thereof

A method of dehydrating hydroxypropionic acid, hydroxypropionic acid derivatives, or mixtures thereof to acrylic acid, acrylic acid derivatives, or mixtures thereof is provided. In one embodiment of the present invention, said hydroxypropionic acid is selected from the group consisting of lactic acid (2-hydroxypropionic acid), 3-hydroxypropionic acid, and mixtures thereof; and said hydroxypropionic acid derivatives are selected from the group consisting of lactic acid derivatives, 3-hydroxypropionic acid derivatives, and mixtures thereof.

In another embodiment of the present invention, said hydroxypropionic acid is lactic acid and said hydroxypropionic acid derivatives are lactic acid derivatives. Lactic acid can be D-lactic acid, L-lactic acid, or mixtures thereof (including racemic mixture). Lactic acid derivatives can be metal or ammonium salts of lactic acid, alkyl esters of lactic acid, lactic acid oligomers, cyclic di-esters of lactic acid, lactic acid anhydride, 2-alkoxypropionic acids or their alkyl esters, 2-aryloxypropionic acids or their alkyl esters, 2-acyloxypropionic acids or their alkyl esters, or a mixture thereof. Non-limiting examples of metal salts of lactic acid are sodium lactate, potassium lactate, and calcium lactate. Non-limiting examples of alkyl esters of lactic acid are methyl lactate, ethyl lactate, butyl lactate, 2-ethylhexyl lactate, and mixtures thereof. A non-limiting example of cyclic di-esters of lactic acid is dilactide. Non-limiting examples of 2-alkoxypropionic acids are 2-methoxypropionic acid and 2-ethoxypropionic acid. A non-limiting example of 2-aryloxypropionic acid is 2-phenoxypropionic acid. A non-limiting example of 2-acyloxypropionic acid is 2-acetoxypropionic acid. In yet another embodiment of the present invention, the lactic acid derivative is methyl lactate. Methyl lactate can be neat or in a solution with water, methanol, or mixtures thereof. 3-hydroxypropionic acid derivatives can be metal or ammonium salts of 3-hydroxypropionic acid, alkyl esters of 3-hydroxypropionic acid, 3-hydroxypropionic acid oligomers, 3-alkoxypropionic acids or their alkyl esters, 3-aryloxypropionic acids or their alkyl esters, 3-acyloxypropionic acids or their alkyl esters, or a mixture thereof. Non-limiting examples of metal salts of 3-hydroxypropionic acid are sodium 3-hydroxypropionate, potassium 3-hydroxypropionate, and calcium 3-hydroxypropionate. Non-limiting examples of alkyl esters of hydroxypropionic acid are methyl 3-hydroxypropionate, ethyl 3-hydroxypropionate, butyl 3-hydroxypropionate, 2-ethylhexyl 3-hydroxypropionate, and mixtures thereof. Non-limiting examples of 3-alkoxypropionic acids are 3-methoxypropionic acid and 3-ethoxypropionic acid. A non-limiting example of 3-aryloxypropionic acid is 3-phenoxypropionic acid. A non-limiting example of 3-acyloxypropionic acid is 3-acetoxypropionic acid.

Hydroxypropionic acid, hydroxypropionic acid derivatives, or mixtures thereof can be produced by sugar fermentation or chemical conversion of sugars or other feedstock materials, such as glycerin. Nearly all world production of lactic acid is by sugar fermentation today; however, there are chemical conversion technologies currently in pilot or demo scale. Also, the sugar feedstock can be generation 1 sugar (i.e., sugar from corn, sugarcane, sugar beets, wheat, potato, rice, etc.) or generation 2 sugar (i.e., sugar from the hydrolysis of biomass or agricultural waste, such as bagasse, corn stover, rice husk, wheat straw, etc.).

Acrylic acid derivatives can be metal or ammonium salts of acrylic acid, alkyl esters of acrylic acid, acrylic acid oligomers, or mixtures thereof. Non-limiting examples of metal salts of acrylic acid are sodium acrylate, potassium acrylate, and calcium acrylate. Non-limiting examples of alkyl esters of acrylic acid are methyl acrylate, ethyl acrylate, butyl acrylate, 2-ethylhexyl acrylate, or mixtures thereof.

In one embodiment of the present invention, a method of making acrylic acid, acrylic acid derivatives, or mixtures thereof comprises contacting a gas feed stream comprising water vapor and hydroxypropionic acid, hydroxypropionic acid derivatives, or mixtures thereof with any active catalyst disclosed in Section II ("Active Catalysts for the Dehydration of Hydroxypropionic Acid or its Derivatives to Acrylic Acid or its Derivatives") or any precursor catalyst disclosed in Section III ("Precursor Catalysts for the Dehydration of Hydroxypropionic Acid or its Derivatives to Acrylic Acid or its Derivatives") of the present invention in a reactor at a temperature, a water partial pressure, a GHSV, and a WHSV to dehydrate said hydroxypropionic acid, hydroxypropionic acid derivatives, or mixtures thereof, whereby acrylic acid, acrylic acid derivatives, or mixtures thereof are produced as a result of the dehydration in the reactor.

In one embodiment of the present invention, said gas feed stream comprises water vapor and hydroxypropionic acid, hydroxypropionic acid derivatives, or mixtures thereof. In another embodiment of the present invention, said gas feed stream further comprises an essentially chemically inert gas (also called herein diluent). In the context of the present invention, an essentially chemically inert gas is any gas that is essentially chemically inert to said hydroxypropionic acid, hydroxypropionic acid derivatives, or mixtures thereof, but not necessarily to said catalyst. Non-limiting examples of essentially chemically inert gases or diluents are nitrogen, helium, argon, carbon dioxide, carbon monoxide, and mixtures thereof. In yet another embodiment of the present invention, said essentially chemically inert gas or diluent comprises nitrogen. In even yet another embodiment of the present invention, said essentially chemically inert gas or diluent consists essentially of nitrogen. In one embodiment of the present invention, said gas feed stream further comprises a gas selected from the group consisting of air and oxygen.

In one embodiment of the present invention, the concentration of the hydroxypropionic acid, hydroxypropionic acid derivatives, or mixtures thereof in said gas feed stream is between about 0.5 mol % and about 95 mol % (under STP conditions). In another embodiment of the present invention, the concentration of the hydroxypropionic acid, hydroxypropionic acid derivatives, or mixtures thereof in said gas feed stream is between about 1.5 mol % and about 20 mol % (under STP conditions). In yet another embodiment of the present invention, the concentration of the hydroxypropionic acid, hydroxypropionic acid derivatives, or mixtures thereof in said gas feed stream is between about 2 mol % and about 5 mol % (under STP conditions). In even yet another embodiment of the present invention, the concentration of the hydroxypropionic acid, hydroxypropionic acid derivatives, or mixtures thereof in said gas feed stream is about 2.5 mol % (under STP conditions). In one embodiment of the present invention, the concentration of the hydroxypropionic acid, hydroxypropionic acid derivatives, or mixtures thereof in said gas feed stream is about 2.5 mol % (under STP conditions), the concentration of the water vapor in said gas feed stream is about 50 mol % (under STP conditions), and the concentration of nitrogen in said gas feed stream is about 47.5 mol % (under STP conditions). In another embodiment of the present invention, the concentration of the hydroxypropionic acid, hydroxypropionic acid derivatives, or mixtures thereof in said gas feed stream is about 10 mol % (under STP conditions) and the concentration of the water vapor in said gas feed stream is about 90 mol % (under STP conditions).

In one embodiment of the present invention, the concentration of the lactic acid, lactic acid derivatives, or mixtures thereof in said gas feed stream is between about 0.5 mol % and about 95 mol %. In another embodiment of the present invention, the concentration of the lactic acid, lactic acid derivatives, or mixtures thereof in said gas feed stream is between about 1.5 mol % and about 20 mol %. In yet another embodiment of the present invention, the concentration of the lactic acid, lactic acid derivatives, or mixtures thereof in said gas feed stream is between about 2 mol % and about 5 mol %. In even yet another embodiment of the present invention, the concentration of the lactic acid, lactic acid derivatives, or mixtures thereof in said gas feed stream is about 2.5 mol %. In one embodiment of the present invention, the concentration of the lactic acid, lactic acid derivatives, or mixtures thereof in said gas feed stream is about 2.5 mol %, the concentration of the water vapor in said gas feed stream is about 50 mol %, and the concentration of nitrogen in said gas feed stream is about 47.5 mol %. In another embodiment of the present invention, the concentration of the lactic acid, lactic acid derivatives, or mixtures thereof in said gas feed stream is about 10 mol % and the concentration of the water vapor in said gas feed stream is about 90 mol %.

Non-limiting examples of reactors suitable for use in the present invention are static reactors, stirred tank reactors, recirculation reactors, fluidized bed reactors, packed-bed flow reactors, and combinations thereof. In one embodiment of the present invention, the gas feed stream flows down the reactor. In another embodiment of the present invention, the gas feed stream flows up the reactor. In yet another embodiment of the present invention, the gas feed stream flows horizontally in the reactor.

In one embodiment of the present invention, the reactor is a packed-bed flow reactor. Typically, a packed-bed flow reactor is a tubular reactor. In another embodiment of the present invention, the tubular packed-bed flow reactor is a single-layer reactor. In yet another embodiment of the present invention, the tubular packed-bed flow reactor is a bi-layer reactor. A half cross section of an exemplary tubular single-layer reactor is shown in FIG. 2, and a half cross section of an exemplary tubular bi-layer reactor is shown in FIG. 3.

Figure 2:
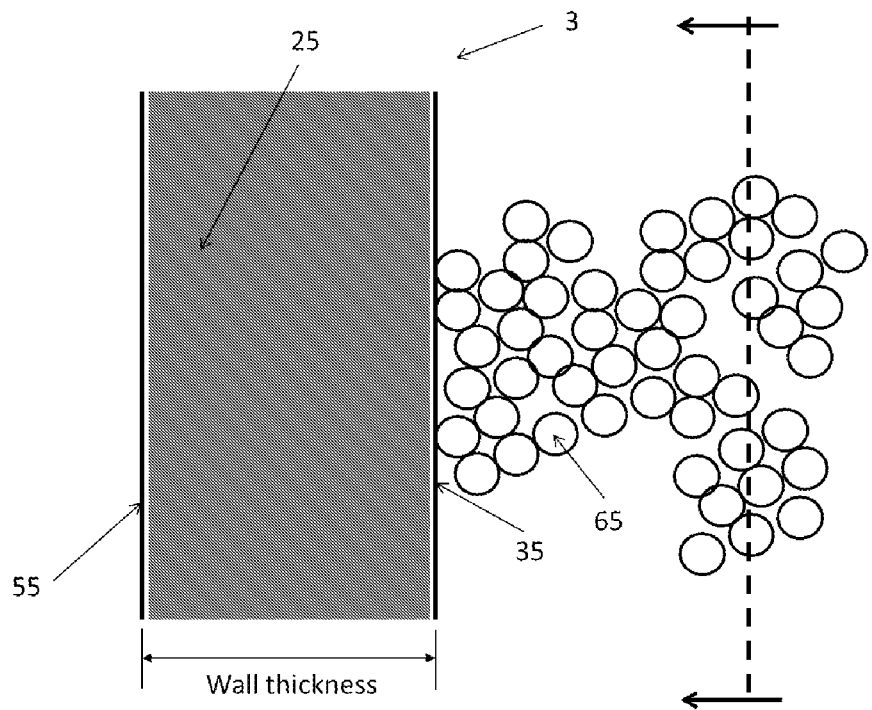
FIG. 2 is a half cross sectional side view of a tubular packed-bed flow single-layer reactor made in accordance with one embodiment of the present invention.

In FIG. 2, a single-layer reactor 3 consists of a single layer 25 (also called wall) that extends from an inner surface 35 to an outer surface 55 and has a wall thickness. The inner surface 35 is in contact with a catalyst 65. In one embodiment of the present invention, the single-layer reactor comprises a wall, an outer surface, and an inner surface; wherein said wall is made from a wall material, has a wall thickness, and extends from said outer surface to said inner surface; and wherein said inner surface is in contact with said catalyst. In another embodiment of the present invention, the wall thickness of a single-layer reactor is in accordance to the Nominal Pipe Standard (NPS) for seamless and welded steel pipes (ANSI B36.10 of 1979). In yet another embodiment of the present invention, the wall thickness of a single-layer reactor is between about 0.65 in. (1.651 mm) and about 0.5 in. (12.7 mm). In even yet another embodiment of the present invention, the wall thickness of a single-layer reactor is between about 0.65 in. (1.651 mm) and about 0.432 in. (10.973 mm). In one embodiment of the present invention, the wall thickness of a single-layer reactor is between about 0.065 in. (1.651 mm) and about 0.337 in. (8.56 mm). In another embodiment of the present invention, the wall thickness of a single-layer reactor is about 0.133 in. (3.378 mm).

Figure 3:
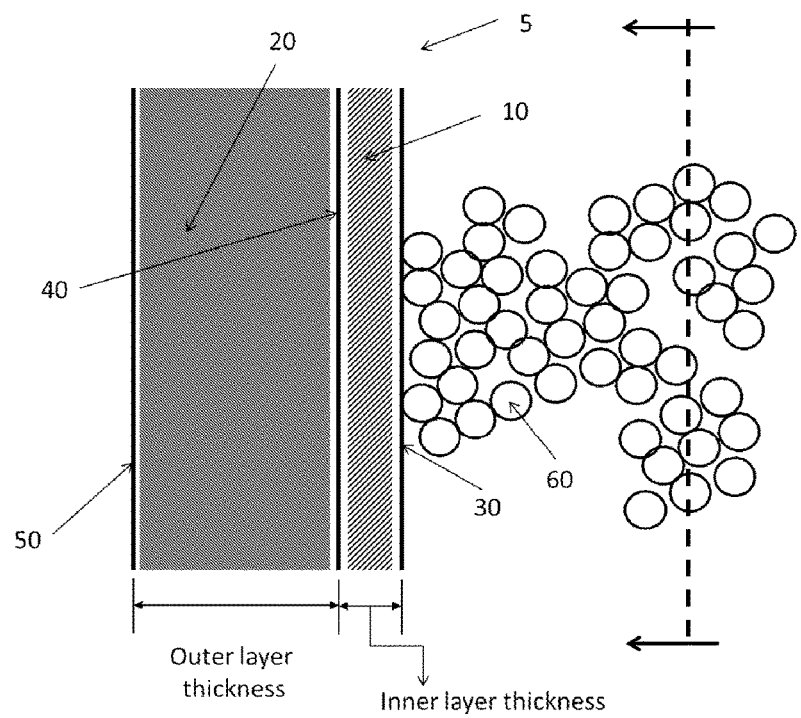
FIG. 3 is a half cross sectional side view of a tubular packed-bed flow bi-layer reactor made in accordance with one embodiment of the present invention with an inner layer and an outer layer.

In FIG. 3, a bi-layer reactor 5 comprises an inner surface 30 that comes in contact with a catalyst 60 and is the innermost surface of the bi-layer reactor 5. The bi-layer reactor 5 consists of an inner layer 10, which has an inner layer thickness, an outer layer 20, which has an outer layer thickness, an interface 40 between the outer layer 20 and the inner layer 10, and an outer surface 50, which is the outmost surface of the tubular reactor 5. In one embodiment of the present invention, the outer layer 20 of the bi-layer reactor 5 consists of two or more sublayers.

In another embodiment of the present invention, the bi-layer reactor comprises an outer layer, an inner layer, an outer surface, an inner surface, and an interface between said outer layer and said inner layer; wherein said outer layer is made from an outer layer material, has an outer layer thickness, and extends from said interface to said outer surface; wherein said inner layer is made from an inner layer material, has an inner layer thickness, and extends from said inner surface to said interface; and wherein said inner surface is in contact with said catalyst. In yet another embodiment of the present invention, said outer layer comprises two or more sublayers.

In one embodiment of the present invention, the inner layer thickness of a bi-layer reactor is between about 1 mm and about 20 mm. In another embodiment of the present invention, the inner layer thickness of a bi-layer reactor is between about 1.5 mm and about 10 mm. In yet another embodiment of the present invention, the inner layer thickness of a bi-layer reactor is between about 2 mm and about 8 mm. In even yet another embodiment of the present invention, the inner layer thickness of a bi-layer reactor is between about 3 mm and about 6 mm.

In one embodiment of the present invention, the outer layer thickness of a bi-layer reactor is between about 1 mm and about 20 mm. In another embodiment of the present invention, the outer layer thickness of a bi-layer reactor is between about 1.6 mm and about 12.7 mm. In yet another embodiment of the present invention, the outer layer thickness of a bi-layer reactor is between about 2 mm and about 9 mm. In even yet another embodiment of the present invention, the outer layer thickness of a bi-layer reactor is between about 3 mm and about 6 mm.

In one embodiment of the present invention, the outer diameter (OD) of a single-layer or a bi-layer reactor is in accordance to the Nominal Pipe Standard (NPS) for seamless and welded steel pipes (ANSI B36.10 of 1979). In another embodiment of the present invention, the OD of a single-layer or bi-layer reactor is between about 0.84 in. (21.34 mm) and about 9.625 in. (244.48 mm). In yet another embodiment of the present invention, the OD of a single-layer or a bi-layer reactor is between about 1.315 in. (33.4 mm) and about 6.625 in. (168.28 mm). In even yet another embodiment of the present invention, the OD of a single-layer or a bi-layer reactor is between about 2.375 in. (60.33 mm) and about 4.5 in. (114.3 mm). In one embodiment of the present invention, the OD of a single-layer or a bi-layer reactor is about 1.315 in. (33.4 mm).

The inner layer of a bi-layer reactor can be formed by a variety of methods. Non-limiting examples of methods to form the inner layer of a bi-layer reactor are bonding of the inner layer to the outer layer and dipping of the outer layer in a bath comprising the inner layer material. In one embodiment of the preset invention, the inner layer is formed by a bonding process of the inner layer to the outer layer. In another embodiment of the present invention, the bonding process is selected from the group consisting of cladding, laser cladding, explosion cladding, electromagnetic fusion cladding, fusion welding, explosion welding, gluing, pressing, rolling, coextrusion, thermal spraying, electroplating, and chemical vapor deposition. Non-limiting examples of bonding processes are cladding of a copper tube (inner layer) inside a stainless steel outer layer, explosion cladding of a zirconium tube (inner layer) inside a stainless steel outer layer, and electroplating silver on a stainless steel outer layer. In yet another embodiment of the present invention, the inner layer is bonded to the outer layer in the form of flat sheets, which are then welded into a reactor tube with an inner layer and an outer layer.

In yet another embodiment of the present invention, the inner layer is formed by a dipping process of the outer layer in a bath comprising the inner layer material. Non-limiting examples of stainless steel outer layer materials and aluminum or aluminum and silicon mixture inner layer materials that have been formed via a dipping process are the following commercial alloys: Aluminized Steel Type 1 Stainless 409 and Aluminized Steel Type 1 Stainless 439 (the inner layer material is a mixture of aluminum and silicon); and Aluminized Steel Type 2 (the inner layer material is aluminum only); all from AK Steel Corp. (West Chester, Ohio). The dipping process can be operated in batch, continuous, or semi-continuous modes.

The active catalysts of the present invention can be corrosive to the reactors because they are amorphous and partially-dehydrated phosphate salts. Unexpectedly, it has been found that some specific metals in the inner layer material of bi-layer reactors or wall material of single-layer reactors can reduce or eliminate the corrosive effects of the active catalysts, i.e., these metals are corrosion resistant reactor metals. Not wishing to be bound by any theory, applicants believe that the corrosion resistant reactor metals either: 1) form oxides and a thin passivating layer containing these oxides on the inner surface of the reactors (i.e., the surface of the reactor that is in contact with the catalyst and gas feed stream); or 2) have corrosion immunity as metals under the dehydration conditions. The oxide-based surface passivating layer can form when the inner surface of the reactor is subjected to oxidation. In one embodiment of the present invention, the oxidation occurs during the dehydration. In another embodiment of the present invention, the oxidation occurs before the dehydration. In yet another embodiment of the present invention, the oxidation that occurs before the dehydration can be a result of a pre-treatment step of the reactor.

In either case, the oxide-based surface passivating layer reduces or eliminates the oxidation of other reactor metals and migration of the resulting ions into the catalyst bed (i.e., corrosion).

Migration of the metal ions into the catalyst particles can have detrimental effects on the yield and selectivity of the produced acrylic acid, acrylic acid derivatives, or mixtures thereof, and catalyst lifetime, besides lowering the reactor strength itself. The metal cation in the oxide can be a metal in the inner layer material or wall material.

In one embodiment of the present invention, the bonding process is followed by oxidation of the inner surface. In another embodiment of the present invention, the dipping process is followed by oxidation of the inner surface.

A non-limiting example of a metal that forms an oxide-based surface passivating layer is aluminum contained in significant amounts (e.g. greater than about 1 wt %) in various inner layer or wall materials when the reactor is oxidized before or during the dehydration reaction. In one embodiment of the present invention, the inner surface is subjected to oxidation and forms an oxide-based surface passivating layer comprising alumina. Non-limiting examples of wall materials that have high aluminum content and form an oxide-based surface passivating layer of alumina on the inner surface of the reactor are the following commercial alloys: KANTHAL APM (ferritic iron-chromium-aluminum alloy; FeCrAl alloy) and KANTHAL APMT (ferritic iron-chromium-aluminum-molybdenum alloy; FeCrAlMo alloy) from Sandvik AB (Stockholm, Sweden); HAYNES®214® and HAYNES® HR-224® alloys (both are Ni-based alloys) from Haynes International, Inc. (Kokomo, Ind.); INCONEL® alloy 693 and INCONEL® alloy 601 (both are Ni-based alloys), and INCOLOY® alloy MA956 (Fe—Cr—Al alloy) from Special Metals Corporation (Huntington, W. Va.); and Fercalloy, Fercalloy 145, Fercalloy 135, and Resistalloy 134 from Resistalloy Trading Limited (Sheffield, South Yorkshire, UK).

A non-limiting example of a metal that forms an oxide-based surface passivating layer is silicon contained in significant amounts (e.g. greater than about 1 wt %) in various inner layer or wall materials when the reactor is oxidized before or during the dehydration reaction. In one embodiment of the present invention, the inner surface is subjected to oxidation and forms an oxide-based surface passivating layer comprising silica. Non-limiting examples of wall materials that have high silicon content and form an oxide-based surface passivating layer of silica on the inner surface of the reactor are the following commercial alloys: Sandvik SX and Sandvik 253 MA (both are austenitic steel alloys) from Sandvik AB (Stockholm, Sweden); and HAYNES® HR-160® and HASTELLOY® D-205 alloys (both are Ni-based alloys) from Haynes International, Inc. (Kokomo, Ind.). For the purposes of the present invention, Ni-based alloys are alloys that contain Ni in an amount greater than about 35 wt %.

A non-limiting example of a metal mixture that is the inner layer material of a bi-layer reactor is a mixture of aluminum and silicon that is formed as the inner layer via a dipping process when a stainless steel outer layer is dipped into a hot bath comprising aluminum and silicon and forms the aluminum and silicon inner layer. Then, the surface of the inner layer is oxidized either before or during the dehydration reaction to form an oxide-based surface passivating layer on the inner surface of the reactor comprising alumina and silica. In one embodiment of the present invention, the inner surface is subjected to oxidation and forms an oxide-based surface passivating layer comprising alumina and silica.

Typically, the thickness of the oxide-based surface passivating layer is between about 0.1 nm and 1 μm. In one embodiment of the present invention, the thickness of the oxide-based surface passivating layer is between about 0.3 nm and about 100 nm. In another embodiment of the present invention, the thickness of the oxide-based surface passivating layer is between about 1 nm and about 50 nm. In yet another embodiment of the present invention, the thickness of the oxide-based surface passivating layer is between about 5 nm and about 25 nm.

The inner layer, after it is formed by either a bonding process or a dipping process, can be subjected to oxidation to form an oxide-based surface passivating layer on the inner surface. The oxidation process can occur before the dehydration process or during the dehydration process, since the gas feed stream comprises water vapor. The oxidation process conditions depend on the inner layer material and are typically well known to those skilled in the art. Non-limiting examples of the oxidation process before the dehydration involve the use of air or oxygen atmospheres and: 1) temperature greater than about 500° C. and duration of a few hours, or 2) a 2-step process, where in step 1 the temperature is about 600° C. and the duration is about 1 hour, and in step 2 the temperature is about 1,000° C. and the duration is about 1 hour.

In one embodiment of the present invention, the inner layer material is selected from the group consisting of aluminum, silicon, copper, silver, gold, titanium, tantalum, tungsten, molybdenum, platinum, palladium, zirconium, or mixtures thereof. From the group of metals disclosed above, aluminum, silicon, titanium, tantalum, tungsten, molybdenum, and zirconium reduce or eliminate the corrosive effects of the active catalysts by forming oxides and oxide-based surface passivating layers; whereas, copper, silver, gold, platinum, and palladium reduce or eliminate the corrosive effects of the active catalysts as metals (not oxides) because of their corrosion immunity. In another embodiment of the present invention, the reactor material composition comprises a metal selected from the group consisting of aluminum, silicon, and mixtures thereof. In another embodiment of the present invention, the inner layer material is selected from the group consisting of copper, silver, and gold. In yet another embodiment of the present invention, the inner layer material is selected from the group consisting of titanium, tantalum, tungsten, molybdenum, platinum, palladium, zirconium, and mixtures thereof. In even yet another embodiment of the present invention, the inner layer material is selected from the group consisting of aluminum, silicon, copper, silver, and mixtures thereof. In one embodiment of the present invention, the inner layer material is copper. In another embodiment of the present invention, the inner layer material is silver. In another embodiment of the present invention, the inner layer material is zirconium. In yet another embodiment of the present invention, the inner layer material is titanium.

In one embodiment of the present invention, the bonding process is followed by oxidation of the inner surface when the inner layer material is selected from the group consisting of aluminum, silicon, titanium, tantalum, tungsten, molybdenum, zirconium, and mixtures thereof. In another embodiment of the present invention, the dipping process is followed by oxidation of the inner surface when the inner layer material is selected from the group consisting of aluminum, silicon, titanium, tantalum, tungsten, molybdenum, zirconium, and mixtures thereof.

In one embodiment of the present invention, the outer layer material is selected from the group consisting of carbon steel, stainless steel, titanium, Ni-based alloy, and mixtures thereof. In another embodiment of the present invention, the outer layer material is Ni-based alloy. In yet another embodiment of the present invention, the outer layer material is selected from the group consisting of stainless steel and carbon steel. In even yet another embodiment of the present invention, the outer layer material is carbon steel. In one embodiment of the present invention, the outer layer material is stainless steel.

In one embodiment of the present invention, the outer layer material is stainless steel and the inner layer material of the bi-layer reactor is selected from the group consisting of aluminum, silicon, and mixtures thereof. In another embodiment of the present invention, the outer layer material is stainless steel and the inner layer material of the bi-layer reactor is aluminum. In yet another embodiment of the present invention, the outer layer material is carbon steel and the inner layer material of the bi-layer reactor is selected from the group consisting of aluminum, silicon, and mixtures thereof. In even yet another embodiment of the present invention, the outer layer material is carbon steel and the inner layer material of the bi-layer reactor is aluminum.

Non-limiting examples of stainless steels are ferritic stainless steels, martensitic stainless steels, austenitic stainless steels, and duplex stainless steels. All stainless steels contain at least 10.5 wt % chromium. Ferritic stainless steels are classified in the 400 series, contain very little nickel, and their common grades include 409, 439, 18Cr-2Mo, 26Cr-1Mo, 29Cr-4Mo, and 29Cr-4Mo-2Ni. Martensitic stainless steels are classified in the 400 series, have higher levels of carbon than the ferritic grades, and their common grades include 410 and 420. Austenitic stainless steel grades are classified in the 200 and 300 series, make up over 70% of the stainless steel production, contain a minimum of 16 wt % chromium and 2 wt % to 20 wt % nickel, and their most common grades are 201, 301, 304, 316, and 316L. Finally, the duplex stainless steels have a mixed microstructure of austenitic and ferritic stainless steels, and have 19 wt % to 32 wt % chromium, up to 5 wt % molybdenum, and lower nickel contents than austenitic stainless steels. Sandvik AB (Stockholm, Sweden), Outokumpu Group (Espoo, Finland), ThyssenKrupp AG (Essen, Germany), Acerinox S.A. (Madrid, Spain), and AK Steel Corp. (West Chester, Ohio) are the main producers of stainless steel grades.

In one embodiment of the present invention, the outer layer material is stainless steel and the inner layer material of the bi-layer reactor is copper. In another embodiment of the present invention, the outer layer material is stainless steel and the inner layer material of the bi-layer reactor is silver. In yet another embodiment of the present invention, the outer layer material is stainless steel and the inner layer material of the bi-layer reactor is titanium. In even yet another embodiment of the present invention, the outer layer material is stainless steel and the inner layer material of the bi-layer reactor is zirconium.

In one embodiment of the present invention, the outer layer material is carbon steel and the inner layer material of the bi-layer reactor is copper. Carbon steel contains carbon in the range of 0.12 wt % to 2 wt %, copper in the range of 0.4 wt % to 0.6 wt %, manganese at no more than 1.65 wt %, and silicon at no more than 0.6 wt %. In another embodiment of the present invention, the outer layer material is carbon steel and the inner layer material of the bi-layer reactor is silver. In yet another embodiment of the present invention, the outer layer material is carbon steel and the inner layer material of the bi-layer reactor is titanium. In even yet another embodiment of the present invention, the outer layer material is carbon steel and the inner layer material of the bi-layer reactor is zirconium.

In one embodiment of the present invention, the outer layer material is stainless steel, the inner layer material is formed by a dipping process of the outer layer material of a bi-layer reactor in a bath comprising aluminum and silicon, and the inner surface of the bi-layer reactor is subjected to oxidation and forms an oxide-based surface passivating layer comprising alumina and silica. In another embodiment of the present invention, the outer layer material is stainless steel, the inner layer material is formed by a dipping process of the outer layer material of a bi-layer reactor in a bath comprising aluminum, and the inner surface of the bi-layer reactor is subjected to oxidation and forms an oxide-based surface passivating layer comprising alumina.

In one embodiment of the present invention, the corrosion resistant reactor metal is selected from the group consisting of aluminum, silicon, copper, silver, gold, titanium, tantalum, tungsten, molybdenum, platinum, palladium, zirconium, and mixtures thereof. In another embodiment of the present invention, the corrosion resistant reactor metal is selected from the group consisting of aluminum, silicon, titanium, tantalum, tungsten, molybdenum, zirconium, and mixtures thereof. In yet another embodiment of the present invention, the corrosion resistant reactor metal is selected from the group consisting of copper, silver, gold, platinum, palladium, and mixtures thereof. In even yet another embodiment of the present invention, the corrosion resistant reactor metal is selected from the group consisting of aluminum, silicon, and mixtures thereof. In one embodiment of the present invention, the corrosion resistant reactor metal is aluminum. In another embodiment of the present invention, the corrosion resistant reactor metal is silicon. In yet another embodiment of the present invention, the corrosion resistant reactor metal is selected from the group consisting of aluminum, silicon, and mixtures thereof. In even yet another embodiment of the present invention, the corrosion resistant reactor metal is copper. In one embodiment of the present invention, the corrosion resistant reactor metal is silver.

In one embodiment of the present invention, the corrosion resistant reactor metal is present in the reactor material in an amount greater than about 1 wt %. In another embodiment of the present invention, the corrosion resistant reactor metal is present in the reactor material in an amount greater than about 2 wt %. In yet another embodiment of the present invention, the corrosion resistant reactor metal is present in the reactor material in an amount greater than about 3 wt %. In even yet another embodiment of the present invention, the corrosion resistant reactor metal is present in the reactor material in an amount greater than about 4 wt %. In one embodiment of the present invention, the corrosion resistant reactor metal is present in the reactor material in an amount between about 1 wt % and about 6 wt %. In another embodiment of the present invention, the corrosion resistant reactor metal is present in the reactor material in an amount between about 3 wt % and about 5 wt %.

In one embodiment of the present invention, the wall material comprises aluminum in an amount greater than about 1 wt %. In another embodiment of the present invention, the wall material comprises aluminum in an amount greater than about 2 wt %. In yet another embodiment of the present invention, the wall material comprises aluminum in an amount greater than about 3 wt %. In even yet another embodiment of the present invention, the wall material comprises aluminum in an amount greater than about 4 wt %. In one embodiment of the present invention, the wall material comprises aluminum in an amount between about 1 wt % and about 50 wt %. In another embodiment of the present invention, the wall material comprises aluminum in an amount between about 1 wt % and about 6 wt %. In yet another embodiment of the present invention, the wall material comprises aluminum in an amount between about 1 wt % and about 4 wt %. In even yet another embodiment of the present invention, the wall material comprises aluminum in an amount between about 3 wt % and about 5 wt %.

In one embodiment of the present invention, the wall material comprises silicon in an amount greater than about 1 wt %. In another embodiment of the present invention, the wall material comprises silicon in an amount greater than about 2 wt %. In yet another embodiment of the present invention, the wall material comprises silicon in an amount greater than about 3 wt %. In even yet another embodiment of the present invention, the wall material comprises silicon in an amount greater than about 4 wt %. In one embodiment of the present invention, the wall material comprises silicon in an amount between about 1 wt % and about 50 wt %. In another embodiment of the present invention, the wall material comprises silicon in an amount between about 1 wt % and about 6 wt %. In yet another embodiment of the present invention, the wall material comprises silicon in an amount between about 3 wt % and about 5 wt %.

In one embodiment of the present invention, the wall material further comprises nickel in an amount between about 50 wt % and about 75 wt %. In another embodiment of the present invention, the wall material further comprises chromium in an amount between about 15 wt % and about 20 wt %. In yet another embodiment of the present invention, the wall material further comprises iron in an amount between about 3 wt % and about 30 wt %. In even yet another embodiment of the present invention, the wall material further comprises nickel in an amount between about 50 wt % and about 75 wt %, chromium in an amount between about 15 wt % and about 20 wt %, and iron in an amount between about 3 wt % and about 30 wt %. In one embodiment of the present invention, the wall material comprises aluminum in an amount greater than about 1 wt %, nickel in an amount between about 50 wt % and about 75 wt %, chromium in an amount between about 15 wt % and about 20 wt %, and iron in an amount between about 3 wt % and about 30 wt %. Non-limiting examples of commercial wall materials with compositions within the above disclosure are HAYNES® 214® and HAYNES® HR-224® alloys from Haynes International, Inc. (Kokomo, Ind.).

In one embodiment of the present invention, the wall material further comprises nickel in an amount of about 60 wt %. In another embodiment of the present invention, the wall material further comprises chromium in an amount between about 20 wt % and about 30 wt %. In yet another embodiment of the present invention, the wall material further comprises iron in an amount between about 3 wt % and about 20 wt %. In even yet another embodiment of the present invention, the wall material further comprises nickel in an amount of about 60 wt %, chromium in an amount between about 20 wt % and about 30 wt %, and iron in an amount between about 3 wt % and about 20 wt %. In one embodiment of the present invention, the wall material comprises aluminum in an amount greater than about 1 wt %, nickel in an amount of about 60 wt %, chromium in an amount between about 20 wt % and about 30 wt %, and iron in an amount between about 3 wt % and about 20 wt %. Non-limiting examples of commercial wall materials with compositions within the above disclosure are INCONEL® alloy 693 and INCONEL® alloy 601 from Special Metals Corporation (Huntington, W. Va.).

In one embodiment of the present invention, the wall material further comprises iron in an amount of about 70 wt %. In another embodiment of the present invention, the wall material further comprises chromium in an amount of about 22 wt %. In yet another embodiment of the present invention, the wall material further comprises iron in an amount of about 70 wt % and chromium in an amount of about 22 wt %. In even yet another embodiment of the present invention, the wall material comprises aluminum in an amount greater than about 1 wt %, iron in an amount of about 70 wt %, and chromium in an amount of about 22 wt %. Non-limiting examples of commercial wall materials with compositions within the above disclosure are KANTHAL APM and KANTHAL APMT from Sandvik AB (Stockholm, Sweden); and INCOLLOY® alloy MA956 (Fe—Cr—Al alloy) from Special Metals Corporation (Huntington, W. Va.).

In one embodiment of the present invention, the wall material further comprises nickel in an amount between about 10 wt % and about 65 wt %. In another embodiment of the present invention, the wall material further comprises chromium in an amount between about 15 wt % and about 30 wt %. In yet another embodiment of the present invention, the wall material further comprises iron in an amount between about 2 wt % and about 65 wt %. In even yet another embodiment of the present invention, the wall material comprises silicon in an amount greater than about 1 wt %, nickel in an amount between about 10 wt % and about 65 wt %, chromium in an amount between about 15 wt % and about 30 wt %, and iron in an amount between about 2 wt % and about 65 wt %. Non-limiting examples of commercial wall materials with compositions within the above disclosure are Sandvik SX and Sandvik 253 MA from Sandvik AB (Stockholm, Sweden), and HAYNES® HR-160® and HASTELLOY® D-205 alloys from Haynes International, Inc. (Kokomo, Ind.).

Figure 4:
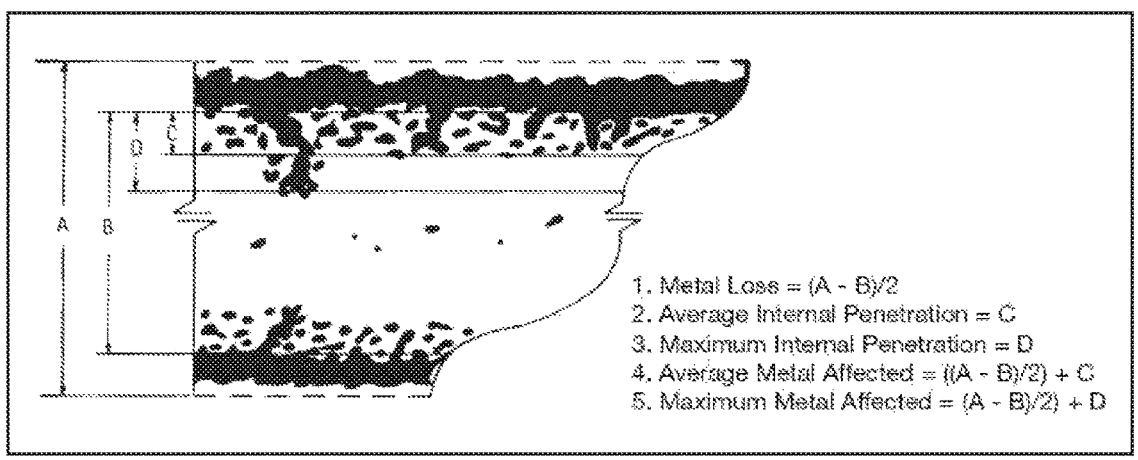
FIG. 4 is a schematic of a metallographic technique used by Haynes International, Inc. (Kokomo, Ind.) to estimate the corrosion rate of coupons exposed to various environments.

In one embodiment of the present invention, the single-layer reactor has a corrosion rate lower than about 1.3 mm/y. In another embodiment of the present invention, the bi-layer reactor has a corrosion rate lower than about 1.3 mm/y. For the purposes of the present invention, the corrosion rate is measured using a metallographic technique as shown in FIG. 4 (copied from a Haynes International, Inc., brochure). More specifically in this technique (known to those skilled in the art), a test metal coupon is embedded in the catalyst bed and the dehydration reaction proceeds for a period of TOS (in h). After the dehydration reaction stops, the metal coupon is removed from the catalyst bed and subjected to a typical metallographic analysis, that includes mounting the sample in a thermosetting resin, curing the resin, grinding the sample to reveal its surface, and SEM analysis of the sample to calculate the metal loss [(A−B)/2] in mm, as shown in FIG. 4. Then, the corrosion rate (CR) in mm per year (mm/y) is calculated as CR={[(A−B)/2]*24*365}/TOS, where 24 refers to the hours per day and 365 refers to the days per year. Note that this equation assumes that the corrosion observed over TOS (typically a few hours to about 72 hours) linearly extrapolates out to a year, which is not necessarily accurate.

In one embodiment of the present invention, said corrosion rate is lower than about 1 mm/y. In another embodiment of the present invention, said corrosion rate is lower than about 0.5 mm/y. In yet another embodiment of the present invention, said corrosion rate is lower than about 0.13 mm/y. In even yet another embodiment of the present invention, said corrosion rate is lower than about 0.05 mm/y.

In one embodiment of the present invention, said corrosion resistant reactor metal has a standard free energy of formation of oxides greater than about 700 kJ/mol $O_2$ at about 400° C. The standard free energy of formation of oxides can be found in the Ellingham diagram, as it is well known to those skilled in the art. In another embodiment of the present invention, said corrosion resistant reactor metal has a standard free energy of formation of oxides greater than about 950 kJ/mol $O_2$ at about 400° C. In yet another embodiment of the present invention, said corrosion resistant reactor metal has a standard free energy of formation of oxides greater than about 1050 kJ/mol $O_2$ at about 400° C. In even yet another embodiment of the present invention, said corrosion resistant reactor metal is selected from the group consisting of Ca, Mg, and mixtures thereof.

In one embodiment of the present invention, said corrosion resistant reactor metal has a voltage potential, with respect to the standard hydrogen electrode (SHE), less than about 0.2 V at about 25° C., pH less than about 7, and concentration of the oxidized species of about $10^{-6}$ mol/kg in water. The voltage potential of the reactor metal can be found in the Pourbaix diagram of the metal or it can be estimated using the Nernst equation, as it is well known to those skilled in the art. In another embodiment of the present invention, said corrosion resistant reactor metal has a voltage potential, with respect to the standard hydrogen electrode (SHE), less than about 0 V at about 25° C., pH less than about 7, and concentration of the oxidized species of about $10^{-6}$ mol/kg in water. In yet another embodiment of the present invention, said corrosion resistant reactor metal has a voltage potential, with respect to the standard hydrogen electrode (SHE), between about 0.2 V and about −0.3 V at about 25° C., pH less than about 7, and concentration of the oxidized species of about $10^{-6}$ mol/kg in water.

In one embodiment of the present invention, the temperature during said dehydration is greater than about 100° C. In another embodiment of the present invention, the temperature during said dehydration is between about 120° C. and about 700° C. In yet another embodiment of the present invention, the temperature during said dehydration is between about 150° C. and about 500° C. In even yet another embodiment of the present invention, the temperature during said dehydration is between about 300° C. and about 450° C. In one embodiment of the present invention, the temperature during said dehydration is between about 325° C. and about 400° C. In another embodiment of the present invention, the temperature during said dehydration is about 350° C. In yet another embodiment of the present invention, the temperature during said dehydration is about 375° C. In even yet another embodiment of the present invention, the temperature during said dehydration is equal to or greater than the triple point temperature of said catalyst. In one embodiment of the present invention, the temperature during said dehydration is at least 10° C. higher than the triple point temperature of said catalyst. In another embodiment of the present invention, the temperature during said dehydration is at least 50° C. higher than the triple point temperature of said catalyst. In yet another embodiment of the present invention, the temperature during said dehydration is at least 100° C. higher than the triple point temperature of said catalyst.

In one embodiment of the present invention, said water partial pressure during said dehydration is equal to or greater than about 0.4 bar. In another embodiment of the present invention, said water partial pressure during said dehydration is equal to or greater than about 0.8 bar. In yet another embodiment of the present invention, said water partial pressure during said dehydration is equal to or greater than about 4 bar. In even yet another embodiment of the present invention, said water partial pressure during said dehydration is between about 5 bar and about 35 bar. In one embodiment of the present invention, said water partial pressure during said dehydration is about 13 bar. In one embodiment of the present invention, the water partial pressure during said dehydration is equal to or greater than the triple point water partial pressure of said catalyst. In another embodiment of the present invention, the water partial pressure during said dehydration is at least 1 bar greater than the triple point water partial pressure of said catalyst. In yet another embodiment of the present invention, the water partial pressure during said dehydration is at least 2 bar greater than the triple point water partial pressure of said catalyst. In even yet another embodiment of the present invention, the water partial pressure during said dehydration is at least 5 bar greater than the triple point water partial pressure of said catalyst.

The dehydration can be performed under vacuum, at atmospheric pressure, or at higher pressure than atmospheric. In one embodiment of the present invention, the dehydration is performed under a total pressure of at least about 1 bar. In another embodiment of the present invention, the dehydration is performed under a total pressure between about 2 bar and about 100 bar. In yet another embodiment of the present invention, the dehydration is performed under a total pressure between about 5 bar and about 40 bar. In even yet another embodiment of the present invention, the dehydration is performed under a total pressure between about 10 bar and about 35 bar. In one embodiment of the present invention, the dehydration is performed under a total pressure of about 1.6 bar. In another embodiment of the present invention, the dehydration is performed under a total pressure of about 8 bar. In yet another embodiment of the present invention, the dehydration is performed under a total pressure of about 26 bar.

In one embodiment of the present invention, said GHSV in the dehydration is between about 720 $h^{-1}$ and about 36,000 $h^{-1}$. In another embodiment of the present invention, said GHSV is between about 1,440 $h^{-1}$ and about 18,000 $h^{-1}$. In yet another embodiment of the present invention, said GHSV is between about 2,300 $h^{-1}$ and about 6,000 $h^{-1}$. In even yet another embodiment of the present invention, said GHSV is between about 2,300 $h^{-1}$ and about 3,600 $h^{-1}$. In one embodiment of the present invention, said GHSV is about 2,300 $h^{-1}$. In another embodiment of the present invention, said GHSV is about 3,600 $h^{-1}$.

In one embodiment of the present invention, said WHSV is between about 0.02 $h^{-1}$ and about 10 $h^{-1}$. In another embodiment of the present invention, said WHSV is between about 0.2 $h^{-1}$ and about 2 $h^{-1}$. In yet another embodiment of the present invention, said WHSV is between about 0.3 $h^{-1}$ and about 1.4 $h^{-1}$. In even yet another embodiment of the present invention, said WHSV is between about 0.3 $h^{-1}$ and about 0.4 $h^{-1}$. In one embodiment of the present invention, said WHSV is about 0.4 $h^{-1}$.

In the context of the present invention, "contacting" refers to the action of bringing said gas feed stream comprising water vapor and hydroxypropionic acid, hydroxypropionic acid derivatives, or mixtures thereof in close proximity to the surface of said catalyst. The hydroxypropionic acid, hydroxypropionic acid derivatives, or mixtures thereof must contact the surface of the catalyst at a rate that is slow enough for the dehydration reaction to occur, yet fast enough to avoid the degradation of hydroxypropionic acid, acrylic acid, or their derivatives to undesirable products at the temperature of said contacting step. Several parameters can be used to describe the rate of said contacting step, such as, by way of example and not limitation, WHSV, GHSV, LHSV, and weight velocity per unit of accessible catalyst surface area (WVSA) that can be calculated as the ratio of WHSV and the catalyst specific surface area (SA), (WVSA=WHSV/SA); with units: g/m$^2$·h; where g refer to g of hydroxypropionic acid, hydroxypropionic acid derivatives, or mixtures thereof. A number of methods, based on the adsorption of an inert gas, can be used to determine the accessible surface area, including, but not limited to, the static volumetric and gravimetric methods and the dynamic method that are well-known by those skilled in the art.

In one embodiment of the present invention, the hydroxypropionic acid, hydroxypropionic acid derivatives, or mixtures thereof contact the catalyst at a WVSA between about $10^{-4}$ g·m$^{-2}$·h$^{-1}$ and about $10^4$ g·m$^{-2}$·h$^{-1}$. In another embodiment of the present invention, the hydroxypropionic acid, hydroxypropionic acid derivatives, or mixtures thereof contact the catalyst at a WVSA between about $10^{-2}$ g·m$^{-2}$·h$^{-1}$ and about $10^2$ g·m$^{-2}$·h$^{-1}$. In yet another embodiment of the present invention, the hydroxypropionic acid, hydroxypropionic acid derivatives, or mixtures thereof contact the catalyst at a WVSA between about 0.1 g·m$^{-2}$·h$^{-1}$ and about 10 g·m$^{-2}$·h$^{-1}$.

In one embodiment of the present invention, said hydroxypropionic acid is lactic acid; wherein said gas feed stream comprises a diluent; wherein said diluent consists essentially of nitrogen; wherein said temperature is between about 300° C. and about 450° C.; wherein said water partial pressure is equal to or greater than about 0.8 bar; and wherein said GHSV is between about 2,300 h$^{-1}$ and about 3,600 h$^{-1}$, and said WHSV is between about 0.2 h$^{-1}$ and about 2 h$^{-1}$.

In one embodiment of the present invention, the TOS is longer than about 2 h. In another embodiment of the present invention, the TOS is between about 2 h and about 24 h. In yet another embodiment of the present invention, the TOS is between about 24 h and about 48 h. In even yet another embodiment of the present invention, the TOS is between about 24 h and about 72 h. In one embodiment of the present invention, the TOS is about 72 h. In another embodiment of the present invention, the TOS is longer than about 1000 h. In yet another embodiment of the present invention, the TOS is about 1 year.

In one embodiment of the present invention, said acrylic acid, acrylic acid derivatives, or mixtures thereof are produced with a yield of at least 50 mol %. In another embodiment of the present invention, said acrylic acid, acrylic acid derivatives, or mixtures thereof are produced with a yield of at least about 70%. In yet another embodiment of the present invention, said acrylic acid, acrylic acid derivatives, or mixtures thereof are produced with a yield of at least about 80 mol %.

In one embodiment of the present invention, said acrylic acid, acrylic acid derivatives, or mixtures thereof are produced with a selectivity of at least about 50 mol %. In another embodiment of the present invention, said acrylic acid, acrylic acid derivatives, or mixtures thereof are produced with a selectivity of at least about 70 mol %. In yet another embodiment of the present invention, said acrylic acid, acrylic acid derivatives, or mixtures thereof are produced with a selectivity of at least about 80 mol %.

In one embodiment of the present invention, said acrylic acid, acrylic acid derivatives, or mixtures thereof are produced with a yield of at least about 70 mol % and with a selectivity of at least about 70 mol %. In another embodiment of the present invention, said acrylic acid, acrylic acid derivatives, or mixtures thereof are produced with a yield of at least about 80 mol % and with a selectivity of at least about 80 mol %.

In one embodiment of the present invention, propionic acid is produced as an impurity along with said acrylic acid, acrylic acid derivatives, or mixtures thereof; and wherein the selectivity of said propionic acid is less than about 5 mol %. In another embodiment of the present invention, propionic acid is produced as an impurity along with said acrylic acid, acrylic acid derivatives, or mixtures thereof; and wherein the selectivity of said propionic acid is less than about 1 mol %.

In one embodiment of the present invention, said acrylic acid, acrylic acid derivatives, or mixtures thereof are produced with a yield of at least about 70 mol % and with a selectivity of at least about 70 mol % over a TOS of about 72 h; wherein propionic acid is produced as an impurity along with said acrylic acid, acrylic acid derivatives, or mixtures thereof; and wherein the selectivity of said propionic acid is less than about 5 mol % over said TOS of about 72 h. In another embodiment of the present invention, said acrylic acid, acrylic acid derivatives, or mixtures thereof are produced with a yield of at least about 80 mol % and with a selectivity of at least about 80 mol % over a TOS of about 72 h; wherein propionic acid is produced as an impurity along with said acrylic acid, acrylic acid derivatives, or mixtures thereof; and wherein the selectivity of said propionic acid is less than about 1 mol % over said TOS of about 72 h.

In one embodiment of the present invention, said acrylic acid, acrylic acid derivatives, or mixtures thereof are produced with a conversion of said hydroxypropionic acid, hydroxypropionic acid derivatives, or mixtures thereof of more than about 50 mol %. In another embodiment of the present invention, said acrylic acid, acrylic acid derivatives, or mixtures thereof are produced with a conversion of said hydroxypropionic acid, hydroxypropionic acid derivatives, or mixtures thereof of more than about 80 mol %.

In one embodiment of the present invention, acetic acid, pyruvic acid, 1,2-propanediol, hydroxyacetone, acrylic acid dimer, and 2,3-pentanedione are produced along with said acrylic acid, acrylic acid derivatives, or mixtures thereof with a yield of less than about 2 mol % each. In another embodiment of the present invention, acetic acid, pyruvic acid, 1,2-propanediol, hydroxyacetone, acrylic acid dimer, and 2,3-pentanedione are produced along with said acrylic acid, acrylic acid derivatives, or mixtures thereof with a yield of less than about 0.5 mol % each. In yet another embodiment of the present invention, acetaldehyde is produced along with said acrylic acid, acrylic acid derivatives, or mixtures thereof with a yield of less than about 8 mol %. In even yet another embodiment of the present invention, acetaldehyde is produced along with said acrylic acid, acrylic acid derivatives, or mixtures thereof with a yield of less than about 4 mol %. In one embodiment of the present invention, acetaldehyde is produced along with said acrylic acid, acrylic acid derivatives, or mixtures thereof with a yield of less than about 3 mol %.

In one embodiment of the present invention, said phosphate salt is crystalline; wherein said x is 1; wherein said cation is K$^+$; wherein said wall material further comprises nickel in an amount between about 50 wt % and about 75 wt %, chromium in an amount between about 15 wt % and about 20 wt %, and iron in an amount between about 3 wt % and about 30%; wherein said amount of said aluminum is between about 3 wt % and about 5 wt %; wherein said hydroxypropionic acid is lactic acid; wherein said temperature is about 375° C. and said water partial pressure is about 13 bar; wherein said GHSV is about 2,300 h$^{-1}$ and said WHSV is between about 0.3 h$^{-1}$ and about 0.4 h$^{-1}$; wherein said acrylic acid, acrylic acid derivatives, or mixtures thereof are produced with a yield of at least about 80% and with a selectivity of at least about 80% over a TOS of about 72 h; wherein propionic acid is produced as an impurity along with said acrylic acid, acrylic acid derivatives, or mixtures thereof; and wherein the selectivity of said propionic acid is less than about 1 mol % over said TOS of about 72 h.

In another embodiment of the present invention, said phosphate salt is crystalline; wherein said x is 1; wherein said cation is $Cs^+$; wherein said wall material further comprises nickel in an amount between about 50 wt % and about 75 wt %, chromium in an amount between about 15 wt % and about 20 wt %, and iron in an amount between about 3 wt % and about 30%; wherein said amount of said aluminum is between about 3 wt % and about 5 wt %; wherein said hydroxypropionic acid is lactic acid; wherein said temperature is about 375° C. and said water partial pressure is about 13 bar; wherein said GHSV is about 2,300 $h^{-1}$ and said WHSV is between about 0.3 $h^{-1}$ and about 0.4 $h^{-1}$; wherein said acrylic acid, acrylic acid derivatives, or mixtures thereof are produced with a yield of at least about 80% and with a selectivity of at least about 80% over a TOS of about 72 h; wherein propionic acid is produced as an impurity along with said acrylic acid, acrylic acid derivatives, or mixtures thereof; and wherein the selectivity of said propionic acid is less than about 1 mol % over said TOS of about 72 h.

In yet another embodiment of the present invention; said phosphate salt is crystalline; wherein said x is 1; wherein said cation is $K^+$; wherein said wall material further comprises nickel in an amount of about 60 wt %, chromium in an amount between about 20 wt % and about 30 wt %, and iron in an amount between about 3 wt % and about 20 wt %; wherein said amount of said aluminum is between about 1 wt % and about 4 wt %; wherein said hydroxypropionic acid is lactic acid; wherein said temperature is about 375° C. and said water partial pressure is about 13 bar; wherein said GHSV is about 2,300 $h^{-1}$ and said WHSV is between about 0.3 $h^{-1}$ and about 0.4 $h^{-1}$; wherein said acrylic acid, acrylic acid derivatives, or mixtures thereof are produced with a yield of at least about 80% and with a selectivity of at least about 80% over a TOS of about 72 h; wherein said acrylic acid, acrylic acid derivatives, or mixtures thereof are produced with a yield of at least about 80 mol % and with a selectivity of at least about 80 mol % over a TOS of about 72 h; wherein propionic acid is produced as an impurity along with said acrylic acid, acrylic acid derivatives, or mixtures thereof; and wherein the selectivity of said propionic acid is less than about 1 mol % over said TOS of about 72 h.

In even yet another embodiment of the present invention; said phosphate salt is crystalline; wherein said x is 1; wherein said cation is $Cs^+$; wherein said wall material further comprises nickel in an amount of about 60 wt %, chromium in an amount between about 20 wt % and about 30 wt %, and iron in an amount between about 3 wt % and about 20 wt %; wherein said amount of said aluminum is between about 1 wt % and about 4 wt %; wherein said hydroxypropionic acid is lactic acid; wherein said temperature is about 375° C. and said water partial pressure is about 13 bar; wherein said GHSV is about 2,300 $h^{-1}$ and said WHSV is between about 0.3 $h^{-1}$ and about 0.4 $h^{-1}$; wherein said acrylic acid, acrylic acid derivatives, or mixtures thereof are produced with a yield of at least about 80% and with a selectivity of at least about 80% over a TOS of about 72 h; wherein said acrylic acid, acrylic acid derivatives, or mixtures thereof are produced with a yield of at least about 80 mol % and with a selectivity of at least about 80 mol % over a TOS of about 72 h; wherein propionic acid is produced as an impurity along with said acrylic acid, acrylic acid derivatives, or mixtures thereof; and wherein the selectivity of said propionic acid is less than about 1 mol % over said TOS of about 72 h.

In one embodiment of the present invention, a method of making acrylic acid, acrylic acid derivatives, or mixtures thereof comprises contacting a gas feed stream comprising water vapor and hydroxypropionic acid, hydroxypropionic acid derivatives, or mixtures thereof with a catalyst in a single-layer reactor at a temperature, a water partial pressure, a GHSV, and a WHSV to dehydrate said hydroxypropionic acid, hydroxypropionic acid derivatives, or mixtures thereof; wherein said catalyst comprises a phosphate salt comprising a cation and an anion represented by the empirical formula $[H_{2(1-x)}PO_{(4-x)}]^-$; wherein x is any real number greater than or equal to 0 and less than or equal to 1; wherein said water partial pressure is equal to or greater than about 0.4 bar; wherein said single-layer reactor comprises a wall, an outer surface, and an inner surface; wherein said wall is made from a wall material, has a wall thickness, and extends from said outer surface to said inner surface; wherein said wall material comprises aluminum in an amount greater than about 1 wt %; wherein said inner surface is in contact with said catalyst; wherein said single-layer reactor has a corrosion rate lower than about 1.3 mm/y during said dehydration; and whereby acrylic acid, acrylic acid derivatives, or mixtures thereof are produced as a result of said dehydration in said single-layer reactor.

In another embodiment of the present invention, a method of making acrylic acid, acrylic acid derivatives, or mixtures thereof comprises contacting a gas feed stream comprising water vapor and lactic acid, lactic acid derivatives, or mixtures thereof with a catalyst in a single-layer reactor at a temperature, a water partial pressure, a GHSV, and a WHSV to dehydrate said lactic acid, lactic acid derivatives, or mixtures thereof; wherein said catalyst comprises a phosphate salt comprising a monovalent cation and an anion represented by the empirical formula $[H_{2(1-x)}PO_{(4-x)}]^-$; wherein x is any real number greater than or equal to 0 and less than or equal to 1; wherein said cation is selected from the group consisting of $K^+$, $Cs^+$, and mixtures thereof; wherein said temperature is between about 300° C. and about 450° C.; wherein said water partial pressure is equal to or greater than about 0.4 bar; wherein said GHSV is about 2,300 $h^{-1}$; wherein said WHSV is between about 0.3 $h^{-1}$ and about 0.4 $h^{-1}$; wherein said single-layer reactor comprises a wall, an outer surface, and an inner surface; wherein said wall is made from a wall material, has a wall thickness, and extends from said outer surface to said inner surface; wherein said wall material comprises aluminum in an amount greater than about 1 wt %; wherein said inner surface is in contact with said catalyst; wherein said single-layer reactor has a corrosion rate lower than about 1.3 mm/y during said dehydration; wherein said acrylic acid, acrylic acid derivatives, or mixtures thereof are produced with a yield of at least about 80 mol % and with a selectivity of at least about 80 mol % over a TOS of about 72 h; wherein propionic acid is produced as an impurity along with said acrylic acid, acrylic acid derivatives, or mixtures thereof; and wherein the selectivity of said propionic acid is less than about 1 mol % over said TOS of about 72 h.

In yet another embodiment of the present invention, a method of making acrylic acid, acrylic acid derivatives, or mixtures thereof comprises contacting a gas feed stream comprising water vapor and hydroxypropionic acid, hydroxypropionic acid derivatives, or mixtures thereof with a catalyst in a single-layer reactor at a temperature, a water partial pressure, a GHSV, and a WHSV to dehydrate said hydroxypropionic acid, hydroxypropionic acid derivatives, or mixtures thereof; wherein said catalyst comprises a phosphate salt comprising a cation and an anion represented by the empirical formula $[H_{2(1-x)}PO_{(4-x)}]^-$; wherein x is any real number greater than or equal to 0 and less than or equal to 1; wherein said water partial pressure is equal to or greater than about 0.4 bar; wherein said single-layer reactor comprises a wall, an outer surface, and an inner surface; wherein said wall is made from a wall material, has a wall thickness, and extends from said outer surface to said inner surface; wherein said wall material comprises silicon in an amount greater than about 1 wt %; wherein said inner surface is in contact with said catalyst; wherein said single-layer reactor has a corrosion rate lower than about 1.3 mm/y during said dehydration; and whereby acrylic acid, acrylic acid derivatives, or mixtures thereof are produced as a result of said dehydration in said single-layer reactor.

In even yet another embodiment of the present invention, a method of making acrylic acid, acrylic acid derivatives, or mixtures thereof comprises contacting a gas feed stream comprising water vapor and hydroxypropionic acid, hydroxypropionic acid derivatives, or mixtures thereof with a catalyst in a bi-layer reactor at a temperature, a water partial pressure, a GHSV, and a WHSV to dehydrate said hydroxypropionic acid, hydroxypropionic acid derivatives, or mixtures thereof; wherein said catalyst comprises a phosphate salt comprising a cation and an anion represented by the empirical formula $[H_{2(1-x)}PO_{(4-x)}]^-$; wherein x is any real number greater than or equal to 0 and less than or equal to 1; wherein said water partial pressure is equal to or greater than about 0.4 bar; wherein said bi-layer reactor comprises an outer layer, an inner layer, an outer surface, an inner surface, and an interface between said outer layer and said inner layer; wherein said outer layer is made from an outer layer material, has an outer layer thickness, and extends from said interface to said outer surface; wherein said inner layer is made from an inner layer material, has an inner layer thickness, and extends from said inner surface to said interface; wherein said inner layer material is selected from the group consisting of aluminum, silicon, copper, silver, gold, titanium, tantalum, tungsten, molybdenum, platinum, palladium, zirconium, and mixtures thereof; wherein said inner surface is in contact with said catalyst; wherein said bi-layer reactor has a corrosion rate lower than about 1.3 mm/y during said dehydration; and whereby acrylic acid, acrylic acid derivatives, or mixtures thereof are produced as a result of said dehydration in said bi-layer reactor.

In one embodiment of the present invention, said gas feed stream comprising water vapor and hydroxypropionic acid, hydroxypropionic acid derivatives, or mixtures thereof is produced by contacting a liquid feed stream comprising hydroxypropionic acid, hydroxypropionic acid derivatives, or mixtures thereof with water vapor. In another embodiment of the present invention, said gas feed stream comprising water vapor and lactic acid, lactic acid derivatives, or mixtures thereof is produced by contacting a liquid feed stream comprising lactic acid, lactic acid derivatives, or mixtures thereof with water vapor. In yet another embodiment of the present invention, said liquid feed stream comprising hydroxypropionic acid, hydroxypropionic acid derivatives, or mixtures thereof can further comprise one or more essentially chemically inert liquids. Non-limiting examples of essentially chemically inert liquids are water, hydrocarbons, chlorinated hydrocarbons, fluorinated hydrocarbons, brominated hydrocarbons, esters, ethers, ketones, aldehydes, acids, alcohols, or mixtures thereof. Non-limiting examples of hydrocarbons are C5 to C8 linear and branched alkanes. A non-limiting example of esters is ethyl acetate. A non-limiting example of ethers is diphenyl ether. A non-limiting example of ketones is acetone. Non-limiting examples of alcohols are methanol, ethanol, and C3 to C8 linear and branched alcohols. In one embodiment of the present invention, said one or more essentially chemically inert liquids comprise water. In one embodiment of the present invention, said one or more essentially chemically inert liquids consists essentially of water.

In one embodiment of the present invention, a liquid feed stream comprising water and hydroxypropionic acid, hydroxypropionic acid derivatives, or mixtures thereof is fed into an evaporator upstream of the catalytic reactor for the liquid feed stream to become a gas feed stream comprising water vapor and hydroxypropionic acid, hydroxypropionic acid derivatives, or mixtures thereof, at least partially, before contacting said catalyst. In another embodiment of the present invention, a liquid feed stream comprising water and hydroxypropionic acid, hydroxypropionic acid derivatives, or mixtures thereof is fed directly into the catalytic reactor and contacted with said catalyst. In yet another embodiment of the present invention, an essentially chemically inert gas or an essentially chemically inert liquid is fed into the evaporator or into the catalytic reactor. The liquid feed stream comprising hydroxypropionic acid, hydroxypropionic acid derivatives, or mixtures thereof and the essentially chemically inert gas or the essentially chemically inert liquid can be jointly or separately fed into said evaporator or said catalytic reactor. Non-limiting examples of essentially chemically inert gases are nitrogen, helium, air, argon, carbon dioxide, carbon monoxide, water vapor, and mixtures thereof. Non-limiting examples of essentially chemically inert liquids are water, hydrocarbons, chlorinated hydrocarbons, fluorinated hydrocarbons, brominated hydrocarbons, esters, ethers, ketones, aldehydes, acids, alcohols, or mixtures thereof.

In one embodiment of the present invention, a method of making acrylic acid, acrylic acid derivatives, or mixtures thereof comprises: a) providing a liquid feed stream comprising hydroxypropionic acid, hydroxypropionic acid derivatives, or mixtures thereof; b) optionally combining said liquid feed stream with an essentially chemically inert gas to form a liquid/gas blend; and c) contacting said catalyst feed stream or said liquid/gas blend with any catalyst disclosed in Section II ("Active Catalysts for the Dehydration of Hydroxypropionic Acid or its Derivatives to Acrylic Acid or its Derivatives") or any precursor catalyst disclosed in Section III ("Precursor Catalysts for the Dehydration of Hydroxypropionic Acid or its Derivatives to Acrylic Acid or its Derivatives") of the present invention under a water partial pressure of about 0.4 bar or more to produce said acrylic acid, acrylic acid derivatives, or mixtures thereof.

In another embodiment of the present invention, a method of making acrylic acid, acrylic acid derivatives, or mixtures thereof comprises: a) providing a liquid feed stream comprising an aqueous solution of hydroxypropionic acid, hydroxypropionic acid derivatives, or mixtures thereof; b) optionally combining said liquid feed stream with an essentially chemically inert gas to form a liquid/gas blend; and c) contacting said liquid feed stream or said liquid/gas blend with any catalyst disclosed in Section II ("Active Catalysts for the Dehydration of Hydroxypropionic Acid or its Derivatives to Acrylic Acid or its Derivatives") or any precursor catalyst disclosed in Section III ("Precursor Catalysts for the Dehydration of Hydroxypropionic Acid or its Derivatives to Acrylic Acid or its Derivatives") of the present invention under a water partial pressure of about 0.4 bar or more to produce said acrylic acid, acrylic acid derivatives, or mixtures thereof.

In yet another embodiment of the present invention, a method of making acrylic acid, acrylic acid derivatives, or mixtures thereof comprises: a) providing a liquid feed stream comprising an aqueous solution of hydroxypropionic acid, hydroxypropionic acid derivatives, or mixtures thereof; b) optionally combining said liquid feed stream with an essentially chemically inert gas to form a liquid/gas blend; c) evaporating said liquid feed stream or said liquid/gas blend to produce a gas feed stream; and d) contacting said gas feed stream with any catalyst disclosed in Section II ("Active Catalysts for the Dehydration of Hydroxypropionic Acid or its Derivatives to Acrylic Acid or its Derivatives") or any precursor catalyst disclosed in Section III ("Precursor Catalysts for the Dehydration of Hydroxypropionic Acid or its Derivatives to Acrylic Acid or its Derivatives") of the present invention under a water partial pressure of about 0.4 bar or more to produce said acrylic acid, acrylic acid derivatives, or mixtures thereof.

In even yet another embodiment of the present invention, a method of making acrylic acid, acrylic acid derivatives, or mixtures thereof comprises: a) providing a liquid feed stream comprising an aqueous solution of hydroxypropionic acid, hydroxypropionic acid derivatives, or mixtures thereof; wherein the hydroxypropionic acid is essentially in monomeric form in the aqueous solution; b) optionally combining said liquid feed stream with an essentially chemically inert gas to form a liquid/gas blend; c) evaporating said liquid feed stream or said liquid/gas blend to produce a gas feed stream; and d) contacting said gas feed stream with any catalyst disclosed in Section II ("Active Catalysts for the Dehydration of Hydroxypropionic Acid or its Derivatives to Acrylic Acid or its Derivatives") or any precursor catalyst disclosed in Section III ("Precursor Catalysts for the Dehydration of Hydroxypropionic Acid or its Derivatives to Acrylic Acid or its Derivatives") of the present invention under a water partial pressure of about 0.4 bar or more to produce said acrylic acid, acrylic acid derivatives, or mixtures thereof.

In one embodiment of the present invention, a method of making acrylic acid, acrylic acid derivatives, or mixtures thereof comprises: a) providing a liquid feed stream comprising an aqueous solution of hydroxypropionic acid, hydroxypropionic acid derivatives, or mixtures thereof; wherein the hydroxypropionic acid is essentially in monomeric form in the aqueous solution, and wherein the hydroxypropionic acid, hydroxypropionic acid derivatives, or mixtures thereof comprise between about 10 wt % and about 25 wt % of the aqueous solution; b) optionally combining said liquid feed stream with an essentially chemically inert gas to form a liquid/gas blend; c) evaporating said liquid feed stream or said liquid/gas blend to produce a gas feed stream; and d) contacting said gas feed stream with any catalyst disclosed in Section II ("Active Catalysts for the Dehydration of Hydroxypropionic Acid or its Derivatives to Acrylic Acid or its Derivatives") or any precursor catalyst disclosed in Section III ("Precursor Catalysts for the Dehydration of Hydroxypropionic Acid or its Derivatives to Acrylic Acid or its Derivatives") of the present invention under a water partial pressure of about 0.4 bar or more to produce said acrylic acid, acrylic acid derivatives, or mixtures thereof.

In another embodiment of the present invention, a method of making acrylic acid, acrylic acid derivatives, or mixtures thereof comprises: a) providing a liquid feed stream comprising an aqueous solution of hydroxypropionic acid, hydroxypropionic acid derivatives, or mixtures thereof; wherein the hydroxypropionic acid comprises oligomers in the aqueous solution; b) heating said liquid feed stream at a temperature between about 50° C. and about 100° C. to hydrolyze the oligomers of the hydroxypropionic acid and produce a liquid feed stream comprising monomeric hydroxypropionic acid; c) optionally combining said liquid feed stream comprising monomeric hydroxypropionic acid with an essentially chemically inert gas to form a liquid/gas blend; d) evaporating said liquid feed stream comprising monomeric hydroxypropionic acid or said liquid/gas blend to produce a gas feed stream; and e) contacting said gas feed stream with any catalyst disclosed in Section II ("Active Catalysts for the Dehydration of Hydroxypropionic Acid or its Derivatives to Acrylic Acid or its Derivatives") or any precursor catalyst disclosed in Section III ("Precursor Catalysts for the Dehydration of Hydroxypropionic Acid or its Derivatives to Acrylic Acid or its Derivatives") of the present invention under a water partial pressure of about 0.4 bar or more to produce said acrylic acid, acrylic acid derivatives, or mixtures thereof.

In yet another embodiment of the present invention, a method of making acrylic acid, acrylic acid derivatives, or mixtures thereof comprises: a) providing a liquid feed stream comprising an aqueous solution of hydroxypropionic acid, hydroxypropionic acid derivatives, or mixtures thereof; b) optionally combining the liquid feed stream with an essentially chemically inert gas to form a liquid/gas blend; c) evaporating said liquid feed stream or said liquid/gas blend to produce a gas feed stream; d) contacting said gas feed stream with any catalyst disclosed in Section II ("Active Catalysts for the Dehydration of Hydroxypropionic Acid or its Derivatives to Acrylic Acid or its Derivatives") or any precursor catalyst disclosed in Section III ("Precursor Catalysts for the Dehydration of Hydroxypropionic Acid or its Derivatives to Acrylic Acid or its Derivatives") of the present invention under a water partial pressure of about 0.4 bar or more to produce an acrylic acid stream; and e) cooling said acrylic acid stream to produce a liquid acrylic acid stream comprising said acrylic acid, acrylic acid derivatives, or mixtures thereof.

In one embodiment of the present invention, the concentration of the hydroxypropionic acid, hydroxypropionic acid derivatives, or mixtures thereof in said liquid feed stream is between about 2 wt % and about 95 wt %. In another embodiment of the present invention, the concentration of the hydroxypropionic acid, hydroxypropionic acid derivatives, or mixtures thereof in said liquid feed stream is between about 5 wt % and about 60 wt %. In yet another embodiment of the present invention, the concentration of the hydroxypropionic acid, hydroxypropionic acid derivatives, or mixtures thereof in said liquid feed stream is between about 10 wt % and about 40 wt %. In even yet another embodiment of the present invention, the concentration of the hydroxypropionic acid, hydroxypropionic acid derivatives, or mixtures thereof in said liquid feed stream is about 20 wt %.

In one embodiment of the present invention, the liquid feed stream comprises an aqueous solution of hydroxypropionic acid, hydroxypropionic acid derivatives, or mixtures thereof. In another embodiment of the present invention, the liquid feed stream comprises an aqueous solution of lactic acid, lactic acid derivatives, or mixtures thereof. In yet another embodiment of the present invention, said lactic acid derivatives in said aqueous solution are selected from the group consisting of metal or ammonium salts of lactic acid, alkyl esters of lactic acid, lactic acid oligomers, cyclic di-esters of lactic acid, lactic acid anhydride, 2-alkoxypropionic acids or their alkyl esters, 2-aryloxypropionic acids or their alkyl esters, 2-acyloxypropionic acids or their alkyl esters, or a mixture thereof.

In one embodiment of the present invention, the concentration of the lactic acid, lactic acid derivatives, or mixtures thereof in said aqueous solution is between about 2 wt % and about 95 wt %. In another embodiment of the present invention, the concentration of the lactic acid, lactic acid derivatives, or mixtures thereof in said aqueous solution is between about 5 wt % and about 60 wt %. In yet another embodiment of the present invention, the concentration of the lactic acid, lactic acid derivatives, or mixtures thereof in said aqueous solution is between about 10 wt % and about 40 wt %. In even yet another embodiment of the present invention, the concentration of the lactic acid, lactic acid derivatives, or mixtures thereof in said aqueous solution is about 20 wt %. In one embodiment of the present invention, the liquid feed stream comprises an aqueous solution of lactic acid along with lactic acid derivatives. In another embodiment of the present invention, the liquid feed stream comprises less than about 30 wt % of lactic acid derivatives, based on the total weight of the liquid feed stream. In yet another embodiment of the present invention, the liquid feed stream comprises less than about 10 wt % of lactic acid derivatives, based on the total weight of the liquid feed stream. In even yet another embodiment of the present invention, the liquid feed stream comprises less than about 5 wt % of lactic acid derivatives, based on the total weight of the liquid feed stream.

Lactic acid can be in monomeric form or as oligomers in said aqueous solution of lactic acid, lactic acid derivatives, or mixtures thereof. In one embodiment of the present invention, the oligomers of the lactic acid in said aqueous solution of lactic acid, lactic acid derivatives, or mixtures thereof are less than about 30 wt % based on the total amount of lactic acid, lactic acid derivatives, or mixtures thereof. In another embodiment of the present invention, the oligomers of the lactic acid in said aqueous solution of lactic acid, lactic acid derivatives, or mixtures thereof are less than about 10 wt % based on the total amount of lactic acid, lactic acid derivatives, or mixtures thereof. In yet another embodiment of the present invention, the oligomers of the lactic acid in said aqueous solution of lactic acid, lactic acid derivatives, or mixtures thereof are less than about 5 wt % based on the total amount of lactic acid, lactic acid derivatives, or mixtures thereof. In even yet another embodiment of the present invention, the lactic acid is essentially in monomeric form in said aqueous solution of lactic acid, lactic acid derivatives, or mixtures thereof.

The process to remove the oligomers from the aqueous solution of lactic acid, lactic acid derivatives, and mixtures thereof can comprise a purification step or hydrolysis by heating step. In one embodiment of the present invention, the heating step can involve heating the aqueous solution of lactic acid, lactic acid derivatives, or mixtures thereof at a temperature between about 50° C. and about 100° C. to hydrolyze the oligomers of the lactic acid. In another embodiment of the present invention, the heating step can involve heating the aqueous solution of lactic acid, lactic acid derivatives, or mixtures thereof at a temperature between about 95° C. and about 100° C. to hydrolyze the oligomers of the lactic acid. In yet another embodiment of the present invention, the heating step can involve heating the aqueous solution of lactic acid, lactic acid derivatives, or mixtures thereof at a temperature between about 50° C. and about 100° C. to hydrolyze the oligomers of the lactic acid and produce a monomeric lactic acid aqueous solution comprising at least 80 wt % of lactic acid in monomeric form based on the total amount of lactic acid, lactic acid derivatives, or mixtures thereof. In even yet another embodiment of the present invention, the heating step can involve heating the aqueous solution of lactic acid, lactic acid derivatives, or mixtures thereof at a temperature between about 50° C. and about 100° C. to hydrolyze the oligomers of the lactic acid and produce a monomeric lactic acid aqueous solution comprising at least 95 wt % of lactic acid in monomeric form based on the total amount of lactic acid, lactic acid derivatives, or mixtures thereof. In one embodiment of the present invention, an about 88 wt % aqueous solution of lactic acid, lactic acid derivatives, or mixtures thereof is diluted with water and the oligomers are hydrolyzed to produce an aqueous solution of about 20 wt % lactic acid. The lactic acid oligomers can result in loss of acrylic acid selectivity due to their high boiling point. As the water content decreases in the aqueous solution, the loss of feed material to the catalyst reaction, due to losses in the evaporation step, increases. Additionally, lactic acid oligomers can cause coking, catalyst deactivation, and reactor plugging.

In another embodiment of the present invention, the liquid feed stream comprising hydroxypropionic acid, hydroxypropionic acid derivatives, or mixtures thereof can further comprise one or more antioxidants. In another embodiment of the present invention, the liquid feed stream comprising hydroxypropionic acid, hydroxypropionic acid derivatives, or mixtures thereof further comprises butylated hydroxy toluene (BHT), butylated hydroxy anisole (BHA), or mixtures thereof. In yet another embodiment of the present invention, the liquid feed stream comprising hydroxypropionic acid, hydroxypropionic acid derivatives, or mixtures thereof further comprises ethylene glycol, ethanedithiol, methanol, methanethiol, or mixtures thereof.

The liquid feed stream can be introduced into the evaporator or into the catalytic reactor with a simple tube or through atomization nozzles. Non-limiting examples of atomization nozzles comprise fan nozzles, pressure swirl atomizers, air blast atomizers, two-fluid atomizers, rotary atomizers, and supercritical carbon dioxide atomizers. In one embodiment of the present invention, the droplets of the aqueous solution are less than about 500 m in diameter. In another embodiment of the present invention, the droplets of the aqueous solution are less than about 200 m in diameter. In yet another embodiment of the present invention, the droplets of the aqueous solution are less than about 100 m in diameter.

In the evaporation step, said liquid feed stream or said liquid/gas blend are heated to produce a gas feed stream. In one embodiment of the present invention, the temperature during the evaporation step is between about 165° C. and about 450° C. In another embodiment of the present invention, the temperature during the evaporation step is between about 200° C. and about 400° C. In yet another embodiment of the present invention, the temperature during the evaporation step is between about 250° C. and about 375° C. In even yet another embodiment of the present invention, the temperature during the evaporation step is between about 300° C. and about 375° C. In one embodiment of the present invention, the temperature during the evaporation step is about 250° C. In another embodiment of the present invention, the temperature during the evaporation step is about 375° C.

In one embodiment of the present invention, the residence time in the evaporator during said evaporation step is between about 0.2 s and about 10 s. In another embodiment of the present invention, the residence time in the evaporator during said evaporation step is between about 0.5 s and about 5 s. In yet another embodiment of the present invention, the residence time in the evaporator during said evaporation step is between about 1 s and about 3 s. In even yet another embodiment of the present invention, the residence time in the evaporator during said evaporation step is between about 0.5 s and about 0.6 s.

The evaporation step can be performed under vacuum, at atmospheric pressure, or at pressure higher than atmospheric. In one embodiment of the present invention, the evaporation step is performed under a total pressure of at least about 1 bar. In another embodiment of the present invention, the evaporation step is performed under a total pressure between about 2 bar and about 100 bar. In yet another embodiment of the present invention, the evaporation step is performed under a pressure between about 5 bar and about 40 bar. In even yet another embodiment of the present invention, the evaporation step is performed under a total pressure between about 10 bar and about 35 bar. In one embodiment of the present invention, the evaporation step is performed under a total pressure of about 1.6 bar. In another one embodiment of the present invention, the evaporation step is performed under a total pressure of about 8 bar. In yet another embodiment of the present invention, the evaporation step is performed under a total pressure of about 26 bar.

The evaporation step can be performed in various types of evaporators, such as, but not limited to, atomizer, plate heat exchanger, empty flow reactor, and fixed bed flow reactor. The evaporation step can be performed in an evaporator with the liquid feed stream flowing down, or flowing up, or flowing horizontally. In one embodiment of the present invention, the evaporation step is performed in an evaporator with the liquid feed stream flowing down. Also, the evaporation step can be done in a batch form.

In one embodiment of the present invention, the material of the evaporator inner surface is selected from the group consisting of amorphous silica, quartz, other silicon oxides, borosilicate glass, silicon, and mixtures thereof. In yet another embodiment of the present invention, the material of the evaporator inner surface is amorphous silica or borosilicate glass.

In one embodiment of the present invention, the evaporation and dehydration steps are combined in a single step. In another embodiment of the present invention, the evaporation and dehydration steps are performed sequentially in a single reactor. In yet another embodiment of the present invention, the evaporation and dehydration steps are performed sequentially in a tandem reactor.

The acrylic acid stream produced in said dehydration is cooled to give a liquid acrylic acid stream as the product stream. The time required to cool the acrylic acid stream must be controlled to reduce acrylic acid polymerization or decomposition to ethylene. In one embodiment of the present invention, the residence time of the acrylic acid stream in the cooling step is less than about 30 s. In another embodiment of the present invention, the residence time of the acrylic acid stream in the cooling step is between about 0.1 s and about 10 s.

The liquid acrylic acid stream comprising acrylic acid, acrylic acid derivatives, or mixtures thereof produced according with the present invention can be purified using some or all of the processes of extraction, drying, distilling, cooling, partial melting, and decanting described in US20130274518A1 or US20150329462A1 (incorporated herein by reference) to produce crude and glacial acrylic acid. After purification, the crude and glacial acrylic acid can be polymerized to produce a superabsorbent polymer using processes that are similar to those described in US20130274697A1 or US20130273384A1 (incorporated herein by reference).

In one embodiment of the present invention, said crude acrylic acid is esterified with an alcohol to produce an acrylate monomer. Non-limiting examples of alcohols are methanol, ethanol, butanol (n-butyl alcohol), 2-ethyl hexanol, isobutanol, tert-butyl alcohol, hexyl alcohol, octyl alcohol, isooctyl alcohol, lauryl alcohol, propyl alcohol, isopropyl alcohol, hydroxyethyl alcohol, hydroxypropyl alcohol, and polyols, such as hydroxyalkyl and alkylalkanolamine. In another embodiment of the present invention, said crude acrylic acid is esterified with methanol, ethanol, n-butyl alcohol, or 2-ethyl hexanol to produce methyl acrylate monomer, ethyl acrylate monomer, n-butyl acrylate monomer, or 2-ethylhexyl acrylate monomer, respectively. In yet another embodiment of the present invention, said methyl acrylate monomer, ethyl acrylate monomer, n-butyl acrylate monomer, or 2-ethylhexyl acrylate monomer is polymerized to produce methyl acrylate polymer, ethyl acrylate polymer, n-butyl acrylate polymer, or 2-ethylhexyl acrylate polymer, respectively. In even yet another embodiment of the present invention, said methyl acrylate monomer, ethyl acrylate monomer, n-butyl acrylate monomer, or 2-ethylhexyl acrylate monomer is co-polymerized with other monomer to produce methyl acrylate co-polymer, ethyl acrylate co-polymer, n-butyl acrylate co-polymer, or 2-ethylhexyl acrylate co-polymer, respectively. Non-limiting examples of other monomers are vinyl acetate and ethylene. In one embodiment of the present invention, said methyl acrylate polymer, ethyl acrylate polymer, n-butyl acrylate polymer, or 2-ethylhexyl acrylate polymer is blended with methyl methacrylate (MMA) to produce blends of MMA and methyl acrylate polymer, blends of MMA and ethyl acrylate polymer, blends of MMA and n-butyl acrylate polymer, or blends of MMA and 2-ethylhexyl acrylate polymer, respectively. Non-limiting applications of polymers, co-polymers, or blends are in surface coatings, paints, resins, adhesives, plastics, and dispersions. In another embodiment of the present invention, said alcohol is bio-based alcohol. In yet another embodiment of the present invention, said other monomer is bio-based monomer. In even yet another embodiment of the present invention, said MMA is bio-based MMA.

In one embodiment of the present invention, a method of making acrylic acid comprises:
  a) diluting an about 88 wt % lactic acid aqueous solution with water to form an about 20 wt % lactic acid aqueous solution;
  b) heating the about 20 wt % lactic acid aqueous solution at a temperature between about 95° C. and about 100° C. to hydrolyze oligomers of the lactic acid, producing a monomeric lactic acid solution comprising at least about 95 wt % of the lactic acid in monomeric form based on the total amount of lactic acid, lactic acid derivatives, or mixtures thereof;
  c) combining the monomeric lactic acid solution with nitrogen to form a liquid/gas blend;
  d) evaporating the liquid/gas blend in a evaporator with a residence time between about 0.5 s and about 0.6 s at a temperature between about 300° C. and about 375° C. to produce a gas feed stream comprising about 2.5 mol % lactic acid and about 50 mol % water vapor;
  e) contacting said gas feed stream with any catalyst disclosed in Section II ("Active Catalysts for the Dehydration of Hydroxypropionic Acid or its Derivatives to Acrylic Acid or its Derivatives") or Section III ("Precursor Catalysts for the Dehydration of Hydroxypropionic Acid or its Derivatives to Acrylic Acid or its Derivatives") of the present invention in a single-layer reactor at a temperature, a water partial pressure, a GHSV, and a WHSV to dehydrate said lactic acid and produce an acrylic acid stream; wherein said water partial pressure is equal to or greater than about 0.4 bar; wherein said single-layer reactor comprises a wall, an outer surface, and an inner surface; wherein said wall is made from a wall material, has a wall thickness, and extends from said outer surface to said inner surface; wherein said wall material comprises aluminum in an amount greater than about 1 wt %; wherein said inner surface is in contact with said catalyst; wherein said single-layer reactor has a corrosion rate lower than about 1.3 mm/y during said dehydration; and f) cooling said acrylic acid stream with a residence time between about 0.1 s and about 10 s to produce said a liquid acrylic acid stream comprising said acrylic acid.

In another embodiment of the present invention, a method of making acrylic acid comprises:
a) diluting an about 88 wt % lactic acid aqueous solution with water to form an about 20 wt % lactic acid aqueous solution;
b) heating the about 20 wt % lactic acid aqueous solution at a temperature between about 95° C. and about 100° C. to hydrolyze oligomers of the lactic acid, producing a monomeric lactic acid solution comprising at least about 95 wt % of the lactic acid in monomeric form based on the total amount of lactic acid, lactic acid derivatives, or mixtures thereof;
c) combining the monomeric lactic acid solution with nitrogen to form a liquid/gas blend;
d) evaporating the liquid/gas blend in a evaporator with a residence time between about 0.5 s and about 0.6 s at a temperature between about 300° C. and about 375° C. to produce a gas feed stream comprising about 2.5 mol % lactic acid and about 50 mol % water vapor;
e) contacting said gas feed stream with a catalyst in a single-layer reactor at a temperature, a water partial pressure, a GHSV, and a WHSV to dehydrate said lactic acid and produce an acrylic acid stream; wherein said catalyst comprises a phosphate salt $CsH_{2(1-x)}PO_{(4-x)}$; wherein x is any real number greater than or equal to 0 and less than or equal to 1; wherein said single-layer reactor comprises a wall, an outer surface, and an inner surface; wherein said wall is made from a wall material, has a wall thickness, and extends from said outer surface to said inner surface; wherein said wall material comprises nickel in an amount between about 50 wt % and about 75 wt %, chromium in an amount between about 15 wt % and about 20 wt %, iron in an amount between about 3 wt % and about 30%, and aluminum in an amount between about 3 wt % and about 5 wt %; wherein said temperature is about 375° C. and said water partial pressure is about 13 bar; wherein said GHSV is about 2,300 $h^{-1}$ and said WHSV is between about 0.3 $h^{-1}$ and about 0.4 $h^{-1}$; wherein said acrylic acid is produced with a yield of at least about 80 mol % and with a selectivity of at least about 80 mol % over a TOS of about 72 h; wherein propionic acid is produced as an impurity along with said acrylic acid; wherein the selectivity of said propionic acid is less than about 1 mol % over said TOS of about 72 h; wherein said inner surface is in contact with said catalyst; and wherein said single-layer reactor has a corrosion rate lower than about 1.3 mm/y during said dehydration; and f) cooling said acrylic acid stream with a residence time between about 0.1 s and about 10 s to produce a liquid acrylic acid stream comprising said acrylic acid.

In yet another embodiment of the present invention, a method of making acrylic acid comprises:
a) diluting an about 88 wt % lactic acid aqueous solution with water to form an about 20 wt % lactic acid aqueous solution;
b) heating the about 20 wt % lactic acid aqueous solution at a temperature between about 95° C. and about 100° C. to hydrolyze oligomers of the lactic acid, producing a monomeric lactic acid solution comprising at least about 95 wt % of the lactic acid in monomeric form based on the total amount of lactic acid, lactic acid derivatives, or mixtures thereof;
c) combining the monomeric lactic acid solution with nitrogen to form a liquid/gas blend;
d) evaporating the liquid/gas blend in a evaporator with a residence time between about 0.5 s and about 0.6 s at a temperature between about 300° C. and about 375° C. to produce a gas feed stream comprising about 2.5 mol % lactic acid and about 50 mol % water;
e) contacting said gas feed stream with a catalyst in a single-layer reactor at a temperature, a water partial pressure, a GHSV, and a WHSV to dehydrate said lactic acid and produce an acrylic acid stream; wherein said catalyst comprises a phosphate salt $KH_{2(1-x)}PO_{(4-x)}$; wherein x is any real number greater than or equal to 0 and less than or equal to 1; wherein said single-layer reactor comprises a wall, an outer surface, and an inner surface; wherein said wall is made from a wall material, has a wall thickness, and extends from said outer surface to said inner surface; wherein said wall material comprises nickel in an amount between about 50 wt % and about 75 wt %, chromium in an amount between about 16 wt % and about 20 wt %, iron in an amount between about 3 wt % and about 30%, and aluminum in an amount between about 3 wt % and about 5 wt %; wherein said temperature is about 375° C. and said water partial pressure is about 13 bar; wherein said GHSV is about 2,300 $h^{-1}$ and said WHSV is between about 0.3 $h^{-1}$ and about 0.4 $h^{-1}$; wherein said acrylic acid is produced in a yield of at least about 80% and with a selectivity of at least about 80% over a TOS of about 72 h; wherein propionic acid is produced with a selectivity of less than about 1% over said TOS of about 72 h; wherein said inner surface is in contact with said catalyst; and wherein said single-layer reactor has a corrosion rate lower than about 1.3 mm/y during said dehydration; and f) cooling said acrylic acid stream with a residence time between about 0.1 s and about 10 s to produce a liquid acrylic acid stream comprising said acrylic acid.

In even yet another embodiment of the present invention, a method of making acrylic acid comprises:
a) diluting an about 88 wt % lactic acid aqueous solution with water to form an about 20 wt % lactic acid aqueous solution;
b) heating the about 20 wt % lactic acid aqueous solution at a temperature between about 95° C. and about 100° C. to hydrolyze oligomers of the lactic acid, producing a monomeric lactic acid solution comprising at least about 95 wt % of the lactic acid in monomeric form based on the total amount of lactic acid, lactic acid derivatives, or mixtures thereof;

c) combining the monomeric lactic acid solution with nitrogen to form a liquid/gas blend;

d) evaporating the liquid/gas blend in a evaporator with a residence time between about 0.5 s and about 0.6 s at a temperature between about 300° C. and about 375° C. to produce a gas feed stream comprising about 2.5 mol % lactic acid and about 50 mol % water vapor;

e) contacting said gas feed stream with a catalyst in a bi-layer reactor at a temperature, a water partial pressure, a GHSV, and a WHSV to dehydrate said lactic acid and produce an acrylic acid stream; wherein said catalyst comprises a phosphate salt $KH_{2(1-x)}PO_{(4-x)}$; wherein x is any real number greater than or equal to 0 and less than or equal to 1; wherein said bi-layer reactor comprises an outer layer, an inner layer, an outer surface, an inner surface, and an interface between said outer layer and said inner layer; wherein said outer layer is made from an outer layer material, has an outer layer thickness, and extends from said interface to said outer surface; wherein said inner layer is made from an inner layer material, has an inner layer thickness, and extends from said inner surface to said interface; wherein said inner layer material is selected from the group consisting of aluminum, silicon, and mixtures thereof; wherein said inner surface is in contact with said catalyst; wherein said outer layer is selected from the group consisting of stainless steel and carbon steel; wherein said inner layer is formed by a dipping process of said outer layer in a bath comprising said inner layer material; wherein said dipping process is followed by oxidation of said inner surface; wherein said temperature is about 375° C. and said water partial pressure is about 13 bar; wherein said GHSV is about 2,300 $h^{-1}$ and said WHSV is between about 0.3 $h^{-1}$ and about 0.4 $h^{-1}$; wherein said acrylic acid is produced with a yield of at least about 80 mol % and with a selectivity of at least about 80 mol % over a TOS of about 72 h; wherein propionic acid is produced as an impurity along with said acrylic acid; wherein the selectivity of said propionic acid is less than about 1 mol % over said TOS of about 72 h; and wherein said bi-layer reactor has a corrosion rate lower than about 1.3 mm/y during said dehydration; and f) cooling said acrylic acid stream with a residence time between about 0.1 s and about 10 s to produce a liquid acrylic acid stream comprising said acrylic acid.

VI Examples

The following examples are provided to illustrate the invention, but are not intended to limit the scope thereof.

Example 1—Precursor Catalyst with 13 wt % $KPO_3$, 37 wt % $Ba_2P_2O_7$, and 50% Fused Silica Barium nitrate $(Ba(NO_3)_2$ (150.00 g, 550.5 mmol; Sigma-Aldrich Co., St. Louis, Mo.; catalog #202754), dipotassium phosphate $K_2HPO_4$ (31.96 g, 183.5 mmol; Sigma-Aldrich Co., St. Louis, Mo.; catalog #60347), and ammonium phosphate dibasic $(NH_4)_2HPO_4$ (99.21 g, 734.0 mmol; Sigma-Aldrich Co., St. Louis, Mo.; catalog #379980) were combined and ground together using a planetary ball mill (Retsch GmbH, Haan, Germany; model PM 100; catalog #20.540.0003) to obtain a fine powder. Then, the material was transferred into a 1 L glass beaker and calcined using a lab furnace with air circulation (Nabertherm GmbH, Lilienthal, Germany; catalog # N30/85 HA; conditions: 450° C., 12 h, 2° C./min heating ramp, and open exhaust). The calcined solid was ground and sieved to obtain a solid with particle size between 106 μm and 212 μm. Then, 4.18 g of this solid and 4.18 g of fused silica (Sigma-Aldrich Co., St. Louis, Mo.; catalog #342831; ground and sieved to 106-212 μm) were added to a glass scintillation vial and mixed in a vortex mixer until well blended. The resulting precursor catalyst contained 13 wt % $KPO_3$, 37 wt % $Ba_2P_2O_7$, and 50% Fused Silica.

Example 2-20 wt % Lactic Acid Aqueous Solution 455 g of an 88 wt % L-lactic acid solution (Corbion Purac Co., Lenexa, Kans.) was diluted with 1,508 g of water. The diluted solution was heated to 95° C. and held at that temperature with stirring for about 12 hours. Then, the solution was cooled to room temperature, and its lactic acid monomer concentration was measured by an Agilent 1100 HPLC system (Agilent Technologies, Inc., Santa Clara, Calif.) equipped with a DAD detector and an Atlantis T3 column (Waters Corp., Milford, Mass.; Catalog #186003748) using methods generally known by those having ordinary skill in the art to yield a 20 wt % L-lactic acid aqueous solution and essentially free of oligomers.

Example 3—Testing of Precursor Catalyst

A stainless steel glass-lined tube reactor (SGE Analytical Science Pty Ltd., Ringwood, Australia; P/N: 08277028) with 12.7 mm (½ in.) OD, 9.5 mm ID, and 60 cm length was packed in 3 zones as follows: 1) bottom zone: 0.4 g of quartz wool, 24.1 g of 4-20 mesh fused silica (Sigma-Aldrich Co., St. Louis, Mo.; catalog #342831), and 0.2 g quartz wool were packed to give a bottom zone length of 30.5 cm (12 in.); 2) middle zone/dehydration zone: 8.81 g of the precursor catalyst prepared in Example 1 were packed to give a catalyst bed length of 10.2 cm (4 in.; 7.2 mL catalyst bed volume); and 3) top zone/evaporator zone: 0.1 g of quartz wool was placed on top of the dehydration zone followed by 3.6 g of fused silica (4-20 mesh) to give an evaporator zone of 5.1 cm (2 in.) in length.

The reactor was first placed inside an aluminum block and then placed in a Series 3210 clam shell furnace (Applied Test Systems, Butler, Pa.) such as the top of the evaporator zone was aligned with the top of the aluminum block. The reactor was set-up in a down-flow arrangement and was equipped with a Knauer Smartline 100 feed pump (Knauer GmbH, Berlin, Germany), a Brooks 0254 gas flow controller (Brooks Instrument LLC, Hatfield, Pa.), a Brooks back pressure regulator, and a Teflon-lined catch tank. The head of the reactor was fitted with a 3.2 mm (⅛ in.) stainless steel line, as a nitrogen feed line, and a 1.6 mm (¹⁄₁₆ in.) polyetheretherketone (PEEK™) tubing (Supelco Inc., Bellafonte, Pa.), as a liquid feed supply line connected to the feed pump. The bottom of the reactor was connected to the catch tank using a 3.2 mm (⅛ in.) fused silica lined stainless steel tubing and Swagelok™ fittings. The clam shell furnace was heated such that the reactor wall temperature was kept constant at about 375° C. during the course of the reaction.

The reactor was fed with separate liquid and gas feeds, which were mixed together before reaching the catalyst bed. The inert gas was nitrogen at 24.8 barg (360 psig) pressure and was fed into the reactor at a rate of 130 mL/min (under STP conditions). The liquid feed was an aqueous solution of lactic acid (20 wt % L-lactic acid from Example 2) and was fed into the reactor at a rate of 0.13 mL/min. After the evaporation zone, the resulting gas feed stream had the following composition: 49.6 mol % water, 47.9 mol % nitrogen, and 2.5 mol % lactic acid. In the dehydration zone, the GHSV was about 2,262 h$^{-1}$, WHSV was about 0.38 h$^{-1}$, and water partial pressure was about 13 bar (186 psi).

The gas product stream was cooled and analyzed on-line by an Agilent 7890A GC (Agilent Technologies, Inc., Santa Clara, Calif.) equipped with a FID detector and Varian CP-PoraBond Q column (Agilent Technologies, Inc., Santa Clara, Calif.; Catalog # CP7351). The liquid product stream was collected in the catch tank and analyzed off-line (using methods generally known by those having ordinary skill in the art) using an Agilent 1100 HPLC (Agilent Technologies, Inc., Santa Clara, Calif.), equipped with a diode array detector (DAD) and an Atlantis T3 column (Waters Corp., Milford, Mass.; Catalog #186003748), and a Hewlett Packard HP6890 series GC (Agilent Technologies, Inc., Santa Clara, Calif.), equipped with an FID detector and Agilent CP-Wax 58 FFAP CB column (Agilent Technologies, Inc., Santa Clara, Calif.; Catalog # CP7717).

The liquid product stream was cooled and collected over a period of about 72 h. The overall acrylic acid yield was 84.4 mol %, acrylic acid selectivity was 87.2 mol %, lactic acid conversion was 96.7 mol %, and propionic acid selectivity was 0.74 mol %.

Comparative Example 4-316L Stainless Steel (316L SS) Coupon

A 316L SS coupon was sanded with emery cloth (320 grit, followed by 500 grit) and cleaned with solvent (acetone, hexanes, and then chloroform). The dimensions of the coupon were measured using a micrometer as 30.03 mm×8.01 mm×1.5 mm, and the weight of coupon was measured as 2,819.80 mg before being placed in the reactor. The nominal chemical composition of this alloy includes about 65 wt % iron, about 17 wt % chromium, about 12 wt % nickel, and 2-3 wt % molybdenum.

Comparative Example 5—Corrosion Testing of the 316L SS Coupon

A stainless steel glass-lined tube reactor (SGE Analytical Science Pty Ltd., Ringwood, Australia; P/N: 08277028) with 12.7 mm (½ in.) OD, 9.5 mm ID, and 60 cm length was packed in 3 zones as follows: 1) bottom zone: 0.4 g of quartz wool, 25.15 g of 4-20 mesh fused silica (Sigma-Aldrich Co., St. Louis, Mo.; catalog #342831), and 0.1 g quartz wool were packed to give a bottom zone length of 29.5 cm (11.6 in.); 2) middle zone/dehydration zone: 1.44 g of the precursor catalyst prepared in Example 1 were packed to give a catalyst bed length of 2.54 cm (1 in.) at the bottom of this zone, the 316L SS coupon prepared in Comparative Example 4 was then placed on top of that precursor catalyst, and then an additional 7.31 g of the precursor catalyst prepared in Example 1 were packed around and on top of the coupon to give a catalyst bed of 10.2 cm (4 in.) in total length (a total of 8.75 g of precursor catalyst mass and 7.2 mL catalyst bed volume); and 3) top zone/evaporator zone: 0.1 g of quartz wool was placed on top of the dehydration zone followed by 3.8 g of fused silica (4-20 mesh) to give an evaporator zone of 5.1 cm (2 in.) in length.

The reactor was first placed inside an aluminum block and then placed in a Series 3210 clam shell furnace (Applied Test Systems, Butler, Pa.) such as the top of the evaporator zone was aligned with the top of the aluminum block. The reactor was set-up in a down-flow arrangement and was equipped with a Knauer Smartline 100 feed pump (Knauer GmbH, Berlin, Germany), a Brooks 0254 gas flow controller (Brooks Instrument LLC, Hatfield, Pa.), a Brooks back pressure regulator, and a Teflon-lined catch tank. The head of the reactor was fitted with a 3.2 mm (⅛ in.) stainless steel line, as a nitrogen feed line, and a 1.6 mm (1/16 in.) polyetheretherketone (PEEK™) tubing (Supelco Inc., Bellafonte, Pa.), as a liquid feed supply line connected to the feed pump. The bottom of the reactor was connected to the catch tank using a 3.2 mm (⅛ in.) fused silica lined stainless steel tubing and Swagelok™ fittings. The clam shell furnace was heated such that the reactor wall temperature was kept constant at about 375° C. during the course of the reaction.

The reactor was fed with separate liquid and gas feeds, which were mixed together before reaching the catalyst bed. The inert gas was nitrogen at 24.8 barg (360 psig) pressure and was fed into the reactor at a rate of 130 mL/min (under STP conditions). The liquid feed was an aqueous solution of lactic acid (20 wt % L-lactic acid from Example 2) and was fed into the reactor at a rate of 0.13 mL/min. After the evaporation zone, the resulting gas feed stream had the following composition: 49.6 mol % water, 47.9 mol % nitrogen, and 2.5 mol % lactic acid. In the dehydration zone, the GHSV was about 2,262 h$^{-1}$, WHSV was about 0.38 h$^{-1}$, and water partial pressure was about 13 bar (186 psi).

The gas product stream was cooled and analyzed on-line by an Agilent 7890A GC (Agilent Technologies, Inc., Santa Clara, Calif.) equipped with a FID detector and Varian CP-PoraBond Q column (Agilent Technologies, Inc., Santa Clara, Calif.; Catalog # CP7351). The liquid product stream was collected in the catch tank and analyzed off-line (using methods generally known by those having ordinary skill in the art) using an Agilent 1100 HPLC (Agilent Technologies, Inc., Santa Clara, Calif.), equipped with a diode array detector (DAD) and an Atlantis T3 column (Waters Corp., Milford, Mass.; Catalog #186003748), and a Hewlett Packard HP6890 series GC (Agilent Technologies, Inc., Santa Clara, Calif.), equipped with an FID detector and Agilent CP-Wax 58 FFAP CB column (Agilent Technologies, Inc., Santa Clara, Calif.; Catalog # CP7717).

The liquid product stream was cooled and collected over a period of about 72 h. The overall (i.e., over the 72 h period) acrylic acid yield was 81.7 mol %, acrylic acid selectivity was 83.8 mol %, lactic acid conversion was 97.5 mol %, and propionic acid selectivity was 2.02 mol %. At the end of the experiment, the coupon was taken out of the dehydration zone and the corrosion rate was calculated as 3.04 mm/y.

Example 6—Heat-Treated HAYNES® 214® Alloy Coupon

A HAYNES® 214® alloy coupon (Haynes International Inc., Kokomo, Ind.) was sanded with emery cloth (320 grit, followed by 500 grit), cleaned with solvent (acetone, hexanes, and then chloroform) and heat treated (i.e., oxidized) in a muffle furnace (1 h at 600° C., followed by 1 h at 1000° C.; Wilt Industries Inc., Lake Pleasant, N.Y.) before use. The dimensions of the coupon were measured using a micrometer as 30.38 mm×7.97 mm×1.48 mm, and the weight of coupon was measured as 2,768.44 mg before being placed in the reactor. The nominal chemical composition of this alloy includes about 75 wt % nickel, about 16 wt % chromium, about 3 wt % iron, and about 4.5 wt % aluminum. The heat treatment of the coupon (i.e., the oxidation occurred before the dehydration) aimed at oxidizing the aluminum included in the alloy and forming an oxide-based surface passivating layer comprising alumina.

Example 7—Corrosion Testing of the Heat-Treated HAYNES® 214® Alloy Coupon

A stainless steel glass-lined tube reactor (SGE Analytical Science Pty Ltd., Ringwood, Australia; P/N: 08277028) with 12.7 mm (½ in.) OD, 9.5 mm ID, and 60 cm length was packed in 3 zones as follows: 1) bottom zone: 0.4 g of quartz wool, 25.19 g of 4-20 mesh fused silica (Sigma-Aldrich Co., St. Louis, Mo.; catalog #342831), and 0.1 g quartz wool were packed to give a bottom zone length of 29.5 cm (11.6 in.); 2) middle zone/dehydration zone: 2.18 g of the precursor catalyst prepared in Example 1 were packed to give a catalyst bed length of 2.54 cm (1 in.) at the bottom of this zone, the heat-treated HAYNES® 214® alloy coupon prepared in Example 6 was then placed on top of that precursor catalyst, and then an additional 6.18 g of the precursor catalyst prepared in Example 1 were packed around and on top of the coupon to give a catalyst bed of 10.2 cm (4 in.) in total length (a total of 8.36 g of precursor catalyst mass and 7.2 mL catalyst bed volume); and 3) top zone/evaporator zone: 0.1 g of quartz wool was placed on top of the dehydration zone followed by 4.32 g of fused silica (4-20 mesh) to give an evaporator zone of 5.1 cm (2 in.) in length.

The reactor was first placed inside an aluminum block and then placed in a Series 3210 clam shell furnace (Applied Test Systems, Butler, Pa.) such as the top of the evaporator zone was aligned with the top of the aluminum block. The reactor was set-up in a down-flow arrangement and was equipped with a Knauer Smartline 100 feed pump (Knauer GmbH, Berlin, Germany), a Brooks 0254 gas flow controller (Brooks Instrument LLC, Hatfield, Pa.), a Brooks back pressure regulator, and a Teflon-lined catch tank. The head of the reactor was fitted with a 3.2 mm (⅛ in.) stainless steel line, as a nitrogen feed line, and a 1.6 mm (1/16 in.) polyetheretherketone (PEEK™) tubing (Supelco Inc., Bellafonte, Pa.), as a liquid feed supply line connected to the feed pump. The bottom of the reactor was connected to the catch tank using a 3.2 mm (⅛ in.) fused silica lined stainless steel tubing and Swagelok™ fittings. The clam shell furnace was heated such that the reactor wall temperature was kept constant at about 375° C. during the course of the reaction.

The reactor was fed with separate liquid and gas feeds, which were mixed together before reaching the catalyst bed. The inert gas was nitrogen at 24.8 barg (360 psig) pressure and was fed into the reactor at a rate of 130 mL/min (under STP conditions). The liquid feed was an aqueous solution of lactic acid (20 wt % L-lactic acid from Example 2) and was fed into the reactor at a rate of 0.13 mL/min. After the evaporation zone, the resulting gas feed stream had the following composition: 49.6 mol % water, 47.9 mol % nitrogen, and 2.5 mol % lactic acid. In the dehydration zone, the GHSV was about 2,262 h$^{-1}$, WHSV was about 0.38 h$^{-1}$, and water partial pressure was about 13 bar (186 psi).

The gas product stream was cooled and analyzed on-line by an Agilent 7890A GC (Agilent Technologies, Inc., Santa Clara, Calif.) equipped with a FID detector and Varian CP-PoraBond Q column (Agilent Technologies, Inc., Santa Clara, Calif.; Catalog # CP7351). The liquid product stream was collected in the catch tank and analyzed off-line (using methods generally known by those having ordinary skill in the art) using an Agilent 1100 HPLC (Agilent Technologies, Inc., Santa Clara, Calif.), equipped with a diode array detector (DAD) and an Atlantis T3 column (Waters Corp., Milford, Mass.; Catalog #186003748), and a Hewlett Packard HP6890 series GC (Agilent Technologies, Inc., Santa Clara, Calif.), equipped with an FID detector and Agilent CP-Wax 58 FFAP CB column (Agilent Technologies, Inc., Santa Clara, Calif.; Catalog # CP7717).

The liquid product stream was cooled and collected over a period of about 72 h. The overall (i.e., over the 72 h period) acrylic acid yield was 86.2 mol %, acrylic acid selectivity was 88.5 mol %, lactic acid conversion was 97.3 mol %, and propionic acid selectivity was 0.58 mol %. At the end of the experiment, the coupon was taken out of the dehydration zone and the corrosion rate was calculated as 0.79 mm/y.

Example 8—HAYNES® HR-160® Alloy Coupon

A HAYNES® HR-160® alloy coupon (Haynes International Inc., Kokomo, Ind.) was sanded with emery cloth (320 grit, followed by 500 grit) and cleaned with solvent (acetone, hexanes, and then chloroform) before use. The dimensions of the coupon were measured using a micrometer as 29.13 mm×8.20 mm×1.51 mm, and the weight of coupon was measured as 2,710.33 mg before being placed in the reactor. The nominal chemical composition of this alloy includes about 37 wt % nickel, about 29 wt % cobalt, about 28 wt % chromium, about 2 wt % iron, and about 2.75 wt % silicon. Note that the coupon was not heat treated before use (i.e., no oxidation occurred before the dehydration), and thus no oxide-based surface passivating layer, comprising silica, is expected to have been formed before dehydration.

Example 9—Corrosion Testing of the HAYNES® HR-160® Alloy Coupon

A stainless steel glass-lined tube reactor (SGE Analytical Science Pty Ltd., Ringwood, Australia; P/N: 08277028) with 12.7 mm (½ in.) OD, 9.5 mm ID, and 60 cm length was packed in 3 zones as follows: 1) bottom zone: 0.4 g of quartz wool, 24.64 g of 4-20 mesh fused silica (Sigma-Aldrich Co., St. Louis, Mo.; catalog #342831), and 0.1 g quartz wool were packed to give a bottom zone length of 29.5 cm (11.6 in.); 2) middle zone/dehydration zone: 2.41 g of the precursor catalyst prepared in Example 1 were packed to give a catalyst bed length of 2.54 cm (1 in.) at the bottom of this zone, the HAYNES® HR-160® coupon prepared in Example 8 was then placed on top of that precursor catalyst, and then an additional 6.63 g of the precursor catalyst prepared in Example 1 were packed around and on top of the coupon to give a catalyst bed of 10.2 cm (4 in.) in total length (a total of 9.04 g of precursor catalyst mass and 7.2 mL catalyst bed volume); and 3) top zone/evaporator zone: 0.1 g of quartz wool was placed on top of the dehydration zone followed by 4.38 g of fused silica (4-20 mesh) to give an evaporator zone of 5.1 cm (2 in.) in length.

The reactor was first placed inside an aluminum block and then placed in a Series 3210 clam shell furnace (Applied Test Systems, Butler, Pa.) such as the top of the evaporator zone was aligned with the top of the aluminum block. The reactor was set-up in a down-flow arrangement and was equipped with a Knauer Smartline 100 feed pump (Knauer GmbH, Berlin, Germany), a Brooks 0254 gas flow controller (Brooks Instrument LLC, Hatfield, Pa.), a Brooks back pressure regulator, and a Teflon-lined catch tank. The head of the reactor was fitted with a 3.2 mm (⅛ in.) stainless steel line, as a nitrogen feed line, and a 1.6 mm (1/16 in.) polyetheretherketone (PEEK™) tubing (Supelco Inc., Bellafonte, Pa.), as a liquid feed supply line connected to the feed pump. The bottom of the reactor was connected to the catch tank using a 3.2 mm (⅛ in.) fused silica lined stainless steel tubing and Swagelok™ fittings. The clam shell furnace was heated such that the reactor wall temperature was kept constant at about 375° C. during the course of the reaction.

The reactor was fed with separate liquid and gas feeds, which were mixed together before reaching the catalyst bed. The inert gas was nitrogen at 24.8 barg (360 psig) pressure and was fed into the reactor at a rate of 130 mL/min (under STP conditions). The liquid feed was an aqueous solution of lactic acid (20 wt % L-lactic acid from Example 2) and was fed into the reactor at a rate of 0.13 mL/min. After the evaporation zone, the resulting gas feed stream had the following composition: 49.6 mol % water, 47.9 mol % nitrogen, and 2.5 mol % lactic acid. In the dehydration zone, the GHSV was about 2,262 $h^{-1}$, WHSV was about 0.38 $h^{-1}$, and water partial pressure was about 13 bar (186 psi).

The gas product stream was cooled and analyzed on-line by an Agilent 7890A GC (Agilent Technologies, Inc., Santa Clara, Calif.) equipped with a FID detector and Varian CP-PoraBond Q column (Agilent Technologies, Inc., Santa Clara, Calif.; Catalog # CP7351). The liquid product stream was collected in the catch tank and analyzed off-line (using methods generally known by those having ordinary skill in the art) using an Agilent 1100 HPLC (Agilent Technologies, Inc., Santa Clara, Calif.), equipped with a diode array detector (DAD) and an Atlantis T3 column (Waters Corp., Milford, Mass.; Catalog #186003748), and a Hewlett Packard HP6890 series GC (Agilent Technologies, Inc., Santa Clara, Calif.), equipped with an FID detector and Agilent CP-Wax 58 FFAP CB column (Agilent Technologies, Inc., Santa Clara, Calif.; Catalog # CP7717).

The liquid product stream was cooled and collected over a period of about 72 h. The overall (i.e., over the 72 h period) acrylic acid yield was 88 mol %, acrylic acid selectivity was 89.4 mol %, lactic acid conversion was 98.4 mol %, and propionic acid selectivity was 0.42 mol %. At the end of the experiment, the coupon was taken out of the dehydration zone and the corrosion rate was calculated as 1.22 mm/y.

Example 10—Copper Coupon

A copper coupon was sanded with emery cloth (320 grit, followed by 500 grit). The dimensions of the coupon were measured using a micrometer as 29.46 mm×7.66 mm×1.18 mm, and the weight of coupon was measured as 2,400.59 mg before being placed in the reactor.

Example 11—Corrosion Testing of the Copper Coupon

A stainless steel glass-lined tube reactor (SGE Analytical Science Pty Ltd., Ringwood, Australia; P/N: 08277028) with 12.7 mm (½ in.) OD, 9.5 mm ID, and 60 cm length was packed in 3 zones as follows: 1) bottom zone: 0.4 g of quartz wool, 22.33 g of 4-20 mesh fused silica (Sigma-Aldrich Co., St. Louis, Mo.; catalog #342831), and 0.1 g quartz wool were packed to give a bottom zone length of 29.5 cm (11.6 in.); 2) middle zone/dehydration zone: 2.05 g of the precursor catalyst prepared in Example 1 were packed to give a catalyst bed length of 2.54 cm (1 in.) at the bottom of this zone, the copper coupon prepared in Example 10 was then placed on top of that precursor catalyst, and then an additional 5.63 g of the precursor catalyst prepared in Example 1 were packed around and on top of the coupon to give a catalyst bed of 10.2 cm (4 in.) in total length (a total of 7.68 g of precursor catalyst mass and 7.2 mL catalyst bed volume); and 3) top zone/evaporator zone: 0.1 g of quartz wool was placed on top of the dehydration zone followed by 3.93 g of fused silica (4-20 mesh) to give an evaporator zone of 5.1 cm (2 in.) in length.

The reactor was first placed inside an aluminum block and then placed in a Series 3210 clam shell furnace (Applied Test Systems, Butler, Pa.) such as the top of the evaporator zone was aligned with the top of the aluminum block. The reactor was set-up in a down-flow arrangement and was equipped with a Knauer Smartline 100 feed pump (Knauer GmbH, Berlin, Germany), a Brooks 0254 gas flow controller (Brooks Instrument LLC, Hatfield, Pa.), a Brooks back pressure regulator, and a Teflon-lined catch tank. The head of the reactor was fitted with a 3.2 mm (⅛ in.) stainless steel line, as a nitrogen feed line, and a 1.6 mm (1/16 in.) polyetheretherketone (PEEK™) tubing (Supelco Inc., Bellafonte, Pa.), as a liquid feed supply line connected to the feed pump. The bottom of the reactor was connected to the catch tank using a 3.2 mm (⅛ in.) fused silica lined stainless steel tubing and Swagelok™ fittings. The clam shell furnace was heated such that the reactor wall temperature was kept constant at about 375° C. during the course of the reaction.

The reactor was fed with separate liquid and gas feeds, which were mixed together before reaching the catalyst bed. The inert gas was nitrogen at 24.8 barg (360 psig) pressure and was fed into the reactor at a rate of 130 mL/min (under STP conditions). The liquid feed was an aqueous solution of lactic acid (20 wt % L-lactic acid from Example 2) and was fed into the reactor at a rate of 0.13 mL/min. After the evaporation zone, the resulting gas feed stream had the following composition: 49.6 mol % water, 47.9 mol % nitrogen, and 2.5 mol % lactic acid. In the dehydration zone, the GHSV was about 2,262 $h^{-1}$, WHSV was about 0.38 $h^{-1}$, and water partial pressure was about 13 bar (186 psi).

The gas product stream was cooled and analyzed on-line by an Agilent 7890A GC (Agilent Technologies, Inc., Santa Clara, Calif.) equipped with a FID detector and Varian CP-PoraBond Q column (Agilent Technologies, Inc., Santa Clara, Calif.; Catalog # CP7351). The liquid product stream was collected in the catch tank and analyzed off-line (using methods generally known by those having ordinary skill in the art) using an Agilent 1100 HPLC (Agilent Technologies, Inc., Santa Clara, Calif.), equipped with a diode array detector (DAD) and an Atlantis T3 column (Waters Corp., Milford, Mass.; Catalog #186003748), and a Hewlett Packard HP6890 series GC (Agilent Technologies, Inc., Santa Clara, Calif.), equipped with an FID detector and Agilent CP-Wax 58 FFAP CB column (Agilent Technologies, Inc., Santa Clara, Calif.; Catalog # CP7717).

The liquid product stream was cooled and collected over a period of about 72 h. The overall (i.e., over the 72 h period) acrylic acid yield was 86 mol %, acrylic acid selectivity was 88.1 mol %, lactic acid conversion was 97.6 mol %, and propionic acid selectivity was 0.53 mol %. At the end of the experiment, the coupon was taken out of the dehydration zone and no corrosion was observed, so that the corrosion rate was calculated as 0 mm/y.

Tabulated results from the Examples can be seen in Table 1 below.

TABLE 1

| Example #'s for Catalyst/ Coupon/ Testing | Coupon/Corrosion Resistant Reactor Metal/ Predehydration Oxidation? | Overall Acrylic Acid Yield, [mol %] | Overall Acrylic Acid Selectivity, [mol %] | Overall Lactic Acid Conversion, [mol %] | Overall Propionic Acid Selectivity, [mol %] | Corrosion Rate, [mm/y] |
|---|---|---|---|---|---|---|
| Baseline; 1/—/3 | No/—/— | 84.4 | 87.2 | 96.7 | 0.74 | — |
| Comparative; 1/4/5 | 316L SS/—/— | 81.7 | 83.8 | 97.5 | 2.02 | 3.04 |
| Inventive; 1/6/7 | Heat-treated HAYNES ® 214 ®/Al/Yes | 86.2 | 88.5 | 97.3 | 0.58 | 0.79 |
| Inventive; 1/8/9 | HAYNES ® HR-160 ®/Si/No | 88 | 89.4 | 98.4 | 0.42 | 1.22 |
| Inventive; 1/10/11 | Cu/Cu/No | 86 | 88.1 | 97.6 | 0.53 | 0 |

The foregoing description is given for clearness of understanding only, and no unnecessary limitations should be understood therefrom, as modifications within the scope of the invention may be apparent to those having ordinary skill in the art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making acrylic acid, acrylic acid derivatives, or mixtures thereof comprising contacting a gas feed stream comprising water vapor and hydroxypropionic acid, hydroxypropionic acid derivatives, or mixtures thereof with an active catalyst in a single-layer reactor at a temperature, a water partial pressure, a GHSV, and a WHSV to dehydrate said hydroxypropionic acid, hydroxypropionic acid derivatives, or mixtures thereof, resulting in the production of acrylic acid, acrylic acid derivatives, or mixtures thereof; wherein said active catalyst comprises a phosphate salt comprising a cation and an anion represented by the empirical formula:

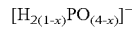

$[H_{2(1-x)}PO_{(4-x)}]^-$ wherein x is any real number greater than 0 and less than 1; wherein said water partial pressure is equal to or greater than about 0.4 bar; wherein said single-layer reactor comprises a wall, an outer surface, and an inner surface; wherein said wall is made from a wall material, has a wall thickness, and extends from said outer surface to said inner surface; wherein said wall material comprises silicon in an amount between about 1 wt % and about 50 wt %; wherein said inner surface is in contact with said active catalyst; and wherein said single-layer reactor has a corrosion rate lower than about 1.3 mm/y during said dehydration.

2. The method of claim 1; wherein said wall material further comprises nickel in an amount between about 10 wt % and about 65 wt %, chromium in an amount between about 15 wt % and about 30 wt %, and iron in an amount between about 2 wt % and about 65 wt %.

3. The method of claim 1; wherein said inner surface is subjected to oxidation and forms an oxide-based surface passivating layer comprising silica.

* * * * *